(12) United States Patent
Laing et al.

(10) Patent No.: US 12,320,799 B2
(45) Date of Patent: *Jun. 3, 2025

(54) METHODS OF MEASURING SIGNALING PATHWAY ACTIVITY FOR SELECTION OF THERAPEUTIC AGENTS

(71) Applicant: Celcuity Inc., Minneapolis, MN (US)

(72) Inventors: Lance Gavin Laing, Orono, MN (US); Brian Francis Sullivan, Medina, MN (US)

(73) Assignee: Celcuity Inc., Minneapolis, MN (US)

( * ) Notice: Subject to any disclaimer, the term of this patent is extended or adjusted under 35 U.S.C. 154(b) by 311 days.

This patent is subject to a terminal disclaimer.

(21) Appl. No.: 17/720,067

(22) Filed: Apr. 13, 2022

(65) Prior Publication Data
US 2023/0125427 A1    Apr. 27, 2023

Related U.S. Application Data

(60) Division of application No. 16/116,392, filed on Aug. 29, 2018, now Pat. No. 11,333,659, which is a continuation of application No. PCT/US2018/022936, filed on Mar. 16, 2018.

(60) Provisional application No. 62/587,572, filed on Nov. 17, 2017, provisional application No. 62/473,936, filed on Mar. 20, 2017.

(51) Int. Cl.
| | |
|---|---|
| *G01N 31/00* | (2006.01) |
| *A61K 31/407* | (2006.01) |
| *A61K 31/4709* | (2006.01) |
| *A61K 31/4985* | (2006.01) |
| *A61K 31/506* | (2006.01) |
| *A61K 45/06* | (2006.01) |
| *G01N 33/50* | (2006.01) |
| *G01N 33/53* | (2006.01) |
| *G01N 33/574* | (2006.01) |

(52) U.S. Cl.
CPC ........ *G01N 33/5011* (2013.01); *A61K 31/407* (2013.01); *A61K 31/4709* (2013.01); *A61K 31/4985* (2013.01); *A61K 31/506* (2013.01); *A61K 45/06* (2013.01); *G01N 33/5044* (2013.01); *G01N 33/57484* (2013.01); *G01N 33/5017* (2013.01); *G01N 33/5041* (2013.01); *G01N 2333/71* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 6,041,642 A | 3/2000 | Duncan |
| 6,077,684 A | 6/2000 | Kravtsov |
| 6,258,553 B1 | 7/2001 | Kravtsov |
| 6,331,392 B1 | 12/2001 | Laing et al. |
| 6,372,772 B1 | 4/2002 | Kirkpatrick et al. |
| 6,399,078 B1 | 6/2002 | Devico et al. |
| 6,569,628 B2 | 5/2003 | Laing et al. |
| 6,673,596 B1 | 1/2004 | Sayler et al. |
| 6,974,706 B1 | 12/2005 | Melker et al. |
| 7,192,752 B2 | 3/2007 | Xu et al. |
| 7,429,492 B2 | 9/2008 | Lin et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,560,269 B2 | 7/2009 | Wang et al. |
| 7,592,188 B2 | 9/2009 | Hahn et al. |
| 7,628,085 B2 | 12/2009 | Laing et al. |
| 7,790,406 B2 | 9/2010 | Cunningham et al. |
| 7,832,291 B2 | 11/2010 | Laing et al. |
| 7,863,052 B2 | 1/2011 | Schulz et al. |
| 7,927,822 B2 | 4/2011 | Genick et al. |
| 7,960,170 B2 | 6/2011 | Schulz et al. |
| 8,061,220 B2 | 11/2011 | Laing et al. |
| 8,168,568 B1 | 5/2012 | Mehta et al. |
| 8,202,735 B2 | 6/2012 | Genick et al. |

(Continued)

FOREIGN PATENT DOCUMENTS

| | | |
|---|---|---|
| JP | 2011514522 A | 5/2011 |
| JP | 2012526992 A | 11/2012 |

(Continued)

OTHER PUBLICATIONS

Du Z. et al., "Mechanisms of receptor tyrosine kinase activation in cancer," Molecular Cancer, vol. 17(1) 13 pages (2018).
Extended European Search Report, European Application No. 21159001. 3, dated Oct. 21, 2021, 14 pages.
Gimple, R. et al., "RAS: Striking at the Core of the Oncogenic Circuitry," Frontiers in Oncology, vol. 9 (2019).
International Preliminary Report on Patentability, PCT/US2020/063890, dated Feb. 18, 2022, 8 pages.
International Search Report and Written Opinion, PCT/US2020/063890, dated Mar. 19, 2021, 25 pages.
Rana, P. et al., "Efficacy and Tolerability of Lapatinib in the Management of Breast Cancer," Breast Cancer: Basic Clinical Research, vol. 6:67-77 (2012).
Abassi, Y., "Label-Free and Dynamic Monitoring of cell-Based Assays", Cell Analysis, Biochemica, No. 2, 8-11 (2008).

(Continued)

*Primary Examiner* — Lisa V Cook
(74) *Attorney, Agent, or Firm* — Nelson Mullins Riley & Scarborough LLP; Jane E. Remillard, Esq.; Catherine J. Kara, Esq.

(57) ABSTRACT

Provided herein are methods for simultaneously determining the functional status of multiple signaling pathways in a diseased cell sample obtained from a subject to thereby select for therapeutic use in the subject a targeted therapeutic agent that affects the signaling pathway with the highest level of aberrant activity in the subject's cells. Also provided are methods for determining whether a signaling pathway is ultrasensitive in a diseased cell sample from a subject, also allowing for selection of an effective targeted therapeutic agent for therapeutic use in the subject. Methods of administering a selected targeted therapeutic agent to the subject are also provided.

11 Claims, 1 Drawing Sheet

(56) References Cited

U.S. PATENT DOCUMENTS

| | | |
|---|---|---|
| 8,257,936 B2 | 9/2012 | Laing et al. |
| 8,298,780 B2 | 10/2012 | Wagner et al. |
| 9,404,915 B2 | 8/2016 | Laing et al. |
| 10,041,934 B2 | 8/2018 | Laing et al. |
| 10,976,307 B2 | 4/2021 | Laing et al. |
| 11,073,509 B2 | 7/2021 | Laing et al. |
| 11,333,659 B2* | 5/2022 | Laing ............... A61K 31/4709 |
| 2002/0031778 A1 | 3/2002 | Laing et al. |
| 2003/0004140 A1 | 1/2003 | Dalton et al. |
| 2003/0096275 A1 | 5/2003 | Laing |
| 2003/0152992 A1 | 8/2003 | Laing et al. |
| 2004/0084307 A1 | 5/2004 | Kim et al. |
| 2004/0115713 A1 | 6/2004 | Laing |
| 2004/0115786 A1 | 6/2004 | Laing |
| 2005/0130321 A1 | 6/2005 | Nicholson et al. |
| 2006/0003372 A1 | 1/2006 | Li et al. |
| 2006/0120204 A1 | 6/2006 | Abassi et al. |
| 2006/0141508 A1 | 6/2006 | Palmer |
| 2006/0160109 A1 | 7/2006 | MacDonald et al. |
| 2006/0177476 A1 | 8/2006 | Saffran |
| 2006/0275825 A1 | 12/2006 | Baird et al. |
| 2006/0292581 A1 | 12/2006 | Laing |
| 2007/0065415 A1 | 3/2007 | Kleinsek et al. |
| 2007/0172894 A1 | 7/2007 | Genick et al. |
| 2008/0020480 A1 | 1/2008 | Lin et al. |
| 2008/0115567 A1 | 5/2008 | Laing et al. |
| 2008/0240543 A1 | 10/2008 | Budach et al. |
| 2008/0299673 A1 | 12/2008 | Wagner et al. |
| 2009/0017488 A1 | 1/2009 | Binder et al. |
| 2009/0060970 A1 | 3/2009 | Toner et al. |
| 2009/0102981 A1 | 4/2009 | Mody |
| 2009/0130703 A1 | 5/2009 | Wagner et al. |
| 2009/0137422 A1 | 5/2009 | Laing et al. |
| 2009/0142790 A1 | 6/2009 | Fang et al. |
| 2009/0192049 A1 | 7/2009 | Baird et al. |
| 2009/0226950 A1 | 9/2009 | Cunningham et al. |
| 2009/0282931 A1 | 11/2009 | Laing et al. |
| 2009/0298162 A1 | 12/2009 | Bouvier et al. |
| 2009/0305304 A1 | 12/2009 | Laing et al. |
| 2010/0003743 A1 | 1/2010 | Schulz et al. |
| 2010/0015721 A1 | 1/2010 | Laing |
| 2010/0043571 A1 | 2/2010 | Laing et al. |
| 2010/0098166 A1 | 4/2010 | Budagavi et al. |
| 2010/0140087 A1 | 6/2010 | Ueno et al. |
| 2010/0143959 A1 | 6/2010 | Cunningham et al. |
| 2010/0196925 A1 | 8/2010 | Genick et al. |
| 2010/0202923 A1 | 8/2010 | Cunningham et al. |
| 2010/0227769 A1 | 9/2010 | Schulz et al. |
| 2010/0291575 A1 | 11/2010 | Shamah et al. |
| 2010/0329933 A1 | 12/2010 | Schulz et al. |
| 2011/0117542 A1 | 5/2011 | Abassi et al. |
| 2011/0130302 A1 | 6/2011 | Shen et al. |
| 2011/0195047 A1 | 8/2011 | Aldabe Arregui et al. |
| 2011/0231103 A1 | 9/2011 | Fang |
| 2012/0022048 A1 | 1/2012 | Lori et al. |
| 2012/0040866 A1 | 2/2012 | Laing et al. |
| 2012/0101230 A1 | 4/2012 | Wang et al. |
| 2012/0107840 A1 | 5/2012 | Wagner et al. |
| 2012/0237502 A1 | 9/2012 | Darnowski |
| 2013/0045880 A1 | 2/2013 | Singh et al. |
| 2013/0210057 A1 | 8/2013 | Deng et al. |
| 2013/0330761 A1 | 12/2013 | Laing et al. |
| 2015/0125894 A1 | 5/2015 | Laing et al. |
| 2016/0305932 A1 | 10/2016 | Laing et al. |
| 2017/0067875 A1 | 3/2017 | Laing et al. |
| 2017/0343554 A1 | 11/2017 | Sullivan et al. |
| 2018/0321222 A1 | 11/2018 | Laing et al. |
| 2019/0025287 A1 | 1/2019 | Laing et al. |
| 2021/0215673 A1 | 7/2021 | Laing et al. |
| 2022/0412957 A1 | 12/2022 | Laing et al. |

FOREIGN PATENT DOCUMENTS

| | | |
|---|---|---|
| JP | 2013-543006 A | 11/2013 |
| JP | 2015-527055 A | 9/2015 |
| WO | 03/008530 A2 | 1/2003 |
| WO | 2006/113747 A2 | 10/2006 |
| WO | 2006108183 A2 | 10/2006 |
| WO | 2007/081779 A2 | 7/2007 |
| WO | 2009073916 A1 | 6/2009 |
| WO | 2009108637 A1 | 9/2009 |
| WO | 2010/052225 A1 | 5/2010 |
| WO | 2010/085845 A1 | 8/2010 |
| WO | 2010/098166 A1 | 9/2010 |
| WO | 2010132723 A1 | 11/2010 |
| WO | 2012068435 A1 | 5/2012 |
| WO | 2012/157647 A1 | 11/2012 |
| WO | 2013033623 A1 | 3/2013 |
| WO | 2013086301 A1 | 6/2013 |
| WO | 2013/188500 A1 | 12/2013 |
| WO | 2014/083178 A1 | 6/2014 |
| WO | 2015089380 A2 | 6/2015 |
| WO | 2016/094904 A1 | 6/2016 |
| WO | 2018/175251 A1 | 9/2018 |

OTHER PUBLICATIONS

Ablin, R. J. et al., "Prostate Transglutaminase (TGase-4) Antagonizes the Anti-tumour Action of MDA-7/IL-24 in Prostate Cancer," Journal of Translational Medicine, vol. 9 (49): 1-8 (2008).

Aroui, S. et al., "Naringin suppresses cell metastasis and the expression of matrix metalloproteinases (MMP-2 and MMP-9) via the inhibition of ERK-P38-JNK signaling pathway in human glioblastoma," Chemico-Biological Interactions, vol. 244:195-203 (2015).

Arteaga, C. et al., "ERBB Receptors: From Oncogene Discovery to Basic Science to Mechanism-Based Cancer Therapeutics," Cancer Cell, vol. 25(3):282-303 (2014).

Atienza, J. et al., "Label-free and real-time cell-based kinase assay for; screening selective and potent receptor tyrosine kinase inhibitors using microelectronic sensor array", Journal of Biomolecular Screening, vol. 11(6): 634-643 ;2006).

Bohunicky, B. et al., "Biosensors: the new wave in cancer diagnosis," Nanotechnology, Science and Applications, vol. 4:1-10 (2010).

Bosanquet, D. et al.,"Expression of IL-24 and IL-24 Receptors in Human Wound Tissues and the Biological Implications of IL-24 on Keratinocytes," Wound Repair and Regeneration, vol. 20: 896-903 (2012).

Brower, S. et al., "The ChemoFx® Assay: An Ex Vivo Chemosensitivity and Resistance Assay for Predicting Patient Response to Cancer Chemotherapy," Methods in Molecular Biology, vol. 414: Apoptosis and Cancer, 57-78 (2007).

Buck, E. et al., "Loss of homotypic cell adhesion by epithelial-mesenchymal transition or mutation limits sensitivity to epidermal growth factor receptor inhibition," Mol Cancer Ther vol. 6(2):532-541(2007).

Capuzzo, F., "The Human Epidermal growth factor Receptor (HER) family:structure and function," Guide to Targeted Therapies: EGFR mutations in NSCLC, Chapter Two, Springer International Publishing Switzerland, 12 pages (2014) DOI 10.1007/978-3-319-03059-3_2.

Chan, C-M et al., "Inhibitory Effects of Resveratrol on PDGF-BB-Induced Retinal Pigment Epithelial Cell Migration via PDGFR beta, PI3K/Akt and MAPK Pathways," PLOS, vol. 9, Issue 2, 1-14 (2013).

Chan, L. et al., "A label-free photonic crystal biosensor imaging method for detection of cancer cell cytotoxicity and proliferation," Apoptosis, vol. 12:1061-1068 (2007).

Chigaev, A. et al., "Galphas-coupled receptor signaling actively down-regulates alpha4beta1-integrin affinity: A possible mechanism for cell de-adhesion," BMC Immunology, vol. 9(26):1-16 (2008).

Choi, B-K., et al., "ERBB3 (HER3) is a key sensor in the regulation of ERBB-mediated signaling in both low and high ERBB2 (HER2) expressing cancer cells," Cancer Medicine, vol. 1:28-38(2013).

Cragg, M. et al, "Unleashing the power of inhibitors of oncogenic kinases through BH3 mi-metics," Nature Reviews Cancer, vol. 9:321-326 (2009).

(56) References Cited

OTHER PUBLICATIONS

Cunningham, B. et al., "Label-free assays on the BIND system," Journal of Biomolecular Screening, vol. 9 (6):481-490). (2004).
Davis et al, "Comprehensive analysis of kinase inhibitor selectivity," Nature Biotechnology, vol. 29:(11)1046-1051 (2011).
De Alava, E. et al., "Neuregulin expression modulates clinical response to trastuzumab in patients with metastatic breast cancer," Journal of Clinical Oncology, vol. 25(19):2656-2663 (2007).
Ekert J. E., et al., "Three-Dimensional Lung Tumor Microenvironment Modulates Therapeutic Compound Responsiveness In Vitro—Implication for Drug Development," PLOS ONE, vol. 9 (3): 14 pages, e92248 (2014).
Endo, H. et al., "Spheroid Culture of Primary Lung Cancer Cells with Neuregulin 1 /HER3 Pathway Activation," Journal of Thoracic Oncology, vol. 8(2):131-139 (2013).
European Examination Report, EP Application No. 13731594.1, dated Jun. 28, 2016, 11 pages.
Extended European Search Report, European Application No. 18157442.7 dated Apr. 3, 2018, 10 pages.
Extended European Search Report, European Application No. 19180662.9, dated Dec. 9, 2019, 10 pages.
Extended European Search Report, European Application No. 20152262.0, dated Jul. 1, 2020, 15 pages.
Extended European Search Report, European Application No. 21159001.3, dated Jul. 14, 2021, 16 pages.
Fang, Ye, "Label-Free and Nonnovasive Biosensor Cellular Assays for Cell Adhesion," Journal of Adhesion Science and Technology, vol. 24:1011-1021 (2010).
Fountzilas, G. et al., "Evaluation of the prognostic role of centromere 17 gain and HER2/topoisomerase II alpha gene status and protein expression in patients with breast cancer treated with anthracycline-containing adjuvant chemotherapy: pooled analysis of two Hellenic Cooperative Oncology Group (HeCOG) phase III trials," BMC Cancer, vol. 13:163, 16 pages (2013).
Gharwan, H. et al. "Kinase inhibitors and monoclonal antibodies in oncology: clinical implications," Nature Reviews Clinical Oncology, vol. 13:209-227 (2016).
Gianni, L. et al., "Open-Label, Phase II, Multicenter, Randomized Study of the Efficacy and Safety of Two Dose Levels of Pertuzumab, a Human Epidermal Growth Factor Receptor 2 Dimerization Inhibitor, in Patients with Human Epidermal Growth Factor Receptor 2-Negative Metastatic Breast Cancer," Journal of Clinical Oncology, vol. 28 (7):1131-1137 (2010).
Gilad, I. et al., "Insulin-like-growth-factor-I (IGF-I) antagonizes apoptosis induced by serum deficiency and doxorubicin in neuronal cell culture," Growth Hormone & IGF Research, vol. 9: 458-464 (1999).
Guerra, Y., et al., "Lack of efficacy of adjuvant lapatinib in HER2-negative breast cancer (HER2-ve BC): Analysis of patients in the TEACH trial," 2013 ASCO Annual Meeting: Abstracts: Meeting Library, J. Clin. Oncol, vol. 31(Abstract 628), 2 pages, (2013). Retrieved from the Internet: URL:http://meetinglibrary.asco.org/content/115932-132[retrieved on Feb. 23, 2016].
Hassan, S. et al., "Model for Time Dependency of Cytotoxic Effect of CHS 828 in Vitro Suggests Two Different Mechanisms of Action," The Journal of Pharmacology and Experimental Therapeutics, vol. 299(3):1140-1147 (2001).
Hermanto U. et al., "ErbB2-overexpressing human mammary carcinoma cells display an increased requirement for the phosphatidylinositol 3-kinase signaling pathway in anchorage-independent growth", Oncogene, vol. 20 (51):7551-7562 (2001).
Holt, R.U. et al., "Human myeloma cells adhere to fibronectin in response to hepatocyte growth factor," Haematologica/The Hematology Journal, vol. 90(4):479-488. (2005).
Howe, L. et al., "Targeting the HER/EGFR/ErbB Family to Prevent Breast Cancer," Cancer Prev Res., vol. 4 (8):1149-1157 (2011).
Huang, Y et al., "A functional signal profiling test for identifying a subset of HER2-negative breast cancers with abnormally amplified HER2 signaling activity," OncoTarget, vol. 7(48):78577-78590 (2016) XP055474584, DOI:10.18632/oncotarget. 12480.
Huang, Y., et al., "Development of a test that measures real-time HER2 signaling function in live breast cancer cell lines and primary cells," BMC Cancer, vol. 17 (199):18 pages (2017), XP055474590, DOI: 10.1186/s12885-017-3181-0.
Hughes & Siemann, "Have Clinical Trials Properly Assessed c-Met Inhibitors?" Trends in Cancer, vol. 4:94-97 (2018).
Hynes, R., "Integrins: Bidirectional, Allosteric Signaling Machines," Cell, vol. 110:673-687 (2002).
International Preliminary Report on Patentability, PCT/US2013/045338, dated Dec. 16, 2014, 8 pages.
International Preliminary Report on Patentability, PCT/US2015/065584, dated Jun. 13, 2017, 10 pages.
International Preliminary Report on Patentability, PCT/US2018/022936, dated Sep. 24, 2019, 14 pages.
International Preliminary Report on Patentability, PCTUS2014/069980, dated Jun. 14, 2016, 10 pages.
International Search Report and Written Opinion, PCT/US2013/045338, dated Aug. 5, 2013, 12 pages.
International Search Report and Written Opinion, PCT/2015/065584, dated Mar. 7, 2016, 15 pages.
International Search Report and Written Opinion, PCT/US2018/022936, dated Jul. 19, 2018, 25 pages.
International Search Report and Written Opinion, PCTUS2014/069980, dated Jun. 26, 2015, 18 pages.
Invitation to Pay Additional Fees and, Where Applicable, Protest Fee, PCT/US2018/022936, dated May 24, 2018, 16 pages.
Jonker, DJ et al., "Cetuximab for the treatment of colorectal cancer," New England J of Med., vol. 357 (20):2040-2048 (2007).
Kanakry, C., et al., "Neuregulin-1 regulates cell adhesion via an ErbB2/phosphoinositide-3 kinase/Akt-dependent pathway: potential implications for schizophrenia and cancer," PLoS One, vol. 12:e1369: pp. 1-12 (2007).
Wallasch, C. et al., "Heregulin-dependent regulation of HER2/neu oncogenic signaling by heterodimerization with HER3.," EMBO Journal, vol. 14:4267-4275 (1995).
Xi, B. et al., "The application of cell-based label-free technology in drug di scovery," Biotechnology Journal, vol. 3 (4):484-495 (2008).
Xia, W. et al., "Anti-tumor activity of GW572016: a dual tyrosine kinase inhibitor blocks EGF activation of EGFR/erbB2 and downstream Erk1/2 and AKT pathways," Oncogene, vol. 21(41):6255-6263 (2002).
Yang, TY. et al., "A multiple reaction monitoring (MRM) method to detect Bcr-Abl kinase activity in CML using a peptide biosensor," PLoS One, vol. 8, e56627, 10 pages (2013).
Yuste, L. et al., "Activation of ErbB2 by Overexpression or by Transmembrane Neuregulin Results in Differential Signaling and Sensitivity to Herceptin," Cancer Res., vol. 65 (15): 6801-6810 (2005).
Zhao, W. et al, "Neuregulin 1 enhances cell adhesion molecule 11 expression in human glio-ma cells and promotes their migration as a function of malignancy," J Neuropathol Exp Neu-rol., vol. 72(3):244-255 (2013).
Kepp, O. et al., "Cell death assays for drug discovery," Nature Reviews, vol. 10: 221-237 (2011).
Kleinhans, R. et al., "Sensor-based cell and tissue screening for personalized cancer chemotherapy," Med Biol Eng Comput, vol. 50(2):117-126 (2012).
Konya, V. et al., "Endothelial E-type Prostanoid 4 Receptors Promote Barrier Function and Inhibit Neutrophil Trafficking," J. Allergy Clin. Immunol., vol. 131(2), No. 2:532-540 (2013).
Kwak, E. et al., "The Role of Irreversible HER Family Inhibition in the Treatment of Patients with Non-Small Cell Lung Cancer," The Oncologist, vol. 16:1498-1507 (2011).
Laing, L. et al., "Dynamic real-time signaling profiles of live primary cells characterize the response of PI3K and MAPK pathways in HER2+ breast cancer cells to attenuation with lapatinib: Tests of reproducibility of method," Journal of Clinical Oncology, vol. 32:15_suppl, e11597-e11597, 2014 American Society of Clinical Oncology (ASCO) (2014).
Laing, L. et al., "New method to measure functional HER2-driven signaling activity in primary tumor cells identifies HER2-negative breast cancers with abnormal HER2 signaling activity: New group

(56) References Cited

OTHER PUBLICATIONS of patients may benefit from anti-HER2 therapy," 2016 SABCS—San Antonio, TX, Cancer Res., vol. 77(4 Suppl): Abstract nr P6-07-14. (Abstract) (2017).

Laing, L. et al., "New method to measure functional HER2-driven signaling activity in primary tumor cells identifies HER2-negative breast cancers with abnormal HER2 signaling activity: New group of patients may benefit from anti-HER2 therapy," 2016 SABCS—San Antonio, TX, Cancer Res., vol. 77(4 Suppl): Abstract nr P6-07-14. (Poster Presentation) (2017).

Laing, L. et al., "Use of a functional signal profiling test to determine the prevalence of abnormal HER2-driven signaling activity in the HER2-negative breast cancer patient population: New patient group may benefit from anti-HER2 therapy," 2017 San Antonio Breast Cancer (SABCS), Abstract.

Laing, L. et al., "Use of a functional signal profiling test to determine the prevalence of abnormal HER2-driven signaling activity in the HER2-negative breast cancer patient population: New patient group may benefit from anti-HER2 therapy," 2017 San Antonio Breast Cancer (SABCS), Poster Presentation, 1 page.

Laing, L., "Live tumor cell functional analysis and a xenograft model find co-activated c-Met and ErbB signaling in HER2-negative breast cancer," 2018 American Society of Clinical Oncology (ASCO), J Clin Oncol., vol. 36 (suppl; abstr e24292) (2018) (Abstract only) 1 page.

Laing, L., "Profiling of signaling pathways in live tumor cells to assess drug mechanism of action: A method to predict drug efficacy in a patient [e11583]," American Society of Clinical Oncologists 2014, Journal of Clinical Oncology, vol. 32:15_suppl, e11583-e11588, (2014) American Society of Clinical Oncology (ASCO) Poster Presentation.

Laing, L., "The Pulse of Label Free Indicates the Technology is Alive and Beating," Drug Discovery, vol. 5: 24-30 (Oct./Nov. 2010).

Laing, L., et al., "Inhibition of abnormal HER2-driven signaling by two HER2 targeted antibody drugs tested ex vivo in live primary HER2-breast cancer cell samples and HER2+ cell lines," Abstract: #459, 2017 Miami Breast Cancer Conference—Miami, FL (Poster Presentation), 1 page.

Laing, L., et al., "Measuring functional HER2-driven signaling status ex vivo to predict response to HER2 therapy: Results from a mouse breast tumor xenograft study," 2017 American Society of Clinical Oncology (ASCO), Journal of Clinical Oncology, vol. 35_suppl, e23203 (Abstract) (2017).

Laing, L., et al., "Quantification of HER2-driven signaling (HER2S) inhibition of four different anti-HER2 drugs tested ex vivo in live primary HER2-negative breast cancer cell samples with abnormal HER2 signaling activity," Cancer Res., vol. 77(4 Suppl):Abstract nr P4-12-06. Poster Presentation (2017).

Lee, CY et al., "Neuregulin autocrine signaling promotes self-renewal of breast tumor-initiating cells by triggering HER2/HER3 activation," Cancer Res., vol. 74(1):341-52 (2014).

Levasseur, L. et al., "Modeling of the Time-Dependency of in Vitro Drug Cytotoxicity and Resistance," Cancer Research, vol. 58(24):5749-5761 (1998).

Liu Q. et al., "Impedance studies of bio-behavior and chemosensitivity of cancer cells by micro-electrode arrays," Biosensors and Bioelctronics, Elsevier BV, NL, vol. 24 (5):1305-1310 (2009).

Loum, E. et al., "Oncogramme, a new individualized tumor response testing method: application to colon cancer," Cytotechnology, vol. 62:381-388 (2010).

Lu, C. et al., "Effect of Epidermal Growth Factor Receptor Inhibitor on Development of Estrogen Receptor-Negative Mammary Tumors," Journal of the National Cancer Institute, vol. 95(24):1825-1833 (2003).

Mamounas, E., MD, MPH., et al., "A phase 2 study of neoadjuvant chemotherapy plus trastuzumab and pertuzumab in HER2-negative breast cancer patients with abnormal HER2-driven signaling transduction," (NCT03412643) NSABP Foundation and Orlando Health UF Cancer Center, Orlando, FL., Celcuity Inc., Minneapolis, MN, 2018 Miami Breast Cancer Conference—Miami, FL, (Poster Presentation) 1 page.

Matsuo, T. et al., "Analysis of the anti-tumor effect of cetuximab using protein kinetics and mouse xenograft models," BMC Research Notes, vol. 4(140):1-8.(2011).

McGuinness, R et al., "Impedance-based cellular assay technologies: recent advances, future promise," Current Opinion in Pharmacology, vol. 7(5):535-540 (2007).

Menendez, J.A., et al., Trastuzumab in Combination With Heregulin-Activated Her-2 (erbB-2) Triggers a Receptor-Enhanced Chemosensitivity Effect in the Absence of Her-2 Overexpression, Journal of Clinical Oncology, vol. 24:3735-3746 (2006).

Mestres, P. et al., "The Bionas technology for anticancer drug screening," Expert Opinion Drug Discovery, vol. 4 (7):785-797 (2009).

Moasser, M. "The oncogene HER2; Its signaling and transforming functions and its role in human cancer pathogenesis," Oncogene, vol. 26(45):6469-6487 (2007).

Montero, J. et al., "P-Rex1 participates in Neuregulin-ErbB signal transduction and its ex-pression correlates with patient outcome in breast cancer," Oncogene, vol. 30(9):1059-1071 (2011).

Morrison, S. et al., "Chimeric human antibody molecules: Mouse antigen-binding domains with human constant region domains," Proc. Natl. Acad. Sci. USA, vol. 81:6851-6855 (1984).

Muise-Helmericks, R. et al., "Cyclin D Expression Is Controlled Post-transcriptionally via a Phosphatidylinositol 3-Kinase/Akt-dependent Pathway," The Journal Of Biological Chemistry, vol. 273 (45):Issue of Nov. 6, 29864-29872 (1998).

Natarajan K. et al., "The Pim Kinase Inhibitor AZD1208 Enhances Apoptosis Induction By Clinically Active FLT3 Inhibitors in FLT3-ITD Acute Myeloid Leukemia Cells in Vitro and in Vivo through Synergistic Downregulation of Mcl-1 and of Bcl-XL," Blood, vol. 124(21): 3 pages (2014).

Niepel, M. et al., "Profiles of Basal and stimulated receptor signaling networks predict drug response in breast cancer lines," Science Signaling, vol. 6 (294): ra84, 12 pages (2013).

Ochs, R. et al., "The ChemoFx.@ Assay an Ex Vivo Cell Culture Assay for Predicting Anticancer Drug Responses," Methods in Molecular Medicine, vol. 110: Chemosensitivity: vol. 1: In Vitro Assays:155-172 (2005).

Ona, T. et al., "Advanced dynamic monitoring of cellular status using label-free and non-invasive cell-based sensing technology for the prediction of anticancer drug efficacy," Anal. Bioannal. Chem., vol. 398:2505-2533 (2010).

Otto, A. et al., "Microphysiological testing for chemosensitivity of living tumor cells with multiparametric microsensor chips," Cancer Detection and Prevention, vol. 27:291-296 (2003).

Otto, A. et al., "Multiparametric Sensor Chips for Chemosensitivity Testing of Sensitive and Resistant Tumor Cells," Recent Results in Cancer Research, vol. 161:39-47 (2003).

Park, J. et al., "Rationale for Biomarkers and Surrogate End Points in Mechanism-Driven Oncology Drug Development," Clinical Cancer Research, vol. 10:3885-3893 (2004).

Peters, M. et al., "Comparing Label-Free Biosensors for Pharmacological Screening with Cell-Based Functional Assays," Assay and Drug Development Technolgoies, vol. 8(2):219-227 (2010).

Ressler, J. et al , "New concepts for chip-supported multi-well-plates: realization of a 24-well-plate with integrated impedance-sensors for functional cellular screening applications and automated microscope aided cell-based assays.," Proceedings of the IEEE EMBS, vol. 3: 2074-2077 (2004).

Schuler, M. et al., "A phase II trial to assess efficacy and safety of afatinib in extensively pretreated patients with HER2-negative metastatic breast cancer," Breast Cancer Research and Treatment, vol. 134 (3):1149-1159 (2012).

Scott, C. et al., "Label-free whole-cell assays: expanding the scope of GPCR screening," Drug Discovery Today, vol. 15,(17/18): 704-716(2010).

Shamah, S et all., "Label-free cell-based assays using photonic crystal optical biosensors," Analyst, vol. 136:1090-1102 (2011).

(56) References Cited

OTHER PUBLICATIONS

Singer F. C. et al., "Predicting the efficacy of trastuzumab-based therapy in breast cancer: Current standards and future strategies," Biochimica et Biophysica Acta Reviews on Cancer, vol. 1786:105-113 (2008).

Solly, K. et al., "Application of real-time cell electronic sensing (RT-CES) technology to cell-based assays," Assay and Drug Development Technologies, vol. 2(4):363-372 (2004).

Sprague, L. et al., "Multiparametric Sensor-Chip Based Technology for Monitoring Metabolic Activity: A Proof-of- Principle Study with Live Tissue," Clin. Lab., vol. 52:375-384 (2006).

Struber, M. et al., "Low-potassium Dextran Solution Ameliorates reperfusion injury of the lung and protects surfactant function," The Journal of Thoracic and Cardiovascular Surgery, vol. 120(3):566-572 (2000).

Summons to Oral Proceedings, European Application No. 18157442. 7, dated Nov. 21, 2018, 11 pages.

Sun, C. et al. "Feedback and redundancy in receptor tyrosine kinase signaling: relevance to cancer therapies," Trends in Biochemical Sciences, vol. 39: 465-474 (2014).

Tan, M. et al., "Heregulin beta1-activated phosphatidylinositol 3-kinase enhances aggregation of MCF-7 breast cancer cells independent of extracellular signal-regulated kinase," Cancer Res., vol. 59(7):1620-1625 (1999).

Tyson, J. et al., "Dynamic modelling of estrogen signalling and cell fate in breast cancer cells," Nature Reviews, vol. 11(7):523-530 (2011).

Unger F. et al., "Prediction of Individual Response to Anticancer Therapy: Historical and Future Perspectives," Cell Mol. Life Science, vol. 72:729-757 (2015).

\* cited by examiner

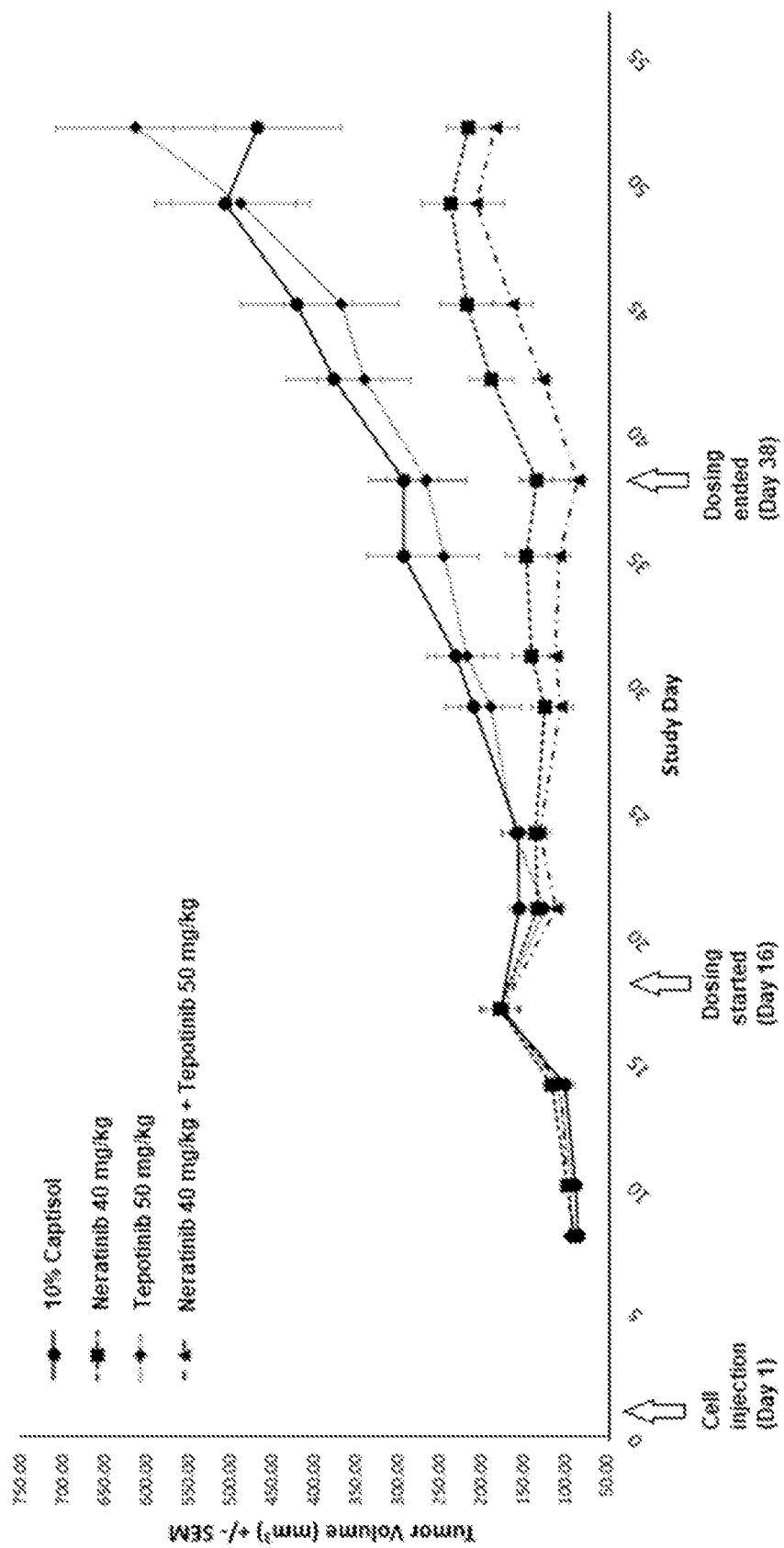

METHODS OF MEASURING SIGNALING PATHWAY ACTIVITY FOR SELECTION OF THERAPEUTIC AGENTS

RELATED APPLICATIONS

This application is a divisional of U.S. patent application Ser. No. 16/116,392, filed on Aug. 29, 2018, now U.S. Pat. No. 11,333,659, which is a continuation of International Application No. PCT/US2018/022936, filed on Mar. 16, 2018, which claims priority to, and the benefit of, U.S. Provisional Application No. 62/473,936, filed on Mar. 20, 2017, and U.S. Provisional Application No. 62/587,572, filed on Nov. 17, 2017. The entire contents of the aforementioned applications is incorporated herein by reference.

BACKGROUND OF THE INVENTION

Cancer is a significant medical problem, with estimates as high as approximately 40% of men and women in the United States being diagnosed with cancer at some point during their lifetime. While a variety of treatment options are available for different types of cancers, it is very clear that not every patient will respond to every treatment. Prescribing a treatment to a patient that turns out not to be therapeutically beneficial is detrimental for a number of reasons. For example, the patient is exposed to potentially harmful side effects of the treatment while not receiving any therapeutic benefit. Furthermore, the patient is delayed in receiving an alternative treatment that may be more therapeutically beneficial. Additionally, with medical costs being a growing concern, ineffective treatments are a financial burden. Thus, the ability to assess and accurately predict the likely benefit of a particular treatment for a particular patient before the patient is prescribed the treatment is of considerable interest. This interest has spawned a whole business field around personalized medicine (also referred to as precision medicine or stratified medicine), where each patient could potentially receive a therapeutic regimen customized for their disease. This ideal approach, however, has yet to be validated due primarily to significant shortcomings of the current prognostic toolset.

Extensive genetic data has been collected and analyzed for many different types of diseases, including a wide variety of cancers. At least two important facts have emerged from this process. First, a "disease" like breast cancer has been shown to be heterogeneous, in part because breast cancer in one individual can be completely different from the same cancer in another individual in genetic makeup and protein expression levels, thereby leading to the identification of genetic and protein "biomarkers" as potential indicators of responsiveness to a therapeutic agent. Second, however, it has been found that detection of the current leading genetic and protein biomarkers has poor predictive value for therapeutic responsiveness in the majority of cases.

For example, one response to the realization that each patient is different and that many times therapies fail to affect a positive response, has been the development of companion diagnostics. This type of diagnostic test is designed using contemporary biomarker detection tools to try to identify those patients that are more likely to respond to a particular drug. The test involves looking for increased gene number, gene mutation, or altered expression level of a particular gene. For example, many cancers today are diagnosed with the aid of tests to determine the presence of specific genetic mutations or over-expressed receptor proteins associated with the disease. However, most biomarker tests only provide indirect and inferential information about the disease and its underlying cause. Thus, the success rates for most of these tests at predicting significant therapeutic response are often much less than 50%.

This observation, that simply detecting the expression of a particular genetic or protein biomarker by a patient's cells is not a highly effective predictor of therapeutic responsiveness, demonstrates that more effective means for selecting therapeutic treatment regimens are needed. In particular, physicians currently lack the knowledge of how a specific patient's cells are functioning, or more appropriately malfunctioning, and thus how they will respond to one of the many therapeutics that are available for treating the disease. They may know that an aberrant gene is present but do not know how that affects the disease course in a specific patient. They may know specifically how a drug is supposed to act but not why a particular patient may be unresponsive or resistant to that drug activity. Accordingly, patients need better identification of their particular disease cause at a functional level and better-informed decision-making for an effective therapeutic course.

One approach that has been taken to address how a specific patient's cells are functioning, or malfunctioning, has been to examine the activity of a signaling pathway in the patient's cells, through assessment of a change in a physiological response parameter, such as cell adhesion, that indicates activity, or lack thereof, of the signaling pathway. This approach has allowed for accurate prediction of the effectiveness of targeted therapeutic agents that selectively affect the signaling pathway being examined (as described in PCT Publication WO 2013/188500).

There remains a need to provide alternative and better prognostic indicators for the effectiveness of therapeutic agents, particularly targeted therapeutic agents, for an individual.

SUMMARY OF THE INVENTION

This invention provides methods for treating patients with one or more targeted therapeutic agents wherein the selection of one or more targeted therapeutic agents uses a method that provides in depth information about the functional activity of one or more signaling pathways in the patient's cells to thereby allow for improved selection of the most appropriate targeted therapeutic agent(s) for treatment of the patient.

In one aspect of the invention, the method used to select the targeted therapeutic agent for treatment of a cancer patient involves evaluating the functional activity of multiple (two or more) signaling pathways in the patient's cancer cells. The functional activity of multiple signaling pathways can be evaluated in the patient's cancer cells in parallel (i.e., by assessing different pathways individually in different portions of the same cell sample in parallel) or simultaneously (i.e., by assessing different pathways simultaneously within the same cells) or by a combination of parallel and simultaneous analysis, as described herein.

This approach of evaluating multiple signaling pathways allows for identification of the specific most active disease signaling pathway(s) and unexpected synergies between pathways' activation or therapeutic intervention in a patient's tumor, by individually or simultaneously assessing the activity of several different signaling pathways in the tumor and comparing the results. The patient is then treated with one or more targeted therapeutic agents that affect the signaling pathway(s) with the highest level of activity. This approach improves on methods that assess only a single signaling pathway in the patient's cells. When only a single pathway is evaluated and its activity is found to be normal, the identification of the aberrant signaling pathway driving the patient's tumor remains unknown. In addition, if the single pathway evaluated is found to be aberrant, a targeted therapeutic that affects this pathway then would be selected for treatment. However, the aberrant activity of this single signaling pathway does not provide sufficient information on whether this aberrant signaling pathway is most important and in fact driving the disease process (e.g., growth of the tumor) in relation to potentially more or equally aberrant signaling. Thus, by testing only a single pathway for a patient, a targeted therapeutic could be selected that still may be ineffective in attenuating the disease process or that may be less effective than a targeted therapeutic that affects a different pathway. Furthermore, the aberrant activity in one pathway may be a consequence of aberrant signaling in a second pathway and or the pathways may be linked synergistically or by crosstalk or by other biochemical mechanisms such that only by testing multiple pathways may the most accurate targeted therapy(s) be determined for an individual patient. In the methods of the present disclosure, by individually or simultaneously assessing multiple signaling pathways in the same sample of a patient's cancer cells, the signaling pathways driving the disease and with the highest levels of activity can be identified, thereby allowing for selection of a therapeutic agent(s) that targets the signaling pathway(s) in the patient's cancer cells that have the highest level of activity or the selection of two or more therapeutic agents that target the signaling pathways in the patient's cancer cells that have the highest levels of activity.

Furthermore, since the selection methods of the invention determine the level of activity of signaling pathways in a patient's cells, not simply whether a particular therapeutic agent is active or not, the selection methods of the invention thereby allow for selection for therapeutic use of one or more targeted therapeutic agents within a panel of agents that affect the same signaling pathway, not simply the specific therapeutic agent that was tested in the method. Thus, the selection methods of the invention provide for identification of a larger panel of potential therapeutic agents for selection than testing of single agents alone. For example, through use of the selection methods of the invention, it can be determined which signaling pathway is driving the disease in a patient's cancer cell by using a targeted therapeutic agent that affects the same signaling pathway (as described in detail herein). The final selection of targeted therapeutic agent(s) to be used therapeutically may be the same or a different agent than the agent(s) tested in vitro that affects that same signaling pathway that has been determined to be driving the patient's disease.

Accordingly, in one aspect, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample with at least two sets of paired agents, each set comprised of a first agent that is a targeted therapeutic and a second agent that is an activator that is known to selectively affect the same signaling pathway the first agent is intended to address, wherein each set of paired agents affects a different signaling pathway, so as to upregulate or downregulate the signaling pathway as measured by an effect on cell adhesion or attachment, to produce a sample contacted with at least two sets of paired agents;

continuously measuring cell adhesion or attachment of the viable cancer cells in the sample contacted with each set of paired agents, relative to a sample of viable cancer cells obtained from the subject that is contacted with each of the first agents or each of the second agents alone;

determining by mathematical analysis of the continuous measurements an output value for each set of paired agents that characterizes whether a change in cell adhesion or attachment has occurred in the sample contacted with the set of paired agents, as compared to the sample contacted with the first agents or the second agents alone; and administering to the subject at least one targeted therapeutic that affects the same signaling pathway as the first agent from the set of paired agents determined to have the highest output value of all sets tested, indicating the administered targeted therapeutic agent is more therapeutically active in the cell signaling pathway of the subject's cancer cells than the targeted therapeutic(s) from the set(s) of paired agents with lower output value.

In another embodiment, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample simultaneously with at least at least two sets of paired agents, each set comprised of a first agent that is at least one targeted therapeutic and a second agent that is at least one activator that is known to selectively affect the same signaling pathway the first agent is intended to address, wherein each set of paired agents affects a different signaling pathway, so as to upregulate or downregulate the signaling pathway as measured by an effect on cell adhesion or attachment, to produce a sample contacted with at least two sets of paired agents;

continuously measuring cell adhesion or attachment of the viable cancer cells in the sample contacted with each set of paired agents, relative to a sample of viable cancer cells obtained from the subject that is contacted with each of the first agents or each of the second agents alone;

determining by mathematical analysis of the continuous measurements an output value for each set of paired agents that characterizes whether a change in cell adhesion or attachment has occurred in the sample contacted with the set of paired agents, as compared to the sample contacted with the first agents or the second agents alone; and administering to the subject at least one targeted therapeutic that affects the same signaling pathway as the first agent from the set of paired agents determined to have the highest output value of all sets tested, indicating the administered targeted therapeutic agent is more therapeutically active in the cell signaling pathway of the subject's cancer cells than the targeted therapeutic(s) from the set(s) of paired agents with lower output value.

Thus, the paired agents that result in the highest output value of all sets tested indicates which signaling pathway is driving the subject's cancer cells (i.e., which pathway is most active with respect to the disease process) as compared to signaling pathway activity of paired agents with lower output value. The targeted therapeutic that is then chosen for administration to the subject may be either the first agent from the paired agents that resulted in the highest output value (i.e., the targeted therapeutic that was used as the first agent in the in vitro testing can then be selected for administration to the subject) or a different agent than the first agent from the paired agents that resulted in the highest output value yet is a targeted therapeutic that targets (e.g., selectively affects) the same signaling pathway as the paired agents that resulted in the highest output value.

In one embodiment, the sample is contacted with more than two sets of paired agents, such as ten or more sets of paired agents, wherein each set of paired agents affects a different signaling pathway. Suitable signaling pathways and sets of paired agents and signaling pathways are disclosed herein (e.g., Tables 2, 12, 13).

In one embodiment, at least one set of paired agents selectively affects a HER family signaling pathway and at least one set of paired agents selectively affects a signaling pathway other than the HER family signaling pathway. For example, in various embodiments, at least one set of paired agents selectively affects a HER family signaling pathway and at least one set of paired agents selectively affects either the c-Met/HGF signaling pathway, the estrogen receptor (ER) signaling pathway, the FGFR signaling pathway or the PDGFR signaling pathway.

In one embodiment, at least one set of paired agents selectively affects the estrogen receptor (ER) signaling pathway and at least one set of paired agents selectively affects a signaling pathway other than the ER signaling pathway. For example, in one embodiment, at least one set of paired agents selectively affects the ER signaling pathway and at least one set of paired agents selectively affects the IGFR signaling pathway.

In one embodiment, at least two targeted therapeutics are administered to the subject: (i) the targeted therapeutic from the set of paired agents determined to have the highest output value of all sets tested and (ii) at least one additional targeted therapeutic from the set of paired agents determined to have an output value indicating the targeted therapeutic is therapeutically active in the cell signaling pathway of the subject's cancer cells. In one embodiment, the at least one additional targeted therapeutic is determined to change signaling activity initiated by an activating agent more than 50% indicating the targeted therapeutic is therapeutically active in the cell signaling pathway of the subject's cancer cells. Again, in various embodiments, the targeted therapeutics that are administered to the subject may be the same targeted therapeutics that are used in the paired sets of agents tested in vitro or, alternatively, different targeted therapeutics than were tested in vitro but that target (e.g., selectively affect) the same signaling pathway as the targeted therapeutics that were tested in vitro.

Suitable targeted therapeutics and activators for use in each set of paired agents, as well as suitable signaling pathways, are described in detail herein.

In one embodiment, cell adhesion or attachment is measured using an impedance biosensor or an optical biosensor.

In one embodiment, the cancer is selected from the group consisting of breast cancer, lung cancer, colorectal cancer, bladder cancer, kidney cancer, ovarian cancer and leukemia.

In one embodiment, the sample of viable cancer cells is cultured in a media comprising growth factors and free of serum. In one embodiment, the sample of viable cancer cells is also cultured in a media comprising an anti-apoptotic agent and free of serum.

In another aspect of the invention, the method used to select the targeted therapeutic agent for treatment of a cancer patient involves identifying a signaling pathway in a patient's cells that is ultra-sensitive, and then treating the patient with a targeted therapeutic agent that affects this ultra-sensitive signaling pathway. An ultra-sensitive pathway is one in which only a very low level of cellular input, such as a signaling pathway activator (e.g., a receptor ligand) is capable of causing a very high level of pathway activation or responsiveness (e.g., 90% cellular output). It has been discovered that a signaling pathway in a patient's cancer cells that is ultra-sensitive is likely to be involved in driving the disease process (e.g., tumor growth), even if there are additional aberrant signaling pathways in the cancer cells. Thus, identifying a signaling pathway in a patient's cancer calls that is ultra-sensitive and then selecting a targeted therapeutic agent that targets this signaling pathway is an effective means for selecting therapeutically effective treatment regimens.

Accordingly, in another aspect, the invention pertains to a method of treating a human subject diagnosed with cancer, the method comprising:
administering to the subject at least one targeted therapeutic that selectively affects an abnormally active signaling pathway in the subject's cancer cells, wherein the signaling pathway has been determined to be abnormally active in the subject's cancer cells by a method comprising:
culturing a sample comprising viable cancer cells obtained from the subject;
contacting the sample with an activator that is known to selectively affect a signaling pathway, so as to upregulate or downregulate the signaling pathway as measured by an effect on cell adhesion or attachment, wherein a portion of the sample is contacted with a higher concentration of the activator and a portion of the sample is contacted with a lower concentration of the activator;
continuously measuring cell adhesion or attachment of the viable cancer cells in the portion of the sample contacted with a higher concentration of the activator, relative to the portion of the sample contacted with the lower concentration of the activator;
determining by mathematical analysis of the continuous measurements the sensitivity of the signaling pathway to the activator; and
administering to the subject at least one targeted therapeutic that selectively affects the same signaling pathway the activator affects when the signaling pathway is ultra-sensitive to the activator, indicating the signaling pathway is abnormally active in the subject's cancer cells.

In one embodiment, the method comprises continuously measuring cell adhesion or attachment of the viable cancer cells in the portion of the sample contacted with a higher concentration of the activator, relative to the portion of the sample contacted with a lower concentration of the activator, and relative to a portion of the sample that has not been contacted with the activator;
determining by mathematical analysis of the continuous measurements sensitivity of the sample to the activator and an output value for the activator that characterizes whether a change in cell adhesion or attachment has occurred in the portions of the sample contacted with the activator, as compared to the portion of the sample not contacted with the activator; and administering to the subject at least one targeted therapeutic that selectively affects the same signaling pathway the activator affects when the signaling pathway is ultra-sensitive to the activator, indicating the signaling pathway is abnormally active in the subject's cancer cells or when the output value for the activator is greater than a pre-determined cut-off value.

In one embodiment, the higher concentration of the activator is EC90 and the lower concentration of the activator is EC10. In one embodiment, an EC90:EC10 ratio of less than 81 indicates that the signaling pathway is ultra-sensitive to the activator.

In one embodiment, sensitivity of the signaling pathway to the activator is determined using the Hill equation to determine a Hill Coefficient. In one embodiment, a Hill Coefficient value of greater than one indicates that the signaling pathway is ultra-sensitive to the activator.

Various suitable signaling pathways, activators and targeted therapeutics are described in detail herein.

In one embodiment, cell adhesion or attachment is measured using an impedance biosensor or an optical biosensor.

In one embodiment, the cancer is selected from the group consisting of breast cancer, lung cancer, colorectal cancer, bladder cancer, kidney cancer, ovarian cancer and leukemia.

In one embodiment, the sample of viable cancer cells is cultured in a media comprising growth factors and free of serum. In one embodiment, the sample of viable cancer cells is also cultured in a media comprising an anti-apoptotic agent and free of serum.

In another aspect of the invention, the method used to select the targeted therapeutic for treatment of a cancer patient involves first determining a cut-off value for the activity of a specific signaling pathway that corresponds to a particular level of activity (e.g., average, mean, upper quartile or the like) for the same signaling pathway of a group of patients (e.g., 5, 10, 20, 40, 50 or more) whose signaling pathway is ultra-sensitive. Patients with a level of signaling pathway activity that is above the cut-off value would be treated with a targeted therapeutic agent that affects the same signaling pathway that has activity above the cut-off value.

In another aspect of the invention, the method used to select the targeted therapeutic agent for treatment of a cancer patient involves evaluating the amount of activity simultaneously initiated in a patient's cells by at least two signaling pathway activators that a single targeted therapeutic agent can inhibit. Since activity of one signaling pathway may be driven by upstream, downstream, lateral, crosstalk, feedback, or feedforward activity from another pathway initiated by more than one cell surface receptor and said signals passing through a shared pathway node, it is advantageous to evaluate the antagonist effect of a therapy targeting such a shared pathway node or combination of nodes. This approach allows for measurement of the affect a therapeutic targeting a shared downstream pathway node (e.g. AKT, PI3K, MEK, ERK, mTOR) has on signaling pathway activity downstream of multiple cell surface receptors. By evaluating the simultaneous effect of two or more signaling pathway activators in a patient's cells downstream of the cell surface receptors, this approach improves on methods that evaluate the effect of a pair of signaling pathway activator and targeted therapeutic agents have in the patient's cells. Additionally, the present invention includes therapeutic agents that are known and can be found that bind to and regulate multiple nodes or targets (e.g. neratinib, duligotuzumab, crizotinib, pazopanib, pictilisib). The present invention is ideal in identifying this type of combination therapeutic and matching to patients most likely to receive benefit from them.

Accordingly, in another aspect, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample with at least one triplet set of agents, each triplet set comprised of a first agent targeted therapeutic and at least two second agent activators that are known to selectively affect the same signaling pathway the targeted therapeutic is intended to address, so as to upregulate or downregulate the signaling pathway as measured by an effect on cell adhesion or attachment, to produce a sample contacted with at least one triplet set of agents;

continuously measuring cell adhesion or attachment of the viable cancer cells in the sample contacted with the at least one triplet set of agents, relative to a sample of viable cancer cells obtained from the subject that is contacted with the first agent targeted therapeutic or each of the second agent activators alone;

determining by mathematical analysis of the continuous measurements an output value for the at least one triplet set of agents that characterizes whether a change in cell adhesion or attachment has occurred in the sample contacted with the triplet set of agents, as compared to the sample contacted with the first agent targeted therapeutic or the second agent activators alone; and administering to the subject at least one targeted therapeutic that affects the same signaling pathway as the first agent targeted therapeutic from the triplet set of agents when the output value is greater than a pre-determined cut-off value indicating the targeted therapeutic is therapeutically active in the cell signaling pathway of the subject's cancer cells.

In one embodiment, the first agent targeted therapeutic is determined to have an output value percentage greater than 50% indicating the signaling pathway affected by the first agent targeted therapeutic is active in the subject's cancer cells.

In another embodiment, the sample is contacted with at least two first agent targeted therapeutics that are known to selectively affect the same signaling pathways the two or more second agent activators address.

Various suitable signaling pathways, activators and targeted therapeutics are described in detail herein.

In one embodiment, cell adhesion or attachment is measured using an impedance biosensor or an optical biosensor.

In one embodiment, the cancer is selected from the group consisting of breast cancer, lung cancer, colorectal cancer, bladder cancer, kidney cancer, ovarian cancer and leukemia.

In one embodiment, the sample of viable cancer cells is cultured in a media comprising growth factors and free of serum. In one embodiment, the sample of viable cancer cells is also cultured in a media comprising an anti-apoptotic agent and free of serum.

In another aspect of the invention, the method used to select the targeted therapeutic agent for treatment of a cancer patient involves evaluating the amount of activity initiated in a patient's cells by one signaling pathway activator and inhibited by a targeted therapeutic agent that does not directly target the same approximate binding site as the activators. Since two or more signaling pathways may be interconnected with multiple points of convergence, crosstalk and feedback loops, a targeted therapeutic designed to inhibit pathway activity initiated at the activator binding site (e.g. cell surface receptor) may not be the most effective way of inhibiting the signaling pathway activity. In cases where signaling pathway activity initiated by an activator agent cannot be inhibited by a matching signaling pathway inhibitor directly targeting the same approximate binding site as the activator, a therapy targeting a different binding site than the binding site of the activator may be able to inhibit the initiated signaling pathway activity. This approach allows for measurement of the affect a therapeutic targeting a binding site downstream (e.g. AKT, PI3K, MEK, ERK, mTOR), upstream (e.g RAS, RAF), or lateral (e.g. Hedgehog, Notch, Wnt, c-MET, ALK, AXL, FGFR) to the binding site of the activator agent has on signaling pathway activity initiated by the activator agent. By evaluating the effect of a signaling pathway inhibitor downstream, upstream, or lateral to the activation binding site of an activator agent in a patient's cells, this approach improves on methods that evaluate the effect of a pair of signaling pathway activator and targeted therapeutic agents have at the same approximate binding site in the patient's cells. Additionally, the present invention includes therapeutic agents that are known and can be found that bind to and regulate multiple nodes or targets. Thus, treating a patient with a targeted therapeutic that binds to different binding site than an activator agent can lead to superior efficacy and better clinical outcomes.

Accordingly, in another aspect, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample with (i) a first agent activator that affects a signaling pathway, wherein the activator has an activation binding site, and (ii) a second agent targeted therapeutic agent that affects the same signaling pathway as the activator but at a binding site downstream, upstream or lateral to the activation binding site, so as to upregulate or downregulate the signaling pathway as measured by an effect on cell adhesion or attachment, to produce a sample contacted with the first agent and the second agent;

continuously measuring cell adhesion or attachment of the viable cancer cells in the sample contacted with the first agent and second agent, relative to a sample of viable cancer cells obtained from the subject that is contacted with the first agent or the second agent alone;

determining by mathematical analysis of the continuous measurements an output value that characterizes whether a change in cell adhesion or attachment has occurred in the sample contacted with both the first agent and the second agent, as compared to the sample contacted with the first agent or the second agent alone; and administering to the subject at least one targeted therapeutic that affects the same signaling pathway that the second agent targeted therapeutic affects, wherein the output value that characterizes the change in cell adhesion or attachment is equal to or greater than a cut-off value indicating the signaling pathway is active in the subject's cancer cells.

In one embodiment, the targeted therapeutic that is administered to the subject is the same second agent targeted therapeutic that is tested in vitro. Alternatively, in another embodiment, the targeted therapeutic that is administered to the subject is different than the second agent targeted therapeutic that is tested in vitro but is a targeted therapeutic that affects the same signaling pathway as the second agent at the same point in the signaling pathway as the tested second agent targeted therapeutic (i.e., downstream, upstream or lateral to the activation binding site of the first agent activator).

Various suitable signaling pathways, activators and targeted therapeutics are described in detail herein.

In one embodiment, cell adhesion or attachment is measured using an impedance biosensor or an optical biosensor.

In one embodiment, the cancer is selected from the group consisting of breast cancer, lung cancer, colorectal cancer, bladder cancer, kidney cancer, ovarian cancer and leukemia.

In one embodiment, the sample of viable cancer cells is cultured in a media comprising growth factors and free of serum. In one embodiment, the sample of viable cancer cells is also cultured in a media comprising an anti-apoptotic agent and free of serum.

In yet another aspect of the invention, the method used to select the targeted therapeutic agent for treatment of a cancer patient involves evaluating the amount of activity initiated in a patient's cells by two or more signaling pathway activators and inhibited by a targeted therapeutic agent that does not directly target the same approximate binding sites as either activator. Since two or more signaling pathways may be interconnected with multiple points of convergence, crosstalk and feedback loops, targeted therapeutics designed to inhibit pathway activity initiated at each of the activator binding sites (e.g. different cell surface receptors) may not be the most effective way of inhibiting the signaling pathway activity. In cases where signaling pathway activity initiated by two or more activator agents cannot be inhibited by two matching signaling pathway inhibitors directly targeting the same approximate binding sites as the activators, a therapy targeting a different binding site than the binding site of either activator may be able to inhibit the initiated signaling pathway activity. This approach allows for measurement of the affect a therapeutic targeting a binding site downstream (e.g. AKT, PI3K, MEK, ERK, mTOR), upstream (e.g RAS, RAF), or lateral (e.g. Hedgehog, Notch, Wnt, c-MET, ALK, AXL, FGFR) to the binding sites of the activator agents has on signaling pathway activity initiated by the activator agents. By evaluating the effect of a signaling pathway inhibitor downstream, upstream, or lateral to the activation binding site of two or more activator agents in a patient's cells, this approach improves on methods that evaluate the effect of a pair of signaling pathway activators and targeted therapeutic agents each have at the same approximate binding sites in the patient's cells. Additionally, the present invention includes therapeutic agents that are known and can be found that bind to and regulate multiple nodes or targets. Thus, treating a patient with a targeted therapeutic that binds to a different binding site than an activator agent can lead to superior efficacy and better clinical outcomes.

Accordingly, in another aspect, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample with (i) two or more first agent activator that affects a signaling pathway, wherein each activator has an activation binding site, and (ii) a second agent targeted therapeutic agent that affects the same signaling pathway as the two or more first agent activators but at a binding site downstream, upstream or lateral to the activation binding sites of the activators, so as to upregulate or downregulate the signaling pathway as measured by an effect on cell adhesion or attachment, to produce a sample contacted with the first agents and the second agent;

continuously measuring cell adhesion or attachment of the viable cancer cells in the sample contacted with the first agents and second agent, relative to a sample of viable cancer cells obtained from the subject that is contacted with the first agents or the second agent alone;

determining by mathematical analysis of the continuous measurements an output value that characterizes whether a change in cell adhesion or attachment has occurred in the sample contacted with both the first agents and the second agent, as compared to the sample contacted with the first agents or the second agent alone; and administering to the subject at least one targeted therapeutic that affects the same signaling pathway that the second agent targeted therapeutic affects, wherein the output value that characterizes the change in cell adhesion or attachment is equal to or greater than a cut-off value indicating the signaling pathway is active in the subject's cancer cells.

In one embodiment, the targeted therapeutic that is administered to the subject is the same second agent targeted therapeutic that is tested in vitro. Alternatively, in another embodiment, the targeted therapeutic that is administered to the subject is different than the second agent targeted therapeutic that is tested in vitro but is a targeted therapeutic that affects the same signaling pathway as the second agent at the same point in the signaling pathway as the tested second agent targeted therapeutic (i.e., downstream, upstream or lateral to the activation binding sites of the first agent activators).

Various suitable signaling pathways, activators and targeted therapeutics are described in detail herein.

In one embodiment, cell adhesion or attachment is measured using an impedance biosensor or an optical biosensor.

In one embodiment, the cancer is selected from the group consisting of breast cancer, lung cancer, colorectal cancer, bladder cancer, kidney cancer, ovarian cancer and leukemia.

In one embodiment, the sample of viable cancer cells is cultured in a media comprising growth factors and free of serum. In one embodiment, the sample of viable cancer cells is also cultured in a media comprising an anti-apoptotic agent and free of serum.

In yet another aspect of the invention, the method used to select the targeted therapeutic agent for treatment of a cancer patient involves evaluating the functional activity of one signaling pathway in the patient's cancer cells using a set of agents containing one activating agent and two or more therapeutic agents, where the activating agent and one of the therapeutic agents bind to the same signaling pathway and the other therapeutic agent(s) binds to a different signaling pathway or cellular location. Accordingly, in another aspect, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample simultaneously with at least one triplet set of agents, each triplet set comprised of a first agent targeted therapeutic, a second agent activator that is known to selectively affect the same signaling pathway the first agent is intended to address and a third agent targeted therapeutic that affects a different signaling pathway than the first agent or a different location within the signaling pathway that the first agent affects, so as to upregulate or downregulate the signaling pathway that the first agent affects as measured by an effect on cell adhesion or attachment, to produce a sample contacted with at least one triplet set of agents;

continuously measuring cell adhesion or attachment of the viable cancer cells in the sample contacted with the at least one triplet set of agents, relative to a sample of viable cancer cells obtained from the subject that is contacted with the first agent targeted therapeutic alone, the second agent activator alone or the third agent targeted therapeutic alone;

determining by mathematical analysis of the continuous measurements an output value for the at least one triplet set of agents that characterizes whether a change in cell adhesion or attachment has occurred in the sample contacted with the triplet set of agents, as compared to the sample contacted with the first agent targeted therapeutic alone, the second agent activator alone or the third agent targeted therapeutic alone; and administering to the subject at least one targeted therapeutic that affects the same signaling pathway as the first agent targeted therapeutic from the triplet set of agents when the output value is greater than a pre-determined cut-off value indicating the first agent targeted therapeutic agent is therapeutically active in the cell signaling pathway of the subject's cancer cells.

In one embodiment, the at least one targeted therapeutic that is administered to the subject is the first agent targeted therapeutic, the third agent targeted therapeutic or both the first and third agent targeted therapeutics. In another embodiment, the at least one targeted therapeutic that is administered to the subject is different than the first agent and/or third agent targeted therapeutic but targets the same signaling pathway as said first agent or third agent targeted therapeutic.

Various suitable signaling pathways, activators and targeted therapeutics are described in detail herein.

In one embodiment, cell adhesion or attachment is measured using an impedance biosensor or an optical biosensor.

In one embodiment, the cancer is selected from the group consisting of breast cancer, lung cancer, colorectal cancer, bladder cancer, kidney cancer, ovarian cancer and leukemia.

In one embodiment, the sample of viable cancer cells is cultured in a media comprising growth factors and free of serum. In one embodiment, the sample of viable cancer cells is also cultured in a media comprising an anti-apoptotic agent and free of serum.

BRIEF DESCRIPTION OF THE DRAWING

FIG. 1 is a graph showing average tumor volumes in mice xenografted with C21 tumor cells and treated with either a vehicle control, neratinib alone, tepotinib alone or neratinib and tepotinib in combination.

DETAILED DESCRIPTION OF THE INVENTION

The invention provides for the ability to probe in detail the signaling pathway activity within a cell (e.g. a cancer cell) to thereby determine, for example, which signaling pathways are normally active or abnormally active, which signaling pathway from among a group of tested pathways is most active and/or which signaling pathways are ultrasensitive. Since the methods of the invention provide for detailed information on the activity of signaling pathways, they allow for the selection and therapeutic use (i.e., administration) of a wide variety of targeted therapeutics. Since the methods are assessing the status of the signaling pathway itself, it is not necessary that the targeted therapeutic that is selected for therapeutic use be the same targeted therapeutic that is tested in the in vitro method. Rather, a targeted therapeutic that targets (e.g., selectively affects) the same signaling pathway as the tested targeted therapeutic (e.g., at the same or a different point within the signaling pathway) also can be selected for therapeutic use. Moreover, since signaling pathways can be interconnected with multiple points of convergence, cross-talk and feedback loops, and unexpected synergies between pathways, the methods of the invention allow for screening of targeted therapeutics and activator agents that affect the same signaling pathway but at different points or binding sites within the pathway, to thereby determine the most appropriate point or binding site within a signaling pathway to target for therapeutic intervention with a targeted therapeutic.

In order that the present invention may be more readily understood, certain terms are first defined. Additional definitions are set forth throughout the detailed description.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference. The following terms, as used herein, are intended to have the following definitions.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5).

The terms "activator," "activate", "activation", "perturbant," "perturb," and "perturbation" when used in conjunction with reference to cells refer to the specific subject or activity of physiologic manipulation of a cell using reagents, approved drugs, experimental compounds and drug like molecules and experimental drugs in development, organic molecules, growth factors, signaling factors, biochemicals, nucleic acids, cytokines, chemokines, or proteins that have an effect on cells well known to those practiced in the art. The manipulation refers to any modulation of cellular physiologic activity and may include but not be limited to up or down-regulation. The activator agent or perturbant may additionally include but are not limited to any of the following single agents or combinations thereof: a specific growth factor that includes members and combinations of members but is not limited to these members or combinations of members from the following list: vascular endothelial growth factors, phosphatidyl inositol, epidermal growth factors and factors with the EGF peptide sequence, hepatocyte growth factors, m-CSF, RANK ligand, Tumor Necrosis Factors (TNF-α), insulin growth factors, transforming growth factors, hepatocyte growth factors, neuregulins or neural regulins, heregulin and factors associated with the ErbB family of receptors, estrogen and its hormonal precursors and degradation products (Ex. DHEA, Estrone, androstenedione), progesterone, testosterone, folate, adenosine triphosphate, AMP, cyclic AMP, and FAS Ligand, Platelet derived growth factors (PDGF), or other agents of cellular pathway or signaling perturbation such as the subject's plasma or serum or supernatant fractions derived from patient cells (especially fibroblasts and epithelial), Na+, K+, Mg+, Cl−, Ca+2, glucose, glutamine, histidine, mannitol, and tryptophan, antibiotics (rapamycin), essential and non-essential amino acids, vitamins, other organic compounds, trace minerals and inorganic salts, sodium selenite, serum, cell extracts, fractionated cell extracts or fractionated serum, extracellular signaling factors, intracellular signaling factors, insulin, transferrin, hydrocortisone, ethanolamine, phosphophorylethanoloamine, triidothyronine, sodium pyruvate, mitogens, oxytocin, isoproterenol, L-glutamine.

The term "adhesion" can encompass processes involving any number of molecules responsible for connecting a cell to an ECM or to other cells directly, indirectly, and or indirectly by pathway communication. For example, integrins are responsible for cytoskeletal organization, cellular motility, regulation of the cell cycle, regulation of cellular of integrin affinity, attachment of cells to viruses, attachment of cells to other cells or ECM. Integrins are also responsible for signal transduction, a process whereby the cell transforms one kind of signal or stimulus into another—intra- and inter-cellularly. Integrins can transduce information from the ECM to the cell and information from the cell to other cells (e.g., via integrins on the other cells) or to the ECM. The combination of the α- and β-subunits determines the ligand specificity of the integrin. Many integrins have binding specificities for the same ligands and it is the combination of the integrin expression/activation pattern and the availability of ligand that specifies the interactions in vivo. Adhesion can change in density within a cell area or area of a population of cells. Adhesion can change in quantity within a cell or population of cells. Adhesion can change in quality by specificity or protein types involved in the adhesion process. Adhesion can change in polarity.

The term "assay" or "assaying" refers to an analysis to determine, for example, the presence, absence, quantity, extent, kinetics, dynamics, or type of a target, such as a cell's optical or bioimpedance response upon activation with exogenous stimuli (e.g., therapeutic agent or ligand).

The terms "attach," or "attachment," refer to, for example, a surface modifier substance, a cell, a ligand candidate compound, and like entities of the disclosure, connected to a surface, such as by physical absorption, chemical bonding, chemical attraction, and like processes, or combinations thereof. Particularly, "cell attachment," "cell adhesion," or "cell sample attachment" refer to the binding of cells together or interacting to a surface, such as by culturing, or interacting with a cell anchoring material, or the like.

The term "attachment pattern" refers to observable traits or characteristics of a cell or cell sample's connection to a surface. An attachment pattern can be quantitative, e.g., number of attachment sites. An attachment pattern can also be qualitative, e.g., preferred molecular site of attachment to an extracellular matrix.

The term "Cell Attachment Signal (CAS)" refers to a quantitative measurement of cell attachment generated by cells when placed in the well of a microplate and analyzed with an impedance biosensor. Typically, a cell's CAS in the absence of any agents can be compared to the cell's CAS in the presence of an activator agent alone that affects a particular signaling pathway and/or to the cell's CAS in the presence of an activator agent that affects a particular signaling pathway in combination with a specific inhibitor of that particular signaling pathway. Typically, a cell's CAS is measured in ohms.

The term "antibody" is used in the broadest sense and specifically includes monoclonal antibodies (including full length monoclonal antibodies), humanized antibodies, chimeric antibodies, multispecific antibodies (e.g., bispecific antibodies), and antibody fragments that exhibit a desired biological activity or function.

Antibodies can be chimeric, humanized, or human, for example, and can be antigen-binding fragments of these. "Antibody fragments" comprise a portion of a full-length antibody, generally the antigen binding or variable region thereof. Examples of antibody fragments include Fab, Fab', F(ab')2, and Fv fragments; diabodies; linear antibodies; single-chain antibody molecules; and multispecific antibodies such as bispecific antibodies, for example formed from antibody fragments. "Functional fragments" substantially retain binding to an antigen of the full-length antibody, and retain a biological activity. Antibodies can be "armed" or "conjugated" by combining with one or more other drugs through covalent or other attachment to achieve greater potency, specificity, and efficacy than the individual drug molecules could achieve separately.

The term "confirming agent" as used herein refers to a small molecule, specific ligand of known function, or antibody or affinity/specificity reagent, known to disrupt or affect the pathway activity of interest that is employed in the test described herein. It is used in the test to confirm and quantify the amount of pathway activity associated with a specific mechanism of action generated when an activator agent is introduced to a cell sample that specifically initiates an activity directly associated with the pathway activity of interest. For instance, if an activator is a known ligand for a cell surface receptor, the activity measured in the method described herein that is changed after introduction of the confirming agent would represent the amount of activity associated with the pathway the method is intended to analyze. In a further example, as may be the case with a receptor comprised of ligand binding region, a receptor dimerization region, and a receptor tyrosine kinase region, an activator agent could be the ligand that binds to the receptor ligand binding site. A confirming reagent then could be an agent that prevented the event(s) preceding the ligand binding or subsequent to the ligand binding i.e. the receptor dimerization or the receptor tyrosine kinase activity subsequent to the receptor dimerization. Furthermore, the confirming reagent could be an agent that refines a particular part of the downstream signaling pathway activated or dysfunctional to the patient of interest.

The term "monoclonal antibody" as used herein refers to an antibody obtained from a population of substantially homogeneous antibodies, i.e., the individual antibodies of the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The term "immunocapture reagents" refers to any type of antibody and additionally includes aptamers composed of RNA, DNA, and polymers containing synthetic variants of bases, or any synthetic molecule where the aptamer or reagent has been constructed and selected to specifically recognize and bind another molecule and signal its presence, quantity, and or quality.

The term "culturing" refers to preparation of cells to perform the present invention. The preparation can include at different times in the practice of the current invention, various media, media supplements, various conditions of temperature, humidity, CO2%, seed densities, cell type purity or mixtures and other conditions known to those practiced in the art of cell culture. The preparation may include conditions that allow the cells to proliferate, become quiescent, senesce, and enter, pass or are checked at various stages of cell cycle. The culturing may include any number of media or supplements known to those practiced in the art such as but not limited to vitamins, cytokines, growth factors, serums (Ex. source animal is bovine, fetal bovine, human, horse or other mammal), metabolites, amino acids, trace minerals, ions, pH buffers, and or glucose, that allow and or optimize the ideal practice of the present invention. Culturing the cells may be practiced with serum-free and or activator-free media before or following activation by the present invention. The culturing may ideally comprise conditions designed to mimic the tumor microenvironment of the patient. The culturing preparation may ideally comprise conditions that are designed to place particular pathways into a basal or heightened level to permit the measurement of agonism or antagonism of the pathway activity.

The term "base media" refers to a type of culture media that contains, in well defined amounts, inorganic salts, essential amino acids, glucose, vitamins, and pH buffer and it does not contain agents that stimulate the signaling pathway the method is intended to analyze. Many base media are known to those practiced in the art and can include for example DMEM, F12, MEM, MEGM, RPMI-1640 and combinations thereof. For example, when the ErbB signaling pathways are to be analyzed, the base media does not contain reagents known to perturb the ErbB pathways. Base media is used to maintain a cell culture such that the cell population remains viable and retains its heterogeneity of individual cell types and a normal distribution of cells representing the different phases of the cell cycle. It is used to culture a sample of diseased cells obtained from a subject in the methods described herein just prior to the step in the methods where a sample of disease cells are contacted with activator agents.

The term "fresh" when applied to a material refers to a material that has not yet been used. Fresh base media is thus base media that has not yet been used. Fresh base media can be added to a vessel containing a sample of disease cells already being cultured in base media to increase the volume of base media in the vessel containing the cell culture. Alternatively, a portion of the base media that has been used to culture a sample of diseased cells in a vessel can be removed from the cell culture vessel and replaced with fresh base media. In either case, when more than 50% of the total base media volume in a cell culture vessel is fresh base media, the cell culture vessel is considered to contain fresh base media. Cells cultured in the same base media for extended periods of time (e.g. more than 72 hours) will lose the heterogeneity of individual cell types and the majority of the cells may enter G0/G1 cell cycle phase which may interfere with the measurement of signaling pathway activity. A cell sample placed in fresh media requires a period of time (e.g. at least 12 hours) to adjust to the new media such that the cell sample reflects the heterogeneity of individual cell types found in the original cell sample and a normal distribution of cells representing the different phases of the cell cycle.

The term "buffer media" refers to a solution that contains pH buffer and an isotonic solution. Buffer media is typically used to starve a sample of cells or drive the cells into quiescence or senescence such as one finds when cells are resting is cell-cycle $G_0/G_1$.

"Chimeric" antibodies (immunoglobulins) contain a portion of a heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., 1984, *Proc. Natl. Acad. Sci. USA* 81:6851-6855).

The term "humanized antibody", as used herein, are antibodies that contain minimal sequence derived from nonhuman immunoglobulin. For the most part, humanized antibodies are human immunoglobulins (recipient or acceptor antibody) in which variable domain hypervariable region residues of the recipient antibody are replaced by hypervariable region residues from a nonhuman species (donor antibody), such as mouse, rat, rabbit, or nonhuman primate having the desired specificity, affinity, and capacity. The hypervariable regions can be complementarity-determining regions (CDRs) defined by sequence (see, for example Kabat 1991, 1987, 1983), or hypervariable loops (HVLs) defined by structure (see for example, Chothia 1987), or both.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens, laminins, other glycoproteins, peptides, glycosaminoglycans, proteoglycans, vitronectin, Intercellular-CAMs, VascularCAMs, MAdCAMs), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals. Coatings can also include cell surface receptor or cell surface cognate binding proteins or proteins with affinity for said cell surface proteins.

The term "baseline measurement" refers to a physiologic beginning point for a set of cells to be tested and is based on an evaluation of measurements over a period of time before drug is added. This may include a basal cellular metabolism measurement or CReMS reading prior to exogenous activation. This may alternatively include but not be limited to include the CReMS measurement of a normal healthy cell metabolic function with or without exogenous activation.

The term "Cellular Response Measurement System" or "CReMS" refers to a device that can quantitatively determine a change in a physiological or cellular response parameter in a cell, in and between cells, and between cells and the instrumentation device. In embodiments the cell is a whole label free cell. A change in a physiological or cellular response parameter is measured by determining change in an analyte such as glucose, oxygen, carbon dioxide, amine containing materials such as proteins, amino acids, or of the extracellular matrix, or of a cell signaling molecule, or of cell proliferation, cell morphology, or cytoskeletal rearrangement. An example of a CReMS is a biosensor.

The term "CReMS Signal" as used herein is defined as a measure of cellular physiologic change of cells when those cells are analyzed by a chemo-electric CReMS. The CReMS signal and changes in the CReMS signal can have various units as related to the particular chemo-electric transducer measuring the physiologic change. For example, the CReMS signal may have units of but not be limited to cell index, impedance, wavelength units, pH units, voltage, current, or become dimensionless by using ratios of the units. Any of these units may have a time component. The CReMS signal can be mathematically modified for clarity of interpretation as is frequently done by those practiced in the art of biology, biochemistry and biophysics, for example including normalization, baselining, curve subtracting, or any combination of these. The CReMS signal may be measured at a single time point, or, more preferably, over a continuous series of time points representing a complete pattern of cellular physiologic response.

The term CReM "optical signal" is defined as the wavelength value or change in wavelength value measured as light is reflected from the photonic crystal biosensing CReMS upon which the cells rest. The units are typically in picometers or nanometers though could also become dimensionless if ratios of changes are reported. The "optical signal" could be expressed in said units combined with time. The shift in reflected wavelengths of light is proportional to the mass upon the photonic crystal surface. Thus the "optical signal" is a quantitative measure of the number of cells on the CReMS. Furthermore, the "optical signal" is a measure of the cell physiological status as for example changes in cell morphology, cell adhesion, cell viability, structural rearrangements of the cell lead to differences in the amount of mass upon the sensor that are detected as wavelength shifts.

The term "Cell Index" as used herein is defined as a measurement of impedance and can be applied in one instance of the present invention by measuring at a fixed electrical frequency of, for example, 10 kHz and fixed voltage.

And calculated by the equation Cell Index$_i$=($R_{tm}$−$R_{t0}$)/F

Where:
i=1, 2, or 3 time point
F=15 ohm in one example when the instrument is operated at 10 kHz frequency
$R_{t0}$ is the background resistance measured at time point T0.
$R_{tm}$ is the resistance measured at a time point Tn following cell addition, cell physiologic change, or cell activation.

Cell index is a dimensionless parameter derived as a relative change in measured electrical impedance to represent cell status. When cells are not present or are not well-adhered on the electrodes, the CI is zero. Under the same physiological conditions, when more cells are attached on the electrodes, the CI values are larger. CI is therefore a quantitative measure of cell number present in a well. Additionally, change in a cell physiological status, for example cell morphology, cell adhesion, or cell viability will lead to a change in CI.

The term "measurand" is defined as the quantity intended to be measured in a clinical test. For the invention described herein, the quantity intended to be measured is the change in physiologic response of cells to activation. The change in measurements of a physiologic response of cells to activation can be determined mathematically using a variety of Euclidean mathematical analyses and can be reported numerically in the case of a quantitative test or reported as a positive or negative result in the case of a qualitative test. In both quantitative and qualitative tests, the measurand (e.g. test result) is compared to a cut-off value above which and below which different clinical decisions or interpretations are made.

The term "output value" is a type of measurand and refers to the difference in the CReMS signal, such as measurements of cell adhesion or attachment, that occurs in a viable cell sample from a subject contacted with one or more activator agents that selectively effect signaling pathways and or one or more therapeutic agents that effect the same signaling pathways as the activator agents. The output value may be derived using a variety of Euclidean mathematical analyses of the CReMS signal obtained over a period of time, and can be reported numerically in the case of a quantitative test or reported as a positive or negative result in the case of a qualitative test. For example, a cell sample from a subject contacted with an activator agent alone may generate a CReMS signal of 1,000 units and a cell sample from the same subject contacted with the activator agent and therapeutic agent may generate a CReMs signal of 100 units. The output value in this example would equal 900 CReMS signal units, which is the difference in CReMS signal units measured in the cell sample contacted with activator agent alone and the cell sample contacted with the activator agent and therapeutic agent combined. In both quantitative and qualitative tests, the output value (e.g. test result) may be compared to a cut-off value above which and below which different clinical decisions or interpretations are made.

The term "output value percentage" refers to the percent change in CReMS signal that occurs in a viable cell sample from a patient cell sample contacted with one or more activator agents that selectively effect signaling pathways and one or more therapeutic agents that effect the same signaling pathways as the activator agents, as compared to the sample contacted with one or more activator agents or one or more therapeutic agents alone. For example, a cell sample from a subject contacted with an activator agent alone may generate a CReMS signal of 1,000 units and a cell sample from the same subject contacted with the activator agent and therapeutic agent may generate a CReMs of 100. The output value percentage in this example would equal 90%, which is the difference in CReMS signal units measured in the cell sample contacted with activator agent alone and the cell sample contacted with the activator agent and therapeutic agent combined divided by the CReMS signal units measured in the cell sample contacted with activator agent alone. In both quantitative and qualitative tests, the output value percentage may be compared to a cut-off value percentage above which and below which different clinical decisions or interpretations are made.

The term "basal morphology" refers to the form and structure of a cell or cell sample prior to the introduction of an agent, activator, or stimulus.

The term "cell adhesion" (used interchangeably with "cellular adhesion", "cell attachment" or "cellular attachment") refers to the binding of a cell to another cell, to an extracellular matrix component or to a surface (e.g., microtiter plate).

The term "biomarker" refers, in the most general sense, to a biological metric of the condition of a cell or patient health or disease status. A non-limiting listing of general biomarkers includes biologically derived molecules found in a mammal, biological activity of a mammalian cell or tissue, gene copy number, gene mutations, single nucleotide polymorphisms, gene expression levels, mRNA levels, splice variants, transcriptional modifications, post-transcriptional modifications, epi-genetic modifications, cell surface markers, differential expression of a protein or nucleic acid (including all forms of functional RNA), amplification of a nucleic acid, cell morphology, post-translational modifications, protein truncations, phosphorylations, dephosphorylations, ubiquitination, de-ubiquitination, metabolites, hormones at any stage of biosynthesis, cytokines, chemokines, and combinations thereof. A subset of biomarkers are used for diagnostic and therapeutic selection purposes to help pathologists diagnose disease and to help doctors prescribe therapy. Biomarkers typically measure, in fixed, mounted tissue, a gene copy number, a genetic mutation, or the level of a protein without specification of the state or activity of the protein. The present invention includes a new type of biomarker, a physiologic response parameter that is the activity or dynamic result from a live patient cell sample.

The term "biomarker status" refers to assessment of a biomarker(s) in a patient, or patient's cells, and typically is reported as "biomarker positive" when the biomarker is present or "biomarker negative" when the biomarker is absent. When a protein receptor is used as a biomarker (e.g. HER2/ErbB2 or ER), a biomarker positive result is also referred to as the receptor being over-expressed or amplified and a biomarker negative result is referred to as the receptor being normally expressed or non-amplified. For diseases where a biomarker or biomarker signature is a prognostic indicator of disease progression or predicts therapeutic efficacy, current clinical practice relies on the measurement of the amount of biomarker or its related mutations to refine a patient's diagnosis by classifying the patient as either biomarker negative or positive. Determination of biomarker status is often used to guide selection of the drug therapeutic to treat a patient. The cut-off value of a biomarker measurement that is used to distinguish biomarker positive and biomarker negative patients varies from biomarker to biomarker. When the biomarker is a drug target, the cut-off value is the condition above which a patient will receive a therapeutic that targets the biomarker and below which a patient will not receive a therapeutic that targets the biomarker. Clinical trials are typically required to identify the clinical relevance of a biomarker.

The term "biosensor" refers to a device that measures an analyte or a change in an analyte or physiologic condition of a cell. In embodiments, the biosensor typically contains three parts: a biological component or element that binds or recognizes the analyte (including non-limiting examples such as extracellular matrix, cell signaling molecule, or cell proliferation, tissue, cells, metabolites, catabolites, biomolecules, ions, oxygen, carbon dioxide, carbohydrates, proteins etc.), a detector element (operating in a physicochemical manner such as optical, piezoelectric, electrochemical, thermometric, or magnetic), and a transducer associated with both components.

The term "optical biosensor" refers to a device that measures fluorescence, absorption, transmittance, density, refractive index, and reflection of light. In embodiments, an optical biosensor can comprise an optical transducer for converting a molecular recognition or molecular activation event in a living cell, a pathogen, or combinations thereof into a quantifiable signal. Additionally, embodiments could include a photonic crystal device, an optical waveguide device, and a surface plasmon resonance device.

The term "impedance biosensor" refers to a device that measures complex impedance changes (delta Z, or dZ) of live patient cells where impedance (Z) is related to the ratio of voltage to current as described by Ohm's law (Z=V/I). It is sensitive to the local ionic environment at the electrode interface with the cells and detects these changes as a function of voltage and current fluctuations. Physiologic changes of the cells as a result of normal function or activation thereof result in quantifiable changes to the flow of current around the electrodes and influence the magnitude and characteristics of the signal measured. In embodiments, an impedance biosensor can comprise electrodes or an electrical circuit for converting a molecular recognition or molecular activation event in a living cell, a pathogen, or combinations thereof into a quantifiable signal. In embodiments, an ISFET biosensor can comprise an ion selective field effect electrical transducer for converting an analyte recognition or cellular activation event in a living cell, a pathogen, or combinations thereof into a quantifiable signal. When an analyte concentration in an ISFET biosensor changes, the current in the transistor changes, which creates a quantification signal.

The term "cell signaling" refers to the intracellular or intercellular transfer of information. Cells signaling can be achieved by direct contact between cells or by the release of a substance from one cell that is taken up by another cell. Intercellular signaling can occur via an interaction between two molecules (e.g., a ligand and a receptor). Receptor binding can trigger a cascade of intracellular signaling (e.g., initiation of biochemical changes within the cell or modification of the membrane potential).

The term "signaling pathway" refers to a series of cellular components involved in the intracellular or intercellular communication or transfer of information, including cell surface receptors, nuclear receptors, signal regulatory proteins, and intracellular signaling components. As used herein, a particular "signaling pathway" may be named according to the cell surface receptor that triggers the cascade of intracellular signaling or according to any of the components involved in the intracellular signaling. For example, binding of EGF to EGFR initiates signaling pathway activation that can include MAPK and/or PI3K. Thus, the terms "EGFR signaling pathway", "MAPK signaling pathway" and "PI3K signaling" pathway each can be used to encompass the signaling pathway that is initiated by binding of EGF to EGFR.

The terms "signaling activity," "pathway activity," "cell signaling activity," and "signaling pathway activity" are used interchangeably and refer to the events occurring during abnormal or normal function of a signaling pathway. Signaling activity is often associated primarily with one cell surface receptor (e.g. EGF receptor initiating EGF pathway). However, signaling activity in one pathway may be driven by signaling activity associated with pathway members from other signaling pathways that are upstream, downstream or lateral to a signaling pathways' cell surface receptor. This reflects the interconnected nature of signaling activity where multiple points of pathway convergence, cross-talk between pathways, and feedback loops between pathways can enable signaling activity from one pathway to affect the signaling activity of a different pathway (see Giulliano et al., Bidirectional Crosstalk between the Estrogen Receptor and Human Epidermal Growth Factor Receptor 2 Signaling Pathways in Breast Cancer: Molecular Basis and Clinical Implications, Breast Care (Basel). 2013 August; 8(4): 256-262). Cancer patients whose tumors are driven by signaling activity from two or more interconnected pathways may thus respond to a targeted therapy that binds to a target different than an abnormally functioning pathway's activation point. Due to the nature and complexity of cancer, a cancer patient signaling pathway dysfunction may contain unique interconnections to other pathways that are not commonly described in healthy normal populations.

The term "HER family-related signaling pathway" refers to the intracellular signaling pathways associated with signaling through a HER family receptor (HER1/ErbB1/EGFR, HER2/ErbB2, HER2/ErbB3 and HER4/ErbB4). HER family receptors and non-limiting examples of the corresponding ligands known to bind to each receptor are summarized below in Table 1.

TABLE 1

| | Receptor | | | |
|---|---|---|---|---|
| Ligand | ErbB1 | ErbB2 | ErbB3 | ErbB4 |
| EGF | + | − | − | − |
| TGF-α | + | − | − | − |
| HB-EGF | + | − | − | + |
| amphiregulin | + | − | − | − |
| betacellulin | + | − | − | + |
| epigen | + | − | − | − |
| epiregulin | + | − | − | + |
| neuregulin 1 | − | − | + | + |
| neuregulin 2 | − | − | + | + |
| neuregulin 3 | − | − | − | + |
| neuregulin 4 | − | − | − | + |

Although HER2/ErbB2 is not known to have a specific ligand, it is known in the art that signaling activity by HER2 can be assessed, for example, through use of HER1/HER3 ligands in combination.

The term "ER-related signaling pathways" refers to the intracellular signaling pathways associated with signaling through an estrogen receptor (ER), including ERα and ERβ. Known ligands for ER (which may differ in their affinity for the alpha or beta isoforms of the ER) include estradiol, estrone, raloxifene, estriol and genistein.

The term "cytoskeletal organization" refers to the arrangement of the internal scaffold of a cell. A cell's cytoskeleton comprises filaments that serve to support cytoplasmic or membrane elements and/or intracellular organelles. The cytoskeleton also helps to maintain the shape of a cell.

The term "cell proliferation" refers to an increase in the number of cells as a result of cell growth and cell division.

The term "cell survival" refers to the viability of a cell characterized by the capacity to perform certain functions such as metabolism, growth, movement, reproduction, some form of responsiveness, and adaptability.

The term "efficacy" refers to the extent to which a specific intervention produces a beneficial result. In embodiments, the intervention can be a therapeutic agent, such as a small molecule or an antibody or a targeted peptide of an organic reagent with high affinity and specificity for intervention at a known protein. A beneficial result includes without limitation an inhibition of symptoms, a decrease in cell growth, an increase in cell killing, an objective tumor response, an increase in a patient's survival period, an increase in a patient's progression free survival period, an increase in a patient's disease free survival period, a decrease in inflammation, and an increase in immune responsiveness.

An "extracellular matrix component" is a molecule that occurs in the extracellular matrix of an animal. It can be a component of an extracellular matrix from any species and from any tissue type. Non-limiting examples of extracellular matrix components include laminins, collagens, fibronectins, other glycoproteins, peptides, glycosaminoglycans, proteoglycans, etc. Extracellular matrix components can also include growth factors.

The term "global phenotype" refers to a plurality or composite of observable properties of a cell or cell sample as a whole and reflect development, biochemical or physiological properties, phenology, behavior, and products of behavior. A global phenotype may include but not be limited to cell size, cell shape, distinctive protuberances, outgrowths, spreading, attachment foci density, cytoskeletal arrangements, cell proliferation patterns, receptor phagocytosis, or attachment foci number, changes in pH, uptake or efflux of metabolites, signaling proteins and growth factors, oxygen, CO2, glucose, ATP, and ions such as magnesium, calcium, potassium.

The term "event specificity" refers to a physical observation of a specific property of a cell. Such specific properties relate to a specific cellular function, exogenous activation, or pathway agonism/antagonism as part of the intended and/or expected physiological response of the cell to a particular activator or therapeutic agent. Activators and therapeutic agents may be known to be targeted to affect a certain aspect of the cell function such as cytoskeletal structure, or a cellular pathway. The physically observable event is called event specificity because the physically observable event in the cell in the presence of the activator or the therapeutic agent is a reflection of the intended and/or expected effect the activator or therapeutic agent on the cell. For example, the addition of vinblastine to most cell samples on an attachment biosensor type of CReMS produces a profound reduction in signal. Vinblastine is a cellular cytoskeletal scaffolding disrupter. The reduction in signal is a physically observable event of the cell linked specifically to loss of cell shape and attachment caused by the drug action at microtubule molecules.

The term "synergy" or "synergistic" refers to a test result where the CReMS signal, output value, or output value percentage measured when a cell sample is tested with two or more activating agents and/or two or more therapeutic agents is greater than the sum of corresponding measurements obtained when the cell sample is tested with the activator agents and/or therapeutic agents individually. A synergistic result would occur when the simultaneous addition of two therapeutic agents to a cell sample contacted with two activating agents produces a greater CReMS signal, output value or output value percentage than the sum of CReMs signal, output values, or output value percentages obtained when each therapeutic agent is tested individually with the two simultaneous activator agents. For example, in a cell sample, the output value measured after a portion of the cell sample is tested with a combination of activator agents EGF and HGF and with an EGFR inhibitor alone equals 250. When a different portion of the same cell sample is tested with the same combination of activator agents (EGF and HGF) and an HGFR inhibitor alone, the output value equals 150. However, the output value measured after a different portion of the same cell sample is tested with a combination of activator agents EGF and HGF and a combination of EGFR and HFGR inhibitors equals 900, or 500 more than the sum of the two output values (250 plus 150) from the tests where each inhibitor was tested alone with the two activator agents. The higher output value obtained when the two therapeutic agents are tested in combination, rather than individually, suggests that the two therapeutic agents have a synergistic inhibitory effect on the signaling pathways activated with the activator agents. Synergy thus describes changes in cell signaling activity that cannot be observed when signaling pathways are activated or inhibited alone.

The term "Impedance" as used herein is defined by a physical law relating voltage and current by the equation: Impedance (ohm)=Voltage (volts)/Current (amperes) or $Z=V/I$.

"Mammal" for purposes of treatment or therapy refers to any animal classified as a mammal, including humans, domestic and farm animals, and zoo, sports, or pet animals, such as dogs, horses, cats, cows, and the like. Preferably, the mammal is human.

The term "microcantilever device", "microcantilever array", or microcantilever apparatus" refers to a type of CREMS instrument comprising at least one cantilever, a flexible beam that may be bar-shaped, V-shaped, or have other shapes, depending on its application. One end of the microcantilever is fixed on a supporting base, another end standing freely. Microcantilevers can measure concentrations using electrical methods to detect phase difference signals that can be matched with natural resonant frequencies (examples as described in U.S. Pat. No. 6,041,642, issued Mar. 28, 2000, which is hereby incorporated by reference) Determining a concentration of a target species using a change in resonant properties of a microcantilever on which a known molecule is disposed, for example, a macromolecular biomolecule such as DNA, RNA, or protein. Deflection is measured using optical and piezoelectric methods.

The term "normal functioning" refers to pathways in cells that have a defined system of checks and balances that prevent the cells from becoming dysfunctional from unnatural levels of signaling, replication, loss of contact inhibition, and aberrant gene copying and amplification. In many cases, with pathways beginning in some quiescent or steady basal state, addition of small amounts of activator at the pathway members' EC50 concentration will have only a small transient effect as the cell system recognizes the activator, initiates the pathway activity, and then down regulates the activator effect to maintain balance with other cellular function. Diseased function often is recognizable as over-reaction to an activator, hyper/hypo activity along the pathway, inappropriate inter-pathway activity to accommodate the activator effect, and failure to downregulate the minimal activator effect. Additionally, with some diseased states, a basal state for some pathway members cannot be reached for a pathway. These systems are described as constitutively activated.

The term "normal reference interval" is defined here as the interval between and including two numbers, an upper and lower reference limit, which are estimated to enclose a specified percentage of the values obtained from a population of healthy subjects (e.g. those lacking the disease of interest). For most analytes, the lower and upper reference limits are estimated as the 2.5th and 97.5th percentiles of the distribution of test results for the reference population, respectively. In some cases, only one reference limit is of medical importance, usually an upper limit, say the 97.5th percentile. The confidence intervals for the estimates of the limits of the reference interval can be constructed assuming random sampling of the reference population—generally about 120 reference subjects. The width of each confidence interval depends on the number of reference subjects, as well as the distribution of the observed reference values.

The normal reference range cutoff is determined and set by a process of selection of reference individuals, analytical methods applied to those reference individuals, and concludes with data collection and analysis as defined by the publication Clinical Laboratory Standards Institute Approved Guideline EP28-A3C "Defining, Establishing, and Verifying Reference Intervals in the Clinical Laboratory" whose content is incorporated by reference here in its entirety.

In one embodiment, reference individuals would be individuals free of disease, especially all forms of cancer. A normal reference interval would be determined by testing the normal reference individuals using the methods described herein. The upper limit of the normal reference interval would represent the upper limit of normal pathway activity. In one embodiment, a cut-off value that distinguishes between positive and negative test results would equal the upper limit of the normal reference interval. In other embodiments, the cut-off value would equal the upper limit of the normal reference interval plus any, a combination, all, or a multiple of one, a combination, or all of the following values: limit of detection, limit of blank, limit of quantification, standard deviation of the measurand.

The group of reference individuals free of disease could be further defined by various characteristics beyond the disease of interest. For instance, in an application of the present invention to breast cancer, the group of reference women free of disease may be further defined to include any, combinations, or all of the following characteristics: pre- or post-menopausal, lactating or non-lactating, having borne children, having BRCA gene mutations, presence of diabetes, obesity as determined by BMI (Body Mass Index). abstinence from pharmacologic agents such as hormones or other drug addictions, abstinence from dietary materials such as alcohol and or familial history of cancer.

The terms "abnormal signaling pathway," "aberrant signaling pathway," or "dysfunctional signaling pathway" are used interchangeably and refer to a cell signaling pathway that has been disrupted in such a way as to impair the ability of the cell to perform its normal function. The source of the cell signaling disruption and resulting dysfunction is typically a consequence of damage to the genome or proteome that interferes with the signaling pathways' normal function. This damage can be, for example, the result of endogenous processes such as errors in replication of DNA, the intrinsic chemical instability of certain DNA bases, tumor microenvironment, dynamic system adjustment or selection, or from attack by free radicals generated during metabolism. Some inactivating mutations occur in genes responsible for maintaining genomic integrity facilitating the acquisition of additional mutations. Additional mechanisms that affect the genomic level of cellular control involve epigenetic mechanisms whereby the expression of specific genes has been altered by changes to the histone proteins' function. The epigenome function has been demonstrated to be highly adaptive or responsive to many different environmental conditions including conditions that participate in disease etiology and propagation. Various RNA-based mechanisms of pathway dysfunction have been described at the transcriptional, post-transcriptional, translational, and post-translational levels.

Additionally, many actions of pathway dysfunction at the protein level are known to those skilled in the art of cellular molecular biology. Pathway dysfunction can be the result of over or under expression of a pathway member or members or co-factor(s), protein activity present in unnatural cell types or cellular locations, protein interaction with unnatural pathway members also known as pathway cross-reactivity, dysfunctional feedback or feedforward loops, or post-translational modifications. Pathway dysfunction can additionally be the result of activity of the proteome, proteasome, kinome, metabolome, nuclear proteins and factors, cytoplasmic proteins and factors, and or mitochondrial proteins and factors.

When cells with dysfunctional pathways replicate, they can pass on the abnormality to their progeny, which increases the likelihood that the cells become diseased. By analyzing the activity of a cell signaling pathway in live cells, it is possible to determine whether the signaling pathways of the cells are functioning normally or abnormally.

The terms "ultra-sensitive signaling pathway" or "hyperactive signaling pathway" are used interchangeably and refer to a cell signaling pathway in which only a very low level of cellular input difference, such as a signaling pathway activator (e.g., a receptor ligand concentration difference of 1 nM to 10 nM), is capable of causing a low level of activity (e.g., 10% cellular output) to change to a very high level of pathway activation responsiveness (e.g., 90% cellular output). Typically, a component (e.g., enzyme) within an ultra-sensitive or hyperactive signaling pathway is considered to be ultra-sensitive or hyperactive if it requires less than an 81-fold increase in stimulus to drive activity from 10% to 90% maximal response. Signaling pathway ultrasensitivity is described further in and incorporated by reference in their entirety in Ferrell, J. E. and Ha, S. H. (2014) *Trends in Biochem. Sci.* 39:496-503; Ferrell, J. E. and Ha, S. H. (2014) *Trends in Biochem. Sci.* 39:556-569; Ferrell, J. E. and Ha, S. H. (2014) *Trends in Biochem. Sci.* 39:612-618; Huang, C. Y. and Ferrell, J. E. (1996) *Proc. Natl. Acad. Sci. USA* 93:10078-10083; Kim, S. Y. and Ferrell, J. E. (2007) *Cell* 128:1133-1145; Trunnell, N. B. et al. (2011) *Cell* 41:263-274.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azidoribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R', P(O)OR', CO or CH.sub.2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Polypeptide" refers to a peptide or protein containing two or more amino acids linked by peptide bonds, and includes peptides, oligimers, proteins, and the like. Polypeptides can contain natural, modified, or synthetic amino acids. Polypeptides can also be modified naturally, such as by post-translational processing, or chemically, such as by amidation, acylation, cross-linking, and the like.

The term "quartz crystal resonators/microbalance" refers to a type of CREMS device that measures mass by measuring the change in frequency of a piezoelectric quartz crystal when it is disturbed by the addition of a small mass such as a virus or any other tiny object intended to be measured. Frequency measurements are easily made to high precision, hence, it is easy to measure small masses.

As used herein, "sample" refers to anything which may contain a moiety to be isolated, manipulated, measured, quantified, detected or analyzed using apparatuses, microplates or methods in the present disclosure. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

The term "cell sample" refers to cells isolated from a particular subject, where the cells are isolated from a subject's biological fluids, excretions, or tissues. Cells isolated from tissue can include tumor cells. Cells isolated from tissue include homogenized tissue, and cellular extracts, and combinations thereof. Cell samples include isolation from, but are not limited to, blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, marrow, or hair.

The term "CELx" test refers generally to the various embodiments of the methods described herein.

The term "disease cell sample" refers to a plurality of cells from the site of disease or cells that have the characteristic of disease.

The term "healthy cell sample" refers to a cell sample wherein the cells do not have or are extracted from a tissue that does not have the disease that is being tested. For example, when a particular subject is being tested for the effects of a therapeutic agent against the subject's breast cancer, non-cancerous cells or cells from non-breast tissue are considered "healthy". The term "healthy cell sample" is not a determination or reflection upon the whole health status of the subject. For purposes of deriving a normal reference interval, it is often the case that the healthy cell samples used are obtained from subjects who do not have the disease that is being tested.

The term Analytical "Sensitivity" refers to a test or the detection limit, and is defined as the lowest quantity differentiated from Zero. (e.g. 95% confidence intervals or 2 standard deviations (SD) above the mean of the Zero control are commonly used).

The Term Clinical "Sensitivity" refers to the proportion of subjects with the target condition in whom the test is positive or how often the test is positive when the condition of interest is present. Clinical "Sensitivity" of a test is defined as an estimate of accuracy provided by the calculation: 100%×TP/(TP+FN) where TP is the number of True Positive events for an outcome being tested and FN are the number of False Negatives events, incorrectly determined events as negative.

Clinical "Specificity" refers to the proportion of subjects without the target condition in whom the test is negative or how often the test is negative when the condition of interest is absent. Clinical specificity is estimated by the calculation: 100%×TN/(FP+TN) where TN is the number of True Negative events for an outcome being tested and FP is the number of False Positives, incorrectly determined events as positive.

The term "surface plasmon resonance device" refers to an optical biosensor type of CReMS that measures binding events of biomolecules at a metal surface by detecting changes in the local refractive index.

The term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term encompasses those compounds or chemicals traditionally regarded as drugs, vaccines, and biopharmaceuticals including molecules such as proteins, peptides, hormones, nucleic acids, gene constructs and the like. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Therapeutic agents include, but are not limited to, anticancer therapeutics, antipsychotics, anti-inflammatory agents, and antibiotics.

The terms "cytotoxic therapy" and "chemotherapy" refer to treatment with one or more therapeutic agents, wherein the agent(s) exhibits non-specific or non-targeted cytotoxicity against diseased cells (as well as, possibly, non-diseased cells).

The term "targeted therapeutic", "targeted pathway drug," "pathway drug," or "targeted drug," refers to any molecule or antibody with therapeutic capacity designed to selectively bind to a specific biomolecule (e.g. protein) involved in a disease process, thereby regulating its activity. Non-limiting examples of biomolecules to which a targeted therapeutic may bind include cell-surface receptors and inter- and intracellular signaling pathway components. As described herein, a "targeted therapeutic" that is administered to a subject for treatment may be the same targeted therapeutic that is tested in vitro as described herein to determine the status of a signaling pathway in a subject cells or, alternatively, the targeted therapeutic that is chosen to be administered for treatment can be a different targeted therapeutic than was tested in vitro but that targets (e.g., selectively affects) the same signaling pathway as the targeted therapeutic that was tested in vitro (e.g., affects the same point or node of the signaling pathway as the tested targeted therapeutic).

The terms "HER2 therapy" or "HER2-targeted therapy" refer to treatments using one or more therapeutic agents that are designed to specifically target the HER2 molecule and/or signaling pathway(s), including but not limited to, for example antibodies and small molecules that target the HER2 molecule and/or signaling pathway(s). Such HER2 therapies may also target other members of the HER family, for example therapies that target both HER1 and HER2, HER1, HER2, and HER4, or HER3 alone.

The terms "ER therapy", "ER-targeted therapy" or "hormonal therapy" refer to treatments using one or more therapeutic agents that are designed to specifically target the ER molecule and/or signaling pathway(s), including but not limited to aromatase inhibitors, selective estrogen receptor modulators and selective estrogen receptor downregulators, as well as the combination of such therapies with therapies that inhibit cyclin-dependent kinases CDK4 and CDK6.

The term "anti-proliferative drug," "anti-proliferative agent," or "apoptosis inducing drug," refers to any molecule or antibody with therapeutic capacity that functions to reduce cell division, reduce cell growth, or kill cells. In many cases, the activity of these drugs is directed towards broad classes of biomolecules (e.g. DNA intercalation) involved in normal cellular processes and thus the drug may be less discriminant towards cell disease status.

The term "therapeutically active" refers to an effect on a signaling pathway that occurs when a subject's cancer cells are contacted with a targeted therapeutic agent, such as a small molecule or an antibody or a targeted peptide or any organic reagent with high affinity and specificity for intervention at a known protein. A therapeutically active targeted therapeutic agent is one that affects the signaling pathway(s) the targeted therapeutic agent is intended to affect. A targeted therapeutic agent that is more therapeutically active in a subject's cancer cells than another targeted therapeutic agent is one that has a greater effect on the signaling pathway it is intended to affect than the other therapeutic agent has on the signaling pathway the other therapeutic agent is intended to affect. There is evidence that in at least certain cancers, two or more signaling pathways may be interconnected with multiple points of convergence, cross-talk and feedback loops, such that inhibiting only one of the pathways can still result in the maintenance of signaling via the other (reciprocal pathway) (see e.g., Saini, K. S. et al. (2013) Cancer Treat. Rev. 39:935-946). Since the activities of one signaling pathway can affect the activities of other signaling pathways, a targeted therapeutic may disrupt signaling activity associated indirectly with that targeted therapeutic's binding site. In these cases, a targeted therapy may be considered therapeutically active if it is found to inhibit signaling activities for pathways not directly associated with that targeted therapeutic binding site.

A "variant" of a polypeptide refers to a polypeptide that contains an amino acid sequence that differs from a reference sequence. The reference sequence can be a full-length native polypeptide sequence or any other fragment of a full-length polypeptide sequence. In some embodiments, the reference sequence is a variable domain heavy chain or variable domain light chain consensus sequence. A polypeptide variant generally has at least about 80% amino acid sequence identity with the reference sequence.

B. Methods of Measuring Multiple Signaling Pathways

In one aspect of the invention, the method used to select a targeted therapeutic agent for treatment of a cancer patient involves evaluating the functional activity of multiple (two or more) signaling pathways in the patient's cancer cells. This approach allows for identification of the specific most active disease signaling pathway that is driving the patient's tumor, by simultaneously assessing the activity of several different signaling pathways in the tumor and comparing the results. The patient is then treated with a targeted therapeutic agent that affects the signaling pathway with the highest level of activity. The targeted therapeutic used for treatment may be the same targeted therapeutic that was tested in vitro to determine the functional status of the signaling pathway or, alternatively, the targeted therapeutic used for treatment can be a different agent than was tested in vitro but that affects the same signaling pathway as the targeted therapeutic tested in vitro.

Multiple signaling pathways can be examined in a patient's cancer cells one at a time (using different portions of the patient's cell sample to test each pathway individually) such that information is obtained in parallel about the activity of the various signaling pathways in the patient's cells. The results from this parallel analysis of the multiple different pathways can be compared to determine which targeted therapeutic/activator pair leads to the highest, output value of pairs tested and which targeted therapeutics are therapeutically active. Additionally, or alternatively, multiple signaling pathways can be examined simultaneously in the same cell sample by simultaneously contacting the sample with multiple targeted therapeutic/activator pairs (wherein each pair affects a different signaling pathway) (discussed further in subsection F below) for the benefit of identifying synergies. Non-limiting exemplary embodiments of these methods are described further in Example 1 (parallel analysis of multiple different signaling pathways) and Example 3 (simultaneous analysis of multiple different signaling pathways).

Accordingly, in one embodiment, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample with at least two sets of paired agents, each set comprised of a first agent that is a targeted therapeutic and a second agent that is an activator that is known to selectively affect the same signaling pathway the first agent is intended to address, wherein each set of paired agents affects a different signaling pathway, so as to upregulate or downregulate the signaling pathway as measured by an effect on cell adhesion or attachment, to produce a sample contacted with at least two sets of paired agents;

continuously measuring cell adhesion or attachment of the viable cancer cells in the sample contacted with each set of paired agents, relative to a sample of viable cancer cells obtained from the subject that is contacted with each of the first agents or each of the second agents alone;

determining by mathematical analysis of the continuous measurements an output value for each set of paired agents that characterizes whether a change in cell adhesion or attachment has occurred in the sample contacted with the set of paired agents, as compared to the sample contacted with the first agents or the second agents alone; and administering to the subject at least one targeted therapeutic that affects the same signaling pathway as the first agent from the set of paired agents determined to have the highest output value of all sets tested, indicating the administered targeted therapeutic agent is more therapeutically active in the cell signaling pathway of the subject's cancer cells than the targeted therapeutic(s) from the set(s) of paired agents with lower output value.

In another embodiment, the invention pertains to a method of identifying a targeted therapeutic that is therapeutically active in the signaling pathway it is intended to address in a subject's cancer cells, the method comprising:

culturing a sample comprising viable cancer cells obtained from the subject;

contacting the sample with at least two sets of paired agents, each set comprised of a targeted therapeutic and an activator that is known to selectively affect the same signaling pathway the targeted therapeutic is intended to address, wherein each set of paired agents affects a different signaling pathway, so as to upregulate or downregulate the signaling pathway as measured by an effect on cell adhesion or attachment, to produce a sample contacted with at least two sets of paired agents;

continuously measuring cell adhesion or attachment of the viable cancer cells in the sample contacted with each set of paired agents, relative to a sample of viable cancer cells obtained from the subject that is contacted with each of the targeted therapeutics or each of the activators alone;

determining by mathematical analysis of the continuous measurements an output value for each set of paired agents that characterizes whether a change in cell adhesion or attachment has occurred in the sample contacted with the set of paired agents, as compared to the sample contacted with the targeted therapeutics or the activators alone; and identifying the targeted therapeutic from the set of paired agents determined to have the highest output value of all sets tested, indicating the targeted therapeutic agent is more therapeutically active in the cell signaling pathway of the subject's cancer cells than the targeted therapeutic(s) from the set(s) of paired agents with lower output value.

In one embodiment, the targeted therapeutic(s) that is administered to the subject is the first agent(s) from the set of paired agents determined to have the highest output value. In another embodiment, the targeted therapeutic(s) that is administered to the subject is different than the first agent(s) from the set of paired agents determined to have the highest output value but targets the same signaling pathway as said first agent(s).

In various embodiments, the sample (e.g., different portions of the cell sample) is contacted with two, three, four, five, six, seven, eight, nine, ten, 15, 20, 25 or more sets of paired agents, wherein each set of paired agents affects a different signaling pathway. In an embodiment, the sample is contacted with ten or more sets of paired agents. Activator or therapeutic agents may be applied simultaneously as pools of two or more agents to the same portion of a cell sample. In one embodiment, the eleven different signaling pathways set forth in Table 16 are tested in parallel, for example using the paired sets of activators and targeted therapeutics set forth in Table 16 (as described further in Example 1).

In one embodiment, the set of paired agents comprises one targeted therapeutic and more than one activator, each of which activators is known to selectively affect the same signaling pathway the targeted therapeutic is intended to address. For example, in one embodiment, the set of paired agents comprises one targeted therapeutic and two different activators, each of which activators is known to selectively affect the same signaling pathway the targeted therapeutic is intended to address. This embodiment is also described further in subsection D below.

In one embodiment, the signaling pathways are selected from the group consisting of HER2/HER1, HER1, HER2/HER3, HER3, c-Met/HGF, ALK, FGFR, IGFR, EGFR, FLT3, Axl, PDGFR, SMO, Patched 1, Frizzled and Notch.

In one embodiment, the sets of paired agents and signaling pathways are selected from Table 2 shown below:

TABLE 2

| Pathway | Activator | Targeted Therapeutic |
|---|---|---|
| HER2/HER1 | EGF | Pertuzumab |
| HER2/HER3 | NRG1 | Pertuzumab |
| HER3 | NRG1 | Neratinib, afatinib |
| c-MET/HGF | HGF | SGX-523, tepotinib |
| ALK | FAM150A | Ceritinib |
| FGFR | FGF | BGJ398 |
| IGFR | IGF | Linsitinib |
| EGFR | EGF | Neratinib |
| PDGFR | PDGF | Imatinib, sunitinib, pazopanib |

TABLE 2-continued

| Pathway | Activator | Targeted Therapeutic |
| --- | --- | --- |
| FLT3 | FLT3L | Quizartinib |
| Axl | Gas6 | R428 (BGB324) |
| SMO | SAG1.3 | Vismodegib, Itraconazole |
| Patched1 | SHH | Vismodegib, Itraconazole, 5E1 |
| Frizzled | Wnt | LGK974 |
| Notch | DLL, Jagged, γ-secretase | Semagacestat |
| RON, MST1R | MSP or MST1 | ASLAN002 |
| TGFb | TGFb | Galunisertib (LY2157299) |
| EstrogenR | E2 | Tamoxifen, fulvestrant |
| TestosteroneR | Testosterone | anti-androgens, abiraterone |
| ProgesteroneR | P4 | anti-orogesterones, mifepristone |

In one embodiment, the signaling pathways are selected from the group consisting of HER2/HER1, HER1, HER2/HER3, HER3, c-Met/HGF, ALK, ROS, FGFR, IGFR, EGFR, FLT3, Axl, Tyro 3, Mer, PDGFR, SMO, Patched 1, Frizzled, Notch, MAPK, RON, RHO, AKT, FAK1, RAS, RAF, PI3K/PTEN, MAK, MKK, MEK, MEKK, Mos, Erk, MLK, MLK3, TAK, DLK, p38, ASK, SAPK, JNK, BMK, PKC, PI3K, PIK3/PTEN, Bad, Bcl, Bak, Bax, BID, Bim, Noxa, Puma, BH3, caspase, p53, NIK, NFkB, ROCK, XIAP, MOMP, ILK, PDK, insulin receptor (IR), IGFR, mTOR, Jak, PIKK, 4E-BP1, Raptor, KMT, MLL, KDM, UTX, DOT1L, BRD, TET, SirT1, Hat, SNF, DNMT, EZH, AMPK, PLC, CaMKK, glucose transporter, PFK, FAS, Krebs Cycle, glycolysis, TNFR, TRAD, TRAF, TAB, NEMO, NIK, IKK, RelA, RelB, kB, IL1R, IRAK, Myd88, TRADD, FADD, FLIPs, ICAD, CAD, PARP, lamins, ZNRF, WntR, PAR, GSK, Dsh, LGR, catenin, WTX, APC, Src, CBP, Fringe, Furin, Delta Jagged, NIC, presenilin, CDO, BOC, Gli, KIF, cyclin D, cyclin E, SARA, Smad, Smurf, NLK, p28, Myc, Max, Fos, Jun, LIMK, cofilin, CD44, FAT, KIBRA, FRMD, Mst, YAP, LATS, MOB, SAV, TEAD, Mer, SAB, TAZ, Rho, Rac, PAK, CREB, HER2, HER3, HER4, estrogen receptors, progesterone receptors, androgen receptors, GPER30, VEGF receptor, TGFbeta/SMAD, WNT, Hedgehog/GLI, HIF1 alpha, JAK/STAT, control of G1/S transition, DNA damage control, and apoptosis.

In one embodiment, each set of paired agents selectively affects a different HER family signaling pathway.

In one embodiment, each set of paired agents is selected from the sets of paired agents set forth in Table 12.

Various suitable targeted therapeutics, activators and signaling pathways are also described further in the subsections below and in the Examples.

In another aspect, the method involving assessment of multiple signaling pathways in a subject's cancer cells can further involve the selection of multiple targeted therapeutics for administration to the subject (i.e., a combination of targeted therapeutics for combination therapy). There is evidence that in at least certain cancers, two or more signaling pathways may be interconnected with multiple points of convergence, cross-talk and feedback loops, such that inhibiting only one of the pathways can still result in the maintenance of signaling via the other (reciprocal pathway) (see e.g., Saini, K. S. et al. (2013) *Cancer Treat. Rev.* 39:935-946. Thus, targeting of multiple pathways with multiple targeted therapeutics determined to be therapeutically active in a subject's cancer cells can lead to superior efficacy and better clinical outcomes. Furthermore, the use of rational combinatorial targeted therapy has been proposed as a solution to the ongoing challenge of cancer drug resistance (see e.g., Al-Lazikani. B. et al. (2012) *Nature Biotechnol.* 30:679-692).

Accordingly, in another embodiment, the method involving assessment of multiple signaling pathways in a subject's cancer cells can further involve identifying as active or administering at least two therapeutic agents to the subject: (i) the targeted therapeutic from the set of paired agents determined to have an output value percentage greater than 50% indicating the targeted therapeutic is therapeutically active in the cell signaling pathway of the subject's cancer cells and (ii) at least one additional therapeutic agent from the set of paired agents determined to have an output value indicating the targeted therapeutic is therapeutically active in the cell signaling pathway of the subject's cancer cells. For example, in one embodiment, the at least two therapeutic agents are determined to have an output value percentage greater than 50% indicating each targeted therapeutic is therapeutically active in the cell signaling pathway of the subject's cancer cells.

In one embodiment, the at least one targeted therapeutic that is administered to the subject is selected from the group consisting of cetuximab, erlotinib, gefitinib, lapatinib, pazopanib, trastuzumab, fulvestrant, tamoxifen, letrozole, anastrozole, exemestane, everolimus, abiraterone, bicalutamide, bortezomib, vemurafenib, ipilimumab, Pertuzumab, MEDI4276, ONT-380, Neratinib, Afatinib, Duligotuzumab, Dacomitinib, Sapitinib, Poziotinib, ASLAN001, MM-111 MM-121, MM-141, LJM716, U3-1287 (AMG 888), TK-A3/TK-A4, Lumretuzumab, REGN1400, AV-203, AZD5363, Afuresertib, MK-2206, Ipatasertib, Ridaforolimus, Temsirolimus, Selemetinib, Cobimetinib, GDC-0994, Taselisib, Alpelisib, Buparlisib, AZD8186, AZD8835, Panitumumab, REGN955, MM-151, Osimertinib, Rociletinib, AZD5363, SGX-523, Onartuzumab, Cabozantinib, Volitinib, Tivantinib, Capmatinib, Emibetuzumab, Rilotumumab, Ficlatuzumab, SAR125844, emibetuzumab, Sym015, AMG337, JNJ-61186372, glesatinib, 1202, LY3023414, Gedatolisib, JI-101, Ponatinib, Sunitinib, Crizotinib, Ceritinib, Brigatinib, Alectinib, BGJ398, Linsitinib, Quizartinib, R428 (BGB324), gilteritinib, Vismodegib, Itraconazole, 5E1, LGK974, Semagacestat, Cobimetinib, AZD4547, JNJ-42756493, Dalotuzumab, MEDI-573, Ganitumab, Sonidegib, Vantictumab, Ipafricept, Tarextumab, Brontictuzumab, SB431542, EW-7197, RepSox, AZD9291, Rociletinib, abraxane, brentuximab vedoton, ofatumumab, bevacizumab, alemtuzumab, bicalutamide, gemcitabine, imatinib, ixabepilone, romidepsin, cabrazitaxel, sorafenib, infliximab, lenalidomide, rituximab, dasatinib, nilotinib, temozolomide, bortezomib, azacitidine, tepotinib, lorlatinib, merestinib, RG6114, tucantinib, pazopanib, crizotinib, vemurafenib, goserelin acetate, abiraterone, a BH3 mimetic, navitoclax, anastrozole, letrozole, an aromatase inhibitor, ixabepilone, aflibercept, temsirolimus, irbritumomab, abiraterone, custirsen, enzalutamide, nivolumab, palbociclib, regorafenib, entinostat, ARN-509, ARN-810, BIND-014, dabrafenib, daratumumab, lambrolizumab, LDK378, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof.

For the methods involving assessment of multiple signaling pathways in a subject's cancer cells, sample preparation and culturing, continuous monitoring of cell adhesion or attachment and mathematical analysis are described in further detail in the subsections below.

In one embodiment, the activator in each paired set of agents is a protein, peptide, nucleic acid, metabolite, ligand, reagent, organic molecule, signaling factor, growth factor, biochemical, or combinations thereof. Examples of suitable activators are described further in the subsections below and in the Examples.

In one embodiment, cell adhesion or attachment is measured using an impedance biosensor or an optical biosensor. Use of biosensors is described in further detail in the subsections below.

In one embodiment, the cancer is selected from the group consisting of breast cancer, lung cancer, colorectal cancer, bladder cancer, kidney cancer, ovarian cancer and leukemia. Additional suitable cancers are described in the subsections below.

In one embodiment, the sample of viable cancer cells is cultured in a media comprising growth factors and free of serum. In another embodiment, the sample of viable cancer cells is also cultured in a media comprising an anti-apoptotic agent and free of serum. Culture conditions and culturing of cells is described in further detail in the subsections below.

C. Methods of Measuring Signaling Pathway Ultra-sensitivity

In one aspect of the invention, the method used to select a targeted therapeutic agent for treatment of a cancer patient involves identifying a signaling pathway in a patient's cells that is abnormally ultra-sensitive, and then treating the patient with a targeted therapeutic agent that affects this ultra-sensitive signaling pathway. An ultra-sensitive pathway is one in which the change of only a very low level of cellular input, such as a signaling pathway activator (e.g., a receptor ligand concentration change from 1 nM to 10 nM) is capable of causing a change from a low level (e.g., 10% of cellular output) of pathway activation to a very high level of pathway activation responsiveness (e.g., 90% cellular output). A signaling pathway in a patient's cancer cells that is abnormally ultra-sensitive is likely to be involved in driving the disease process (e.g., tumor growth), even if there are additional aberrant signaling pathways in the cancer cells. Thus, identifying a signaling pathway in a patient's cancer calls that is abnormally ultra-sensitive and then selecting a targeted therapeutic agent that targets this signaling pathway is an effective means for selecting therapeutically effective treatment regimens. A non-limiting exemplary embodiment of this method is described further in Example 2.

Accordingly, in one aspect, the invention pertains to a method of treating a human subject diagnosed with cancer, the method comprising:

administering to the subject at least one targeted therapeutic that selectively affects an abnormally active signaling pathway in the subject's cancer cells, wherein the signaling pathway has been determined to be abnormally active in the subject's cancer cells by a method comprising:

culturing a sample comprising viable cancer cells obtained from the subject;

contacting the sample with an activator that is known to selectively affect a signaling pathway, so as to upregulate or downregulate the signaling pathway as measured by an effect on cell adhesion or attachment, wherein a portion of the sample is contacted with a higher concentration of the activator and a portion of the sample is contacted with a lower concentration of the activator;

continuously measuring cell adhesion or attachment of the viable cancer cells in the portion of the sample contacted with a higher concentration of the activator, relative to the portion of the sample contacted with the lower concentration of the activator;

determining by mathematical analysis of the continuous measurements the sensitivity of the signaling pathway to the activator; and administering to the subject at least one targeted therapeutic that selectively affects the same signaling pathway the activator affects when the signaling pathway is ultra-sensitive to the activator, indicating the signaling pathway is abnormally active in the subject's cancer cells.

In one embodiment, the method comprises:

continuously measuring cell adhesion or attachment of the viable cancer cells in the portion of the sample contacted with a higher concentration of the activator, relative to the portion of the sample contacted with a lower concentration of the activator, and relative to a portion of the sample that has not been contacted with the activator;

determining by mathematical analysis of the continuous measurements sensitivity of the sample to the activator and an output value for the activator that characterizes whether a change in cell adhesion or attachment has occurred in the portions of the sample contacted with the activator, as compared to the portion of the sample not contacted with the activator; and administering to the subject at least one targeted therapeutic that selectively affects the same signaling pathway the activator affects when the signaling pathway is ultra-sensitive to the activator, indicating the signaling pathway is abnormally active in the subject's cancer cells or when the output value for the activator is greater than a pre-determined cut-off value.

In another aspect, the invention pertains to a method of identifying a targeted therapeutic that selectively affects an abnormally active signaling pathway in a subject's cancer cells, the method comprising:

culturing a sample comprising viable cancer cells obtained from the subject;

contacting the sample with an activator that is known to selectively affect a signaling pathway, so as to upregulate or downregulate the signaling pathway as measured by an effect on cell adhesion or attachment, wherein a portion of the sample is contacted with a higher concentration of the activator and a portion of the sample is contacted with a lower concentration of the activator;

continuously measuring cell adhesion or attachment of the viable cancer cells in the portion of the sample contacted with a higher concentration of the activator, relative to the portion of the sample contacted with the lower concentration of the activator;

determining by mathematical analysis of the continuous measurements the sensitivity of the signaling pathway to the activator; and identifying a targeted therapeutic that selectively affects the same signaling pathway the activator affects when the signaling pathway is ultra-sensitive to the activator, indicating the signaling pathway is abnormally active in the subject's cancer cells.

In one embodiment, the method comprises:

continuously measuring cell adhesion or attachment of the viable cancer cells in the portion of the sample contacted with a higher concentration of the activator, relative to the portion of the sample contacted with a lower concentration of the activator, and relative to a portion of the sample that has not been contacted with the activator;

determining by mathematical analysis of the continuous measurements sensitivity of the sample to the activator and an output value for the activator that characterizes whether a change in cell adhesion or attachment has occurred in the portions of the sample contacted with the activator, as compared to the portion of the sample not contacted with the activator; and identifying a targeted therapeutic that selectively affects the same signaling pathway the activator affects when the signaling pathway is ultra-sensitive to the activator, indicating the signaling pathway is abnormally active in the subject's cancer cells or when the output value for the activator is greater than a pre-determined cut-off value.

In one embodiment, the higher concentration of the activator is EC90 (i.e., an Effective Concentration 90) and the lower concentration of the activator is EC10 (i.e., an Effective Concentration 10). As used herein, an EC90 is that concentration of activator that gives 90% of the maximal response for the activator on the subject's cells. As used herein, the EC10 is that concentration of activator that gives 10% of the maximal response for the activator on the subject's cells. In one embodiment, an EC90:EC10 ratio of less than 81 indicates that the signaling pathway is ultra-sensitive to the activator.

In other embodiments, the higher concentration of the activator is 2-fold, 3-fold, 4-fold, 5-fold, 10-fold, 20-fold, 30-fold, 40-fold, 50-fold, 60-fold, 70-fold or more up to 80-fold more than the lower concentration of the activator.

In another embodiment, the higher concentration of the activator is the only concentration that is used and is determined from comparing results of a small population of patients who are ultra-sensitive with a small population of patients who are not ultra-sensitive by any of the embodiments described herein. Accordingly, in another embodiment, the methods of the disclosure involving measuring signaling pathway ultrasensitivity comprise a contacting step (between the culturing step and the continuously measuring cell adhesion or attachment step) of contacting the sample with an activator that is known to selectively affect a signaling pathway, so as to upregulate or downregulate the signaling pathway as measured by an effect on cell adhesion or attachment, wherein the concentration of the activator used is a concentration that has been determined to identify ultrasensitivity of the signaling pathway.

In one embodiment, the sensitivity of the signaling pathway to the activator is determined using the Hill equation to determine a Hill Coefficient.

The Hill equation is known in the art and can be expressed most simply as:

$$\text{Output} = \frac{\text{Input}^n}{K^n + \text{Input}^n} \text{ And } n = \frac{\text{Log}[81]}{\text{Log}[EC90/EC10]}$$

wherein:

Input is the input concentration. It can be expressed in many different forms such as pM, nM, µM, mM, M, ng/mL, %, etc.

$K_{0.5}$ is the half-maximal concentration constant. It may also be referred to as $K_{half}$. It is the substrate concentration that gives rise to a reaction that is 50% complete.

n is the Hill coefficient.

In one embodiment, a Hill Coefficient value of greater than one indicates that the signaling pathway is ultra-sensitive to the activator.

The Hill equation expressed in an alternative manner:

$$\theta = \frac{[L]^n}{K_d + [L]^n}$$

wherein:

Θ—Fraction of the activity derived from the pathway.

[L]—Free (unbound) ligand (activator) concentration.

$K_d$—Apparent dissociation constant derived from the law of mass action (the equilibrium constant for dissociation), which is equal to the ratio of the dissociation rate of the ligand-receptor complex to its association rate $$\left(K_d = \frac{k_d}{k_a}\right).$$

n—the Hill coefficient.

One practiced in the art would recognize that the equation above is useful in creating a linear plot of log $$\left(\frac{\theta}{1-\theta}\right)$$

versus log L that yields a linear plot wherein the slope is n, the Hill coefficient.

One practiced in the art would also recognize that $EC_{90}/EC_{10} < 81$ represents an ultrasensitive signaling instance, wherein the smaller the $EC_{90}/EC_{10}$ ratio, the greater the ultrasensitivity.

In one embodiment, the signaling pathways are selected from the group consisting of HER2/HER1, HER1, HER2/HER3, HER3, c-Met/HGFR, ALK, FGFR, IGFR, EGFR, FLT3, Axl, PDGFR, SMO, Patched 1, Frizzled and Notch.

In one embodiment, the signaling pathways are selected from the group consisting of HER2/HER1, HER1, HER2/HER3, HER3, c-Met/HGF, ALK, ROS, FGFR, IGFR, EGFR, FLT3, Axl, Tyro3, Mer, PDGFR, SMO, Patched 1, Frizzled, Notch, MAPK, RON, RHO, AKT, FAK1, RAS, RAF, PI3K/PTEN, MAK, MKK, MEK, MEKK, Mos, Erk, MLK, MLK3, TAK, DLK, p38, ASK, SAPK, JNK, BMK, PKC, PI3K, PIK3/PTEN, Bad, Bcl, Bak, Bax, BID, Bim, Noxa, Puma, BH3, caspase, p53, NIK, NFkB, ROCK, XIAP, MOMP, ILK, PDK, insulin receptor (IR), IGFR, mTOR, Jak, PIKK, 4E-BP1, Raptor, KMT, MLL, KDM, UTX, DOT1L, BRD, TET, SirT1, Hat, SNF, DNMT, EZH, AMPK, PLC, CaMKK, glucose transporter, PFK, FAS, Krebs Cycle, glycolysis, TNFR, TRAD, TRAF, TAB, NEMO, NIK, IKK, RelA, RelB, kB, IL1R, IRAK, Myd88, TRADD, FADD, FLIPs, ICAD, CAD, PARP, lamins, ZNRF, WntR, PAR, GSK, Dsh, LGR, catenin, WTX, APC, Src, CBP, Fringe, Furin, Delta Jagged, NIC, presenilin, CDO, BOC, Gli, KIF, cyclin D, cyclin E, SARA, Smad, Smurf, NLK, p28, Myc, Max, Fos, Jun, LIMK, cofilin, CD44, FAT, KIBRA, FRMD, Mst, YAP, LATS, MOB, SAV, TEAD, Mer, SAB, TAZ, Rho, Rac, PAK, CREB, HER2, HER3, HER4, estrogen receptors, progesterone receptors, androgen receptors, GPER30, VEGF receptor, TGFbeta/SMAD, WNT, Hedgehog/GLI, HIF1 alpha, JAK/STAT, control of G1/S transition, DNA damage control, and apoptosis.

In one embodiment, the signaling pathway is a HER family signaling pathway. In one embodiment, the HER family signaling pathway is a HER2 signaling pathway. In one embodiment, the HER family signaling pathway is a HER3 signaling pathway. In one embodiment, the HER family signaling pathway is an EGFR signaling pathway. In one embodiment, the signaling pathway is the HER3 signaling pathway and ultrasensitivity is tested using different concentrations of neuregulin as the activator agent (as described further in Example 2). In another embodiment, the signaling pathway is the EGFR signaling pathway and ultrasensitivity is tested using different concentrations of amphiregulin, betacullulin, HB-EGF or TGF-alpha as the activator agent (as described further in Example 2).

In one embodiment, the at least one targeted therapeutic is selected from the group consisting of cetuximab, erlotinib, gefitinib, lapatinib, pazopanib, trastuzumab, fulvestrant, tamoxifen, letrozole, anastrozole, exemestane, everolimus, abiraterone, bicalutamide, bortezomib, vemurafenib, ipilimumab, Pertuzumab, MEDI4276, ONT-380, Neratinib, Afatinib, Duligotuzumab, Dacomitinib, Sapitinib, Poziotinib, ASLAN001, MM-111 MM-121, MM-141, LJM716, U3-1287 (AMG 888), TK-A3/TK-A4, Lumretuzumab, REGN1400, AV-203, AZD5363, Afuresertib, MK-2206, Ipatasertib, Ridaforolimus, Temsirolimus, Selemetinib, Cobimetinib, GDC-0994, Taselisib, Alpelisib, Buparlisib, AZD8186, AZD8835, Panitumumab, REGN955, MM-151, Osimertinib, Rociletinib, AZD5363, SGX-523, Onartuzumab, Cabozantinib, Volitinib, Tivantinib, Capmatinib, Emibetuzumab, Rilotumumab, Ficlatuzumab, SAR125844, emibetuzumab, Sym015, AMG337, JNJ-61186372, glesatinib, 1202, LY3023414, Gedatolisib, JI-101, Ponatinib, Sunitinib, Crizotinib, Ceritinib, Brigatinib, Alectinib, BGJ398, Linsitinib, Quizartinib, R428 (BGB324), Gilteritnib, Vismodegib, Itraconazole, 5E1, LGK974, Semagacestat, Cobimetinib, AZD4547, JNJ-42756493, Dalotuzumab, MEDI-573, Ganitumab, Sonidegib, Vantictumab, Ipafricept, Tarextumab, Brontictuzumab, SB431542, EW-7197, RepSox, AZD9291, Rociletinib, abraxane, brentuximab vedoton, ofatumumab, bevacizumab, alemtuzumab, bicalutamide, gemcitabine, imatinib, ixabepilone, romidepsin, cabrazitaxel, sorafenib, infliximab, lenalidomide, rituximab, dasatinib, nilotinib, temozolomide, bortezomib, azacitidine, tepotinib, lorlatinib, merestinib, RG6114, tucantinib, pazopanib, crizotinib, vemurafenib, goserelin acetate, abiraterone, a BH3 mimetic, navitoclax, anastrozole, letrozole, an aromatase inhibitor, ixabepilone, aflibercept, temsirolimus, irbritumomab, abiraterone, custirsen, enzalutamide, nivolumab, palbociclib, regorafenib, entinostat, ARN-509, ARN-810, BIND-014, dabrafenib, daratumumab, lambrolizumab, LDK378, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof.

Various suitable targeted therapeutics, activators and signaling pathways are also described further in the subsections below and in the Examples.

In one embodiment, the activator in each paired set of agents is a protein, peptide, nucleic acid, metabolite, ligand, reagent, organic molecule, signaling factor, growth factor, biochemical, or combinations thereof. Examples of suitable activators are described further in the subsections below.

In one embodiment, cell adhesion or attachment is measured using an impedance biosensor or an optical biosensor. Use of biosensors is described in further detail in the subsections below.

In one embodiment, the cancer is selected from the group consisting of breast cancer, lung cancer, colorectal cancer, bladder cancer, kidney cancer, ovarian cancer and leukemia. Additional suitable cancers are described in the subsections below.

In one embodiment, the sample of viable cancer cells is cultured in a media comprising growth factors and free of serum. In another embodiment, the sample of viable cancer cells is also cultured in a media comprising an anti-apoptotic agent and free of serum. Culture conditions and culturing of cells is described in further detail in the subsections below.

D. Methods of Using Multiple Activators of the Same Signaling Pathway

In another aspect of the invention, the method used to select the targeted therapeutic agent for treatment of a cancer patient involves evaluating the amount of activity simultaneously initiated in a patient's cells by at least two signaling pathway activators that a single targeted therapeutic agent can inhibit. Since signaling pathway activity may be driven by upstream activity initiated by more than one cell surface receptor, it is advantageous to evaluate the antagonist effect of a therapy targeting such a pathway node. For example, this approach allows for measurement of the affect a therapeutic targeting a downstream pathway node (e.g. AKT, PI3K, MEK, ERK, mTOR) has on signaling pathway activity downstream of multiple cell surface receptors. By evaluating the simultaneous effect of two or more signaling pathway activators in a patient's cells downstream of the signal activation point, this approach improves on methods that evaluate the effect of a pair of signaling pathway activator and targeted therapeutic agents have in the patient's cells.

Accordingly, in one aspect, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample with at least one triplet set of agents, each triplet set comprised of a first agent targeted therapeutic and at least two second agent activators that are known to selectively affect the same signaling pathway the targeted therapeutic is intended to address, so as to upregulate or downregulate the signaling pathway as measured by an effect on cell adhesion or attachment, to produce a sample contacted with at least one triplet set of agents;

continuously measuring cell adhesion or attachment of the viable cancer cells in the sample contacted with the at least one triplet set of agents, relative to a sample of viable cancer cells obtained from the subject that is contacted with the first agent targeted therapeutic or each of the second agent activators alone;

determining by mathematical analysis of the continuous measurements an output value for the at least one triplet set of agents that characterizes whether a change in cell adhesion or attachment has occurred in the sample contacted with the triplet set of agents, as compared to the sample contacted with the first agent targeted therapeutic or the second agent activators alone; and administering to the subject at least one targeted therapeutic that affects the same signaling pathway as the first agent targeted therapeutic from the triplet set of agents when the output value is greater than a pre-determined cut-off value indicating the targeted therapeutic agent is therapeutically active in the cell signaling pathway of the subject's cancer cells.

In one embodiment, the targeted therapeutic that is administered to the subject is the first agent targeted therapeutic. In another embodiment, the targeted therapeutic that is administered to the subject is different than the first agent targeted therapeutic but targets the same signaling pathway as said first agent targeted therapeutic.

In another aspect, the invention pertains to a method of identifying a targeted therapeutic that is therapeutically active in the signaling pathway it is intended to address in a subject's cancer cells, the method comprising:

culturing a sample comprising viable cancer cells obtained from the subject;

contacting the sample with at least one triplet set of agents, each triplet set comprised of a targeted therapeutic and at least two activators that are known to selectively affect the same signaling pathway the targeted therapeutic is intended to address, so as to upregulate or downregulate the signaling pathway as measured by an effect on cell adhesion or attachment, to produce a sample contacted with at least one triplet set of agents;

continuously measuring cell adhesion or attachment of the viable cancer cells in the sample contacted with the at least one triplet set of agents, relative to a sample of viable cancer cells obtained from the subject that is contacted with the targeted therapeutic or each of the activators alone;

determining by mathematical analysis of the continuous measurements an output value for the at least one triplet set of agents that characterizes whether a change in cell adhesion or attachment has occurred in the sample contacted with the triplet set of agents, as compared to the sample contacted with the targeted therapeutic or the activators alone; and identifying the targeted therapeutic from the triplet set of agents when the output value is greater than a pre-determined cut-off value indicating the targeted therapeutic agent is therapeutically active in the cell signaling pathway of the subject's cancer cells.

In one embodiment, the targeted therapeutic (e.g., first agent targeted therapeutic) is determined to have an output value percentage greater than 50% indicating the signaling pathway affected by the targeted therapeutic is active in the subject's cancer cells. In another embodiment, the targeted therapeutic (e.g., first agent targeted therapeutic) is determined to have an output value percentage greater than 50% indicating the targeted therapeutic is therapeutically active in the cell signaling pathway of the subject's cancer cells.

In one embodiment, the signaling pathways are selected from the group consisting of HER2/HER1, HER1, HER2/HER3, HER3, c-Met/HGF, ALK, FGFR, IGFR, EGFR, FLT3, Axl, PDGFR, SMO, Patched 1, Frizzled and Notch.

In one embodiment, the signaling pathways are selected from the group consisting of HER2/HER1, HER1, HER2/HER3, HER3, c-Met/HGF, ALK, ROS, FGFR, IGFR, EGFR, FLT3, Axl, Tyro3, Mer, PDGFR, SMO, Patched 1, Frizzled, Notch, MAPK, RON, RHO, AKT, FAK1, RAS, RAF, PI3K/PTEN, MAK, MKK, MEK, MEKK, Mos, Erk, MLK, MLK3, TAK, DLK, p38, ASK, SAPK, JNK, BMK, PKC, PI3K, PIK3/PTEN, Bad, Bcl, Bak, Bax, BID, Bim, Noxa, Puma, BH3, caspase, p53, NIK, NFkB, ROCK, XIAP, MOMP, ILK, PDK, insulin receptor (IR), IGFR, mTOR, Jak, PIKK, 4E-BP1, Raptor, KMT, MLL, KDM, UTX, DOT1L, BRD, TET, SirT1, Hat, SNF, DNMT, EZH, AMPK, PLC, CaMKK, glucose transporter, PFK, FAS, Krebs Cycle, glycolysis, TNFR, TRAD, TRAF, TAB, NEMO, NIK, IKK, RelA, RelB, kB, IL1R, IRAK, Myd88, TRADD, FADD, FLIPs, ICAD, CAD, PARP, lamins, ZNRF, WntR, PAR, GSK, Dsh, LGR, catenin, WTX, APC, Src, CBP, Fringe, Furin, Delta Jagged, NIC, presenilin, CDO, BOC, Gli, KIF, cyclin D, cyclin E, SARA, Smad, Smurf, NLK, p28, Myc, Max, Fos, Jun, LIMK, cofilin, CD44, FAT, KIBRA, FRMD, Mst, YAP, LATS, MOB, SAV, TEAD, Mer, SAB, TAZ, Rho, Rac, PAK, CREB, HER2, HER3, HER4, estrogen receptors, progesterone receptors, androgen receptors, GPER30, VEGF receptor, TGFbeta/SMAD, WNT, Hedgehog/GLI, HIF1 alpha, JAK/STAT, control of G1/S transition, DNA damage control, and apoptosis.

In one embodiment, the signaling pathway is a HER family signaling pathway. In one embodiment, the HER family signaling pathway is a HER2 signaling pathway.

In one embodiment, the at least one targeted therapeutic is selected from the group consisting of cetuximab, erlotinib, gefitinib, lapatinib, pazopanib, trastuzumab, fulvestrant, tamoxifenletrozole, anastrozole, exemestane, everolimus, abiraterone, bicalutamide, bortezomib, vemurafenib, ipilimumab, Pertuzumab, MEDI4276, ONT-380, Neratinib, Afatinib, Duligotuzumab, Dacomitinib, Sapitinib, Poziotinib, ASLAN001, MM-111 MM-121, MM-141, LJM716, U3-1287 (AMG 888), TK-A3/TK-A4, Lumretuzumab, REGN1400, AV-203, AZD5363, Afuresertib, MK-2206, Ipatasertib, Ridaforolimus, Temsirolimus, Selemetinib, Cobimetinib, GDC-0994, Taselisib, Alpelisib, Buparlisib, AZD8186, AZD8835, Panitumumab, REGN955, MM-151, Osimertinib, Rociletinib, AZD5363, SGX-523, Onartuzumab, Cabozantinib, Volitinib, Tivantinib, Capmatinib, Emibetuzumab, Rilotumumab, Ficlatuzumab, SAR125844, emibetuzumab, Sym015, AMG337, JNJ-61186372, glesatinib, 1202, LY3023414, Gedatolisib, JI-101, Ponatinib, Sunitinib, Crizotinib, Ceritinib, Brigatinib, Alectinib, BGJ398, Linsitinib, Quizartinib, R428 (BGB324), Gilteritinib, Vismodegib, Itraconazole, 5E1, LGK974, Semagacestat, Cobimetinib, AZD4547, JNJ-42756493, Dalotuzumab, MEDI-573, Ganitumab, Sonidegib, Vantictumab, Ipafricept, Tarextumab, Brontictuzumab, SB431542, EW-7197, RepSox, AZD9291, Rociletinib, abraxane, brentuximab vedoton, ofatumumab, bevacizumab, alemtuzumab, bicalutamide, gemcitabine, imatinib, ixabepilone, romidepsin, cabrazitaxel, sorafenib, infliximab, lenalidomide, rituximab, dasatinib, nilotinib, temozolomide, bortezomib, azacitidine, tepotinib, lorlatinib, merestinib, RG6114, tucantinib, pazopanib, crizotinib, vemurafenib, goserelin acetate, abiraterone, a BH3 mimetic, navitoclax, anastrozole, letrozole, an aromatase inhibitor, ixabepilone, aflibercept, temsirolimus, irbritumomab, abiraterone, custirsen, enzalutamide, nivolumab, palbociclib, regorafenib, entinostat, ARN-509, ARN-810, BIND-014, dabrafenib, daratumumab, lambrolizumab, LDK378, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof.

Various suitable targeted therapeutics, activators and signaling pathways are also described further in the subsections below and in the Examples.

In one embodiment, each activator in each triplet set of agents is a protein, peptide, nucleic acid, metabolite, ligand, reagent, organic molecule, signaling factor, growth factor, biochemical, or combinations thereof. In certain embodiments of the triplet sets of agents, one of the triplet set of agents is the activator NRG1 that affects the HER3 (PI3K) pathway, one of the triplet set of agents is the activator HGF that affects the HGF pathway, and one of the triplet set of agents is the therapeutic agent, Taselisib, that targets the PI3k pathway node and affects both the HER3 and HGFR pathways Additional examples of suitable activators are described further in the subsections below and in the Examples.

In one embodiment, cell adhesion or attachment is measured using an impedance biosensor or an optical biosensor. Use of biosensors is described in further detail in the subsections below.

In one embodiment, the cancer is selected from the group consisting of breast cancer, lung cancer, colorectal cancer, bladder cancer, kidney cancer, ovarian cancer and leukemia. Additional suitable cancers are described in the subsections below.

In one embodiment, the sample of viable cancer cells is cultured in a media comprising growth factors and free of serum. In another embodiment, the sample of viable cancer cells is also cultured in a media comprising an anti-apoptotic agent and free of serum. Culture conditions and culturing of cells is described in further detail in the subsections below.

E. Methods of Targeting Different Binding Sites within a Signaling Pathway

In another aspect of the invention, the method used to select the targeted therapeutic agent for treatment of a cancer patient involves evaluating a targeted therapeutic that affects a different point or node or binding site within the same or a different signaling pathway than an activator that is used to stimulate the signaling pathway. The methods used to select the targeted therapeutic agent for treatment of a cancer patient involve evaluating the amount of activity initiated in a patient's cells by one or more (e.g., two) signaling pathway activators and inhibited by a targeted therapeutic agent that does not directly target the same approximate binding site as the activator. Since two or more signaling pathways may be interconnected with multiple points of convergence, crosstalk and feedback loops, a targeted therapeutic designed to inhibit pathway activity initiated at the activator binding site (e.g. cell surface receptor) may not be the most effective way of inhibiting the signaling pathway activity. In cases where signaling pathway activity initiated by an activator agent cannot be inhibited by a matching signaling pathway inhibitor directly targeting the same approximate binding site as the activator, a therapy targeting a different binding site than the binding site of the activator may be able to inhibit the initiated signaling pathway activity. This approach allows for measurement of the affect a therapeutic targeting a binding site downstream (e.g. AKT, PI3K, MEK, ERK, mTOR), upstream (e.g. RAS, RAF), or lateral (e.g. Hedgehog, Notch, Wnt, c-MET, ALK, AXL, FGFR) to the binding site of the activator agent has on signaling pathway activity initiated by the activator agent. By evaluating the effect of a signaling pathway inhibitor downstream, upstream, or lateral to the activation binding site of an activator agent in a patient's cells, this approach improves on methods that evaluate the effect of a pair of signaling pathway activator and targeted therapeutic agents have at the same approximate binding site in the patient's cells. Additionally, the present invention includes therapeutic agents that are known and can be found that bind to and regulate multiple nodes or targets. Thus, treating a patient with a targeted therapeutic that binds to different binding site than an activator agent can lead to superior efficacy and better clinical outcomes.

Accordingly, in one embodiment, the invention provides a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample with (i) a first agent activator that affects a signaling pathway, wherein the activator has an activation binding site, and (ii) a second agent targeted therapeutic agent that affects the same signaling pathway as the activator but at a binding site downstream, upstream or lateral to the activation binding site, so as to upregulate or downregulate the signaling pathway as measured by an effect on cell adhesion or attachment, to produce a sample contacted with the first agent and the second agent;

continuously measuring cell adhesion or attachment of the viable cancer cells in the sample contacted with the first agent and second agent, relative to a sample of viable cancer cells obtained from the subject that is contacted with the first agent or the second agent alone;

determining by mathematical analysis of the continuous measurements an output value that characterizes whether a change in cell adhesion or attachment has occurred in the sample contacted with both the first agent and the second agent, as compared to the sample contacted with the first agent or the second agent alone; and administering to the subject at least one targeted therapeutic that affects the same signaling pathway that the second agent targeted therapeutic affects, wherein the output value that characterizes the change in cell adhesion or attachment is equal to or greater than a cut-off value indicating the signaling pathway is active in the subject's cancer cells.

In one embodiment, the targeted therapeutic that is administered to the subject is the second agent targeted therapeutic. In another embodiment, the targeted therapeutic that is administered to the subject is different than the second agent targeted therapeutic but targets the same signaling pathway as said second agent.

In another aspect, the invention provides a method of identifying a targeted therapeutic that is therapeutically active in the signaling pathway it is intended to address in a subject's cancer cells, the method comprising:

culturing a sample comprising viable cancer cells obtained from the subject;

contacting the sample with (i) a first agent activator that affects a signaling pathway, wherein the activator has an activation binding site, and (ii) a second agent targeted therapeutic agent that affects the same signaling pathway as the activator but at a binding site downstream, upstream or lateral to the activation binding site, so as to upregulate or downregulate the signaling pathway as measured by an effect on cell adhesion or attachment, to produce a sample contacted with the first agent and the second agent;

continuously measuring cell adhesion or attachment of the viable cancer cells in the sample contacted with the first agent and second agent, relative to a sample of viable cancer cells obtained from the subject that is contacted with the first agent or the second agent alone;

determining by mathematical analysis of the continuous measurements an output value that characterizes whether a change in cell adhesion or attachment has occurred in the sample contacted with both the first agent and the second agent, as compared to the sample contacted with the first agent or the second agent alone; and identifying the second agent targeted therapeutic as therapeutically active in the signaling pathway it is intended to address in the subject's cancer cells, wherein the output value that characterizes the change in cell adhesion or attachment is equal to or greater than a cut-off value indicating the signaling pathway is active in the subject's cancer cells and/or that the second agent targeted therapeutic as therapeutically active in the signaling pathway it is intended to address in the subject's cancer cells.

In another embodiment of these methods for probing different binding sites (e.g., points or nodes) within a signaling pathway, multiple activator agents (two or more), each having an activation binding site within the signaling pathway or interest are used in combination with a targeted therapeutic agent that affects the same signaling pathway as the activators but at a binding site downstream, upstream or lateral to the activation binding sites of the activators. Accordingly, in another embodiment, the invention provides a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample with (i) two or more first agent activator that affects a signaling pathway, wherein each activator has an activation binding site, and (ii) a second agent targeted therapeutic agent that affects the same signaling pathway as the two or more first agent activators but at a binding site downstream, upstream or lateral to the activation binding sites of the activators, so as to upregulate or downregulate the signaling pathway as measured by an effect on cell adhesion or attachment, to produce a sample contacted with the first agents and the second agent;

continuously measuring cell adhesion or attachment of the viable cancer cells in the sample contacted with the first agents and second agent, relative to a sample of viable cancer cells obtained from the subject that is contacted with the first agents or the second agent alone;

determining by mathematical analysis of the continuous measurements an output value that characterizes whether a change in cell adhesion or attachment has occurred in the sample contacted with both the first agents and the second agent, as compared to the sample contacted with the first agents or the second agent alone; and administering to the subject at least one targeted therapeutic that affects the same signaling pathway that the second agent targeted therapeutic affects, wherein the output value that characterizes the change in cell adhesion or attachment is equal to or greater than a cut-off value indicating the signaling pathway is active in the subject's cancer cells.

In one embodiment, the targeted therapeutic that is administered to the subject is the second agent targeted therapeutic. In another embodiment, the targeted therapeutic that is administered to the subject is different than the second agent targeted therapeutic but targets the same signaling pathway as said second agent.

In another aspect, the invention provides a method of identifying a targeted therapeutic that is therapeutically active in the signaling pathway it is intended to address in a subject's cancer cells, the method comprising:

culturing a sample comprising viable cancer cells obtained from the subject;

contacting the sample with (i) two or more first agent activators that affects a signaling pathway, wherein each activator has an activation binding site, and (ii) a second agent targeted therapeutic agent that affects the same signaling pathway as the two or more first agent activators but at a binding site downstream, upstream or lateral to the activation binding sites of the activators, so as to upregulate or downregulate the signaling pathway as measured by an effect on cell adhesion or attachment, to produce a sample contacted with the first agents and the second agent;

continuously measuring cell adhesion or attachment of the viable cancer cells in the sample contacted with the first agents and second agent, relative to a sample of viable cancer cells obtained from the subject that is contacted with the first agents or the second agent alone;

determining by mathematical analysis of the continuous measurements an output value that characterizes whether a change in cell adhesion or attachment has occurred in the sample contacted with both the first agents and the second agent, as compared to the sample contacted with the first agents or the second agent alone; and identifying the second agent targeted therapeutic as therapeutically active in the signaling pathway it is intended to address in the subject's cancer cells, wherein the output value that characterizes the change in cell adhesion or attachment is equal to or greater than a cut-off value indicating the signaling pathway is active in the subject's cancer cells and/or that the second agent targeted therapeutic as therapeutically active in the signaling pathway it is intended to address in the subject's cancer cells.

In one embodiment, the signaling pathways are selected from the group consisting of HER2/HER1, HER1, HER2/HER3, HER3, c-Met/HGF, ALK, FGFR, IGFR, EGFR, FLT3, Axl, PDGFR, SMO, Patched 1, Frizzled and Notch.

In various embodiments of these methods, the signaling pathway is selected from the group consisting of HER2/HER1, HER1, HER2/HER3, HER3, c-Met/HGF, ALK, ROS, FGFR, PDGFR, IGFR, EGFR, FLT3, Axl, Tyro3, Mer, SMO, Patched 1, Frizzled, Notch, MAPK, RON, RHO, AKT, FAK1, RAS, RAF, PI3K/PTEN, MAK, MKK, MEK, MEKK, Mos, Erk, MLK, MLK3, TAK, DLK, p38, ASK, SAPK, JNK, BMK, PKC, PI3K, PIK3/PTEN, Bad, Bcl, Bak, Bax, BID, Bim, Noxa, Puma, BH3, caspase, p53, NIK, NFkB, ROCK, XIAP, MOMP, ILK, PDK, insulin receptor (IR), IGFR, mTOR, Jak, PIKK, 4E-BP1, Raptor, KMT, MLL, KDM, UTX, DOT1L, BRD, TET, SirT1, Hat, SNF, DNMT, EZH, AMPK, PLC, CaMKK, glucose transporter, PFK, FAS, Krebs Cycle, glycolysis, TNFR, TRAD, TRAF, TAB, NEMO, NIK, IKK, RelA, RelB, kB, IL1R, IRAK, Myd88, TRADD, FADD, FLIPs, ICAD, CAD, PARP, lamins, ZNRF, WntR, PAR, GSK, Dsh, LGR, catenin, WTX, APC, Src, CBP, Fringe, Furin, Delta Jagged, NIC, presenilin, CDO, BOC, Gli, KIF, cyclin D, cyclin E, SARA, Smad, Smurf, NLK, p28, Myc, Max, Fos, Jun, LIMK, cofilin, CD44, FAT, KIBRA, FRMD, Mst, YAP, LATS, MOB, SAV, TEAD, Mer, SAB, TAZ, Rho, Rac, PAK, CREB, HER2, HER3, HER4, estrogen receptors, progesterone receptors, androgen receptors, GPER30, VEGF receptor, TGFbeta/SMAD, WNT, Hedgehog/GLI, HIF1 alpha, JAK/STAT, control of G1/S transition, DNA damage control, and apoptosis.

In various embodiments, the first agent activator(s) is a protein, peptide, nucleic acid, metabolite, ligand, reagent, organic molecule, signaling factor, growth factor, biochemical, or combinations thereof.

In one embodiment, cell adhesion or attachment is measured using an impedance biosensor or an optical biosensor. Use of biosensors is described in further detail in the subsections below.

In one embodiment, the cancer is selected from the group consisting of breast cancer, lung cancer, colorectal cancer, bladder cancer, kidney cancer, ovarian cancer and leukemia. Additional suitable cancers are described in the subsections below.

In one embodiment, the sample of viable cancer cells is cultured in a media comprising growth factors and free of serum. In one embodiment, the sample of viable cancer cells is also cultured in a media comprising an anti-apoptotic agent and free of serum. Culture conditions and culturing of cells is described in further detail in the subsections below.

In one embodiment, the at least one targeted therapeutic that is administered to the subject is selected from the group consisting of cetuximab, erlotinib, gefitinib, lapatinib, pazopanib, trastuzumab, fulvestrant, tamoxifen, letrozole, anastrozole, exemestane, everolimus, abiraterone, bicalutamide, bortezomib, vemurafenib, ipilimumab, Pertuzumab, MEDI4276, ONT-380, Neratinib, Afatinib, Duligotuzumab, Dacomitinib, Sapitinib, Poziotinib, ASLAN001, MM-111 MM-121, MM-141, LJM716, U3-1287 (AMG 888), TK-A3/TK-A4, Lumretuzumab, REGN1400, AV-203, AZD5363, Afuresertib, MK-2206, Ipatasertib, Ridaforolimus, Temsirolimus, Selemetinib, Cobimetinib, GDC-0994, Taselisib, Alpelisib, Buparlisib, AZD8186, AZD8835, Panitumumab, REGN955, MM-151, Osimertinib, Rociletinib, AZD5363, SGX-523, Onartuzumab, Cabozantinib, Volitinib, Tivantinib, Capmatinib, Emibetuzumab, Rilotumumab, Ficlatuzumab, SAR125844, emibetuzumab, Sym015, AMG337, JNJ-61186372, glesatinib, 1202, LY3023414, Gedatolisib, JI-101, Ponatinib, Sunitinib, Crizotinib, Ceritinib, Brigatinib, Alectinib, BGJ398, Linsitinib, Quizartinib, R428 (BGB324), gilteritinib, Vismodegib, Itraconazole, 5E1, LGK974, Semagacestat, Cobimetinib, AZD4547, JNJ-42756493, Dalotuzumab, MEDI-573, Ganitumab, Sonidegib, Vantictumab, Ipafricept, Tarextumab, Brontictuzumab, SB431542, EW-7197, RepSox, AZD9291, Rociletinib, abraxane, brentuximab vedoton, ofatumumab, bevacizumab, alemtuzumab, bicalutamide, gemcitabine, imatinib, ixabepilone, romidepsin, cabrazitaxel, sorafenib, infliximab, lenalidomide, rituximab, dasatinib, nilotinib, temozolomide, bortezomib, azacitidine, tepotinib, lorlatinib, merestinib, RG6114, tucantinib, pazopanib, crizotinib, vemurafenib, goserelin acetate, abiraterone, a BH3 mimetic, navitoclax, anastrozole, letrozole, an aromatase inhibitor, ixabepilone, aflibercept, temsirolimus, irbritumomab, abiraterone, custirsen, enzalutamide, nivolumab, palbociclib, regorafenib, entinostat, ARN-509, ARN-810, BIND-014, dabrafenib, daratumumab, lambrolizumab, LDK378, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof.

Various suitable targeted therapeutics, activators and signaling pathways are also described further in the subsections below and in the Examples.

F. Simultaneous Activation and Inhibition of Multiple Signaling Pathways

When targeted therapeutics are selected using genomic or histological analyses, often they are generally prescribed one at a time to an individual patient and only a small percentage of the resulting treated disease patient population may have cells with the disease process the single targeted therapeutic is intended to effect. This has limited the usage of many efficacious targeted therapeutics in the marketplace or even prevented targeted therapeutics from obtaining the regulatory approvals required to market them. One response by pharmaceutical companies and physicians has been to test combinations of targeted therapeutics. There are many trials underway to treat patients with two or more targeted therapies, where each targeted therapy is intended to affect a different aspect of dysfunctional signaling in a single patient. Many of these are also unsuccessful. No objective clinical measure has been described to date to assess combinations of targeted therapies for a patient before administering the combination to that patient. Multiple problems arise when no objective method exists to determine that two or more dysfunctional signaling issues are present in that patient and whether two or more targeted therapeutics are warranted as efficacious. A description of the different issues the present invention is designed to address with respect to treatment of patients with combined targeted therapeutics is described herein.

If each of the two or more targeted therapeutics prescribed as single agents are actually only therapeutically active in distinct and separate sub-groups of the disease population, the outcome within the total population may be assumed to be greater for those patients treated with two or more therapeutics relative to the same population treated with only one of the targeted therapeutics. For example, if each of two targeted therapies has an objective response rate of 10% on a patient population when they are prescribed individually, the objective response rate may increase to 20% when they are prescribed in combination. The resulting improved outcomes for the population receiving the combination of targeted therapeutics may be sufficient to increase usage of each therapeutic in the marketplace or to gain regulatory approval for the combination treatment in cases where neither or only one of the therapeutics would have otherwise obtained approval. Despite the improved outcomes for the population as a whole, many or all patients in the population may receive at least one therapeutic that is not therapeutically active in their tumor cells and a smaller, but still significant proportion of the population may receive two therapeutics neither of which is therapeutically active in their tumor cells. The outcome is an increased risk of harm for all patients given the combination. This approach can thus lead to greater numbers of patients receiving targeted therapeutics that provide no therapeutic benefit and their associated, often toxic, side effects, than they would have received had they been treated with only a single targeted therapeutic. So, while it can be advantageous to prescribe two or more targeted therapeutics to a patient to increase the odds of success in a population, an alternative approach is required that more accurately assigns the treatment of individual patients with targeted therapeutics, especially in cases of treatments of combined targeted therapeutics.

The methods described herein make it possible to determine a priori whether one or more targeted therapeutics is therapeutically active in a patient's cells to improve the selection of the targeted therapeutic used to treat a patient. In one aspect of the invention, the method used to select one or more targeted therapeutic agents for treatment of a cancer patient involves evaluating the combined and simultaneous effect a set of paired agents containing at least two activating agents and at least two therapeutic agents have on the activity of multiple signaling pathways. This approach is advantageous over methods that evaluate the effect of one or more paired sets of activating and therapeutic agents on the signaling activity of single pathways in cases where the signaling activity of two or more pathways is interconnected and unexpectedly strongly synergistic.

First, when multiple pathways in a patient's tumor cells are evaluated individually using the methods described herein with the goal of identifying the signaling pathway(s) driving the disease process, it is not possible to evaluate the affect one signaling pathway's activity has on another signaling pathway's activity. In patients with tumors driven by two or more interconnected signaling pathways, the aberrant signaling activity of each pathway may be effected by feedback, feedforward or crosstalk activity from the other pathway. For instance, signaling pathway activity associated primarily with one cell surface receptor (e.g. EGF receptor initiating EGF pathway) may be driven by activity associated with a different cell surface receptor (e.g. HGF receptor initiating EGF pathway activity). As a result, when a patient's tumor cells are contacted with a paired set of activating and therapeutic agents intended to effect only a single pathway (e.g. EGF ligand and an EGF inhibitor), the signaling activity measured will not reflect the potential feedback, lateral, feedforward or crosstalk effects another pathway may have on the pathway (e.g. EGF). In such cases, activation and inhibition of one or more signaling pathways individually with paired sets of activator and therapeutic agents may not lead to selection of the most therapeutically active agents. In these cases, it is thus advantageous to have an objective method to evaluate the combined functional activity of a set of two or more activating agents and two or more therapeutic agents on at least two or more different signaling pathways in a patient's viable tumor cells.

This approach allows for measurement of the effect of at least two different therapeutics targeting two different binding sites (e.g. EGFR, HGFR, HER3, PI3K) on the signaling activity of at least two different pathways. Instead of measuring the functional activity of multiple signaling pathways one at a time with paired sets of activating and therapeutic agents, this approach contacts the patient's viable tumor cells with two or more activating agents simultaneously and two or more therapeutic agents simultaneously and measures the resulting functional activity of the two or more signaling pathways. For example, if the EGF and HGF pathways (i.e., HER family signaling pathway and c-Met/HGF signaling pathway, respectively) are functionally interconnected but evaluated separately with EGF ligand and an EGFR inhibitor as a paired set and with HGF ligand and an HGFR inhibitor as a paired set, the output value for signaling attenuation derived for each paired set may be less than 50%. This would suggest that neither the EGF nor HGF inhibitors were therapeutically active in the patient's cancer cells and thus they would not be selected to treat the patient. However, if the functional activity of the EGF and HGF pathways were evaluated by contacting the patient's tumor cells with HGF and EGF ligand simultaneously and with HGFR and EGFR inhibitors simultaneously, the attenuation in output value for the combined set of paired agents may be much greater than 50%. This would suggest that the combination of an EGFR and HGFR inhibitor would be therapeutically active in the patient's cancer cells and thus they would be selected to treat the patient. Thus, by evaluating multiple pathways simultaneously, rather than multiple pathways separately, the use of the present invention uniquely enables identification of targeted therapeutic combinations more therapeutically active than combinations selected on the basis of multiple but separate targeted therapeutic functional evaluations.

Second, simultaneously evaluating the effect of multiple activating and therapeutic agents on the signaling pathways in a patient's cells makes it possible to determine whether the potency of each of the two or more therapeutic agents evaluated on their respective pathways is amplified relative to when the therapeutic agents are evaluated separately. Currently, the dosage prescribed for each of the two or more targeted therapeutics when used in combination is the same dosage prescribed when the targeted therapeutics are prescribed as single agents. When using the present invention, the evaluation of multiple activating and therapeutic agents simultaneously in a patient's cells can indicate that a combination of two or more targeted therapeutics would be more therapeutically active than any of the targeted therapeutics used individually, and the two or more targeted therapeutics evaluated in combination become more potent, and thus are functionally synergistic. In cases where two or more targeted therapeutics are functioning synergistically, the concentration of one or both targeted therapeutics contacting the patient's cells when evaluated using the methods described herein to produce a given output value are less than would be required if each targeted therapeutic contacted the patient's cells separately. For instance, using the methods described herein to evaluate the functional activity of two interconnected pathways individually, the concentration of each targeted therapeutic agent contacting the patient's cells required to maximize the output value for each pathway may be 500 nanomolar. However, if the functional activity of the same two interconnected pathways are evaluated simultaneously, the concentration of one or both targeted therapeutic agents simultaneously contacting the patient's cells required to maximize the output value for the combined pathways may only be 50 nanomolar, 90% less than the concentration required when the pathways were evaluated individually.

When the methods described herein indicate that a combination of two or more targeted therapeutics are functioning synergistically in a patient's cells, the dosage of each targeted therapeutic required to treat a patient efficaciously may thus be less than than the dosage required when a patient is treated with only one of the targeted therapeutics. Using the methods described herein to identify two or more targeted therapeutics that are functionally synergistic and to confirm that the desired therapeutic activity can be provided with lower doses of each therapeutic offers several further advantages. First, since nearly all targeted therapeutics are toxic and pose safety-related side effects to the patients receiving them, it is advantageous to prescribe the lowest dosage of drug possible that provides the patient with the desired clinical benefit. Second, since the safety and toxicity side effects of targeted therapeutics are often additive, many patients are not able to tolerate treatment with two targeted therapies when the recommended dosage levels for each targeted therapeutic are the same as when they are prescribed on a stand-alone basis. Determining a priori that two or more targeted therapeutics are functionally synergistically in a patient's tumor cells, so that a smaller dose of each targeted therapeutic can be selected to treat them, will reduce potential for side effects for patients who could not tolerate larger doses of two of more therapeutics to benefit from treatment with them.

Accordingly, in one embodiment, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample simultaneously with at least at least two sets of paired agents, each set comprised of a first agent that is at least one targeted therapeutic and a second agent that is at least one activator that is known to selectively affect the same signaling pathway the first agent is intended to address, wherein each set of paired agents affects a different signaling pathway, so as to upregulate or downregulate the signaling pathway as measured by an effect on cell adhesion or attachment, to produce a sample contacted with at least two sets of paired agents;

continuously measuring cell adhesion or attachment of the viable cancer cells in the sample contacted with each set of paired agents, relative to a sample of viable cancer cells obtained from the subject that is contacted with each of the first agents or each of the second agents alone;

determining by mathematical analysis of the continuous measurements an output value for each set of paired agents that characterizes whether a change in cell adhesion or attachment has occurred in the sample contacted with the set of paired agents, as compared to the sample contacted with the first agents or the second agents alone; and administering to the subject at least one targeted therapeutic that affects the same signaling pathway as the first agent from the set of paired agents determined to have the highest output value of all sets tested, indicating the administered targeted therapeutic agent is more therapeutically active in the cell signaling pathway of the subject's cancer cells than the targeted therapeutic(s) from the set(s) of paired agents with lower output value.

In another embodiment, the invention pertains to a method of identifying a targeted therapeutic that is therapeutically active in the signaling pathway it is intended to address in a subject's cancer cells, the method comprising:

culturing a sample comprising viable cancer cells obtained from the subject;

contacting the sample simultaneously with at least two sets of paired agents, each set comprised of at least one targeted therapeutic and at least one activator that is known to selectively affect the same signaling pathway the targeted therapeutic is intended to address, wherein each set of paired agents affects a different signaling pathway, so as to upregulate or downregulate the signaling pathway as measured by an effect on cell adhesion or attachment, to produce a sample contacted with at least two sets of paired agents;

continuously measuring cell adhesion or attachment of the viable cancer cells in the sample contacted with each set of paired agents, relative to a sample of viable cancer cells obtained from the subject that is contacted with each of the targeted therapeutics or each of the activators alone;

determining by mathematical analysis of the continuous measurements an output value for each set of paired agents that characterizes whether a change in cell adhesion or attachment has occurred in the sample contacted with the set of paired agents, as compared to the sample contacted with the targeted therapeutics or the activators alone; and identifying the targeted therapeutic from the set of paired agents determined to have the highest output value of all sets tested, indicating the targeted therapeutic agent is more therapeutically active in the cell signaling pathway of the subject's cancer cells than the targeted therapeutic(s) from the set(s) of paired agents with lower output value.

In one embodiment, the targeted therapeutic(s) that is administered to the subject is the first agent(s) from the set of paired agents determined to have the highest output value. In another embodiment, the targeted therapeutic(s) that is administered to the subject is different than the first agent(s) from the set of paired agents determined to have the highest output value but targets the same signaling pathway as said first agent(s).

The methods for evaluating multiple signaling pathways in the patient's cells can combine both simultaneous assessment of multiple different signaling pathways in the same cell sample and parallel assessment of multiple different signaling pathways using different portions of the cell sample. Parallel assessment of multiple different signaling pathways using different portions of the cell sample is described further in subsection B above. For example, for three different signaling pathways designated X, Y and Z, different portions of the patient's cell sample can be contacted with one or more targeted therapeutic/activator pairs (referred to as a "TT/A pair") as follows: (i) one TT/A pair that affects pathway X alone: (ii) one TT/A pair that affects pathway Y alone; (iii) one TT/A pair that affects pathway Z alone; (iv) one TT/A pair that affects pathway X and one TT/A pair that affects pathway Y; (v) one TT/A pair that affects pathway X and one TT/A pair that affects pathway Z; (vi) one TT/A pair that affects pathway Y and one TT/A pair that affects pathway Z; and (vii) one TT/A pair that affects pathway X, one TT/A pair that affects pathway Y and one TT/A pair that affects pathway Z. The sample with the highest output value then determines which targeted therapeutic(s) is most active in the patient's cancer cells. For example, if the sample contacted with one TT/A pair that affects pathway X and one TT/A pair that affects pathway Z exhibits the highest output value of all samples tested, then the patient would be administered two different targeted therapeutics, one that affects pathway X and one that affects pathway Z (these two targeted therapeutics could be the same agents that were tested in vitro or, alternatively, could be different agents that also affect pathways X and Z). Non-limiting specific examples of such analyses that combine simultaneous and parallel assessment of multiple pathways, the selection of the most appropriate targeted therapeutic(s) treatment regiment based thereon, are described further in Example 3.

In one embodiment, a TT/A pair comprises one targeted therapeutic and more than one activator, each of which activator is known to selectively affect the same signaling pathway the targeted therapeutic is intended to address. For example, in one embodiment, a TT/A pair comprises one targeted therapeutic and two different activators, each of which activator is known to selectively affect the same signaling pathway the targeted therapeutic is intended to address.

In one embodiment, different portions of a patient's cells sample are contacted with multiple TT/A pairs, wherein the concentration of one or more of the targeted therapeutics tested is varied between sample portions to thereby determine the concentration of targeted therapeutic(s) that is most effective in the patient's cells. For example, a portion of a patient's cell sample can be simultaneously contacted with a TT/A pair that affects signaling pathway X and a TT/A pair that affects signaling pathway Y at a first concentration and another portion of the patient's cell sample can be simultaneously contacted with a TT/A pair that affects signaling pathway X and a TT/A pair that affects signaling pathway Y at a second concentration. In one embodiment, the concentration of only one of the targeted therapeutics tested is varied (e.g., the concentration of the TT from the TT/A pair that affects signaling pathway X is varied). In another embodiment, the concentration of more than one of the targeted therapeutics tested is varied (e.g., the concentration of the TT from the TT/A pair that affects signaling pathway X is varied and the concentration of the TT from the TT/A pair that affects signaling pathway Y is also varied). Such analyses can thereby determine not only which targeted therapeutic(s) is most effective in the patient's cells but also which concentration is most effective. In one embodiment, the effective concentration identified for a combination of two or more targeted therapeutics is different than the effective concentration of one or more of the targeted therapeutics alone. For example, as discussed above and illustrated in Example 3, a targeted therapeutic with an effective concentration of 500 nanomolar alone was demonstrated to be effective at 50 nanomolar (i.e., a 10-fold lower concentration) when tested in combination with a second targeted therapeutic that targets a different signaling pathway.

In one embodiment, the signaling pathways are selected from the group consisting of HER2/HER1, HER1, HER2/HER3, HER3, c-Met/HGF, ALK, FGFR, IGFR, EGFR, FLT3, Axl, PDGFR, SMO, Patched 1, Frizzled and Notch.

In one embodiment, the sets of paired agents and signaling pathways are selected from the pairs of agent set forth in Table 2 or Table 12.

In one embodiment, the signaling pathways are selected from the group consisting of HER2/HER1, HER1, HER2/HER3, HER3, c-Met/HGF, ALK, ROS, FGFR, IGFR, EGFR, FLT3, Axl, Tyro 3, Mer, PDGFR, SMO, Patched 1, Frizzled, Notch, MAPK, RON, RHO, AKT, FAK1, RAS, RAF, PI3K/PTEN, MAK, MKK, MEK, MEKK, Mos, Erk, MLK, MLK3, TAK, DLK, p38, ASK, SAPK, JNK, BMK, PKC, PI3K, PIK3/PTEN, Bad, Bcl, Bak, Bax, BID, Bim, Noxa, Puma, BH3, caspase, p53, NIK, NFkB, ROCK, XIAP, MOMP, ILK, PDK, insulin receptor (IR), IGFR, mTOR, Jak, PIKK, 4E-BP1, Raptor, KMT, MLL, KDM, UTX, DOT1L, BRD, TET, SirT1, Hat, SNF, DNMT, EZH, AMPK, PLC, CaMKK, glucose transporter, PFK, FAS, Krebs Cycle, glycolysis, TNFR, TRAD, TRAF, TAB, NEMO, NIK, IKK, RelA, RelB, kB, IL1R, IRAK, Myd88, TRADD, FADD, FLIPs, ICAD, CAD, PARP, lamins, ZNRF, WntR, PAR, GSK, Dsh, LGR, catenin, WTX, APC, Src, CBP, Fringe, Furin, Delta Jagged, NIC, presenilin, CDO, BOC, Gli, KIF, cyclin D, cyclin E, SARA, Smad, Smurf, NLK, p28, Myc, Max, Fos, Jun, LIMK, cofilin, CD44, FAT, KIBRA, FRMD, Mst, YAP, LATS, MOB, SAV, TEAD, Mer, SAB, TAZ, Rho, Rac, PAK, CREB, HER2, HER3, HER4, estrogen receptors, progesterone receptors, androgen receptors, GPER30, VEGF receptor, TGFbeta/SMAD, WNT, Hedgehog/GLI, HIF1 alpha, JAK/STAT, control of G1/S transition, DNA damage control, and apoptosis.

In one embodiment, each set of paired agents selectively affects a different HER family signaling pathway.

In another embodiment, at least one set of paired agents that selectively affects a HER family signaling pathway is tested in combination with at least one set of paired agents that selectively affects a signaling pathway other than the HER family signaling pathway. For example, in one embodiment, at least one set of paired agents that selectively affects a HER family signaling pathway is tested in combination with at least one set of paired agents that selectively affects the c-Met/HGF signaling pathway. In another embodiment, at least one set of paired agents that selectively affects a HER family signaling pathway is tested in combination with at least one set of paired agents that selectively affects the estrogen receptor (ER) signaling pathway. In another embodiment, at least one set of paired agents that selectively affects a HER family signaling pathway is tested in combination with at least one set of paired agents that selectively affects the FGFR signaling pathway. In another embodiment, at least one set of paired agents that selectively affects a HER family signaling pathway is tested in combination with at least one set of paired agents that selectively affects the PDGFR signaling pathway.

In another embodiment, at least one set of paired agents that selectively affects the estrogen receptor (ER) signaling pathway is tested in combination with at least one set of paired agents that selectively affects a signaling pathway other than the ER family signaling pathway. For example, in one embodiment, at least one set of paired agents that selectively affects the ER signaling pathway is tested in combination with at least one set of paired agents that selectively affects the HER family signaling pathway. In another embodiment, at least one set of paired agents that selectively affects the ER signaling pathway is tested in combination with at least one set of paired agents that selectively affects the IGFR signaling pathway.

In another embodiment, at least one set of paired agents that comprises a pan HER signaling pathway inhibitor is tested in combination with at least one set of paired agents that comprises a c-Met/HGF inhibitor. In another embodiment, at least one set of paired agents that comprises an inhibitor(s) of HER1/HER3 signaling pathways is tested in combination with at least one set of paired agents that comprises a c-Met/HGF inhibitor. In another embodiment, at least one set of paired agents that comprises a pan HER signaling pathway inhibitor is tested in combination with at least one set of paired agents that comprises a PI3K inhibitor. In another embodiment, at least one set of paired agents that comprises an inhibitor(s) of HER1/HER3 signaling pathways is tested in combination with at least one set of paired agents that comprises a PI3K inhibitor.

In one embodiment, each set of paired agents is selected from the sets of paired agents set forth in Table 12.

Various suitable targeted therapeutics, activators and signaling pathways are also described further in the subsections below and in the Examples.

Sample preparation and culturing, continuous monitoring of cell adhesion or attachment and mathematical analysis are described in further detail in the subsections below.

In one embodiment, cell adhesion or attachment is measured using an impedance biosensor or an optical biosensor. Use of biosensors is described in further detail in the subsections below.

In one embodiment, the cancer is selected from the group consisting of breast cancer, lung cancer, colorectal cancer, bladder cancer, kidney cancer, ovarian cancer and leukemia. Additional suitable cancers are described in the subsections below.

In one embodiment, the sample of viable cancer cells is cultured in a media comprising growth factors and free of serum. In another embodiment, the sample of viable cancer cells is also cultured in a media comprising an anti-apoptotic agent and free of serum. Culture conditions and culturing of cells is described in further detail in the subsections below.

In one embodiment, the at least one targeted therapeutic that is administered to the subject is selected from the group consisting of cetuximab, erlotinib, gefitinib, lapatinib, pazopanib, trastuzumab, fulvestrant, tamoxifen, letrozole, anastrozole, exemestane, everolimus, abiraterone, bicalutamide, bortezomib, vemurafenib, ipilimumab, Pertuzumab, MEDI4276, ONT-380, Neratinib, Afatinib, Duligotuzumab, Dacomitinib, Sapitinib, Poziotinib, ASLAN001, MM-111 MM-121, MM-141, LJM716, U3-1287 (AMG 888), TK-A3/TK-A4, Lumretuzumab, REGN1400, AV-203, AZD5363, Afuresertib, MK-2206, Ipatasertib, Ridaforolimus, Temsirolimus, Selemetinib, Cobimetinib, GDC-0994, Taselisib, Alpelisib, Buparlisib, AZD8186, AZD8835, Panitumumab, REGN955, MM-151, Osimertinib, Rociletinib, AZD5363, SGX-523, Onartuzumab, Cabozantinib, Volitinib, Tivantinib, Capmatinib, Emibetuzumab, Rilotumumab, Ficlatuzumab, SAR125844, emibetuzumab, Sym015, AMG337, JNJ-61186372, glesatinib, 1202, LY3023414, Gedatolisib, JI-101, Ponatinib, Sunitinib, Crizotinib, Ceritinib, Brigatinib, Alectinib, BGJ398, Linsitinib, Quizartinib, R428 (BGB324), gilteritinib, Vismodegib, Itraconazole, 5E1, LGK974, Semagacestat, Cobimetinib, AZD4547, JNJ-42756493, Dalotuzumab, MEDI-573, Ganitumab, Sonidegib, Vantictumab, Ipafricept, Tarextumab, Brontictuzumab, SB431542, EW-7197, RepSox, AZD9291, Rociletinib, abraxane, brentuximab vedoton, ofatumumab, bevacizumab, alemtuzumab, bicalutamide, gemcitabine, imatinib, ixabepilone, romidepsin, cabrazitaxel, sorafenib, infliximab, lenalidomide, rituximab, dasatinib, nilotinib, temozolomide, bortezomib, azacitidine, tepotinib, lorlatinib, merestinib, RG6114, tucantinib, pazopanib, crizotinib, vemurafenib, goserelin acetate, abiraterone, a BH3 mimetic, navitoclax, anastrozole, letrozole, an aromatase inhibitor, ixabepilone, aflibercept, temsirolimus, irbritumomab, abiraterone, custirsen, enzalutamide, nivolumab, palbociclib, regorafenib, entinostat, ARN-509, ARN-810, BIND-014, dabrafenib, daratumumab, lambrolizumab, LDK378, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof.

In one embodiment, the activator in each paired set of agents is a protein, peptide, nucleic acid, metabolite, ligand, reagent, organic molecule, signaling factor, growth factor, biochemical, or combinations thereof.

Various suitable targeted therapeutics, activators, signaling pathways and targeted therapeutic/activator pairs are described further in subsection B above, in the subsections below and in the Examples.

G. Methods of Evaluating a Pathway with a Combination of Specific and Non-Specific Therapeutic Agents In another aspect of the invention, the method used to select one or more therapeutic agents for treatment of a cancer patient involves evaluating the functional activity of one signaling pathway in the patient's cancer cells using a set of agents containing one activating agent and two or more therapeutic agents, where the activating agent and one of the therapeutic agents bind to the same signaling pathway and the other therapeutic agent(s) binds to a different signaling pathway or cellular location.

Since a signaling pathway is interconnected to other signaling pathways and cellular activities with multiple points of convergence, cross-talk, and feedback loops, a targeted therapeutic designed to inhibit pathway activity initiated at the activator binding site (e.g. cell surface receptor) may not be sufficient to inhibit a majority of the signaling activity associated with that pathway. In cases where the majority of signaling pathway activity initiated by an activator agent cannot be inhibited by a matching signaling pathway inhibitor directly targeting the same approximate binding site as the activator, a therapy targeting a different binding site than the binding site of the activator may be able to enhance the effectiveness of the targeted therapy so that a majority of the initiated signaling pathway activity in a patient's cells could be inhibited. The addition of the therapeutic agent that binds to a different binding site than the activating and therapeutic agents' binding site can thus synergistically increase the targeted therapeutics' ability to inhibit the activated signaling activity. This approach allows for measurement of the effect a therapeutic targeting a binding site downstream (e.g. AKT, PI3K, MEK, ERK, mTOR, DNA bases, nucleic acids, microtubules, purines), upstream (e.g. ER, RAS, RAF), or lateral (e.g. Hedgehog, Notch, Wnt, c-MET, ALK, AXL, FGFR) to the binding site of the activator agent has on signaling pathway activity initiated by the activator agent and inhibited with a targeted therapeutic that binds to the same approximate binding site as the activator agent. For example, using the methods described herein, only 40% of MET signaling pathway activity initiated by HGF (a MET ligand) may be inhibited when a patient's tumor cells are contacted with tepotinib, a MET targeted therapeutic. However, when the patient's cells are also contacted with a therapeutic agent such as a palbociclib, a CDK4/6 inhibitor, 80% of MET signaling activity initiated by HGF may be inhibited. By evaluating whether a therapeutic agent that binds to a site downstream, upstream, or lateral to the activation and inhibition binding site of a paired set of activator and therapeutic agents in a patient's cells, this approach improves on methods that evaluate the effect of a pair of signaling pathway activator and targeted therapeutic agents have alone in the patient's cells.

Accordingly, in one embodiment, the invention pertains to a method of treating a human subject diagnosed with cancer, the method comprising:

administering to the subject at least one targeted therapeutic that is therapeutically active in a signaling pathway in which signaling has been measured in the subject's cancer cells by a method comprising:

culturing a sample comprising viable cancer cells obtained from the subject;

contacting the sample simultaneously with at least one triplet set of agents, each triplet set comprised of a first agent targeted therapeutic, a second agent activator that is known to selectively affect the same signaling pathway the first agent is intended to address and a third agent targeted therapeutic that affects a different signaling pathway than the first agent or a different location within the signaling pathway that the first agent affects, so as to upregulate or downregulate the signaling pathway that the first agent affects as measured by an effect on cell adhesion or attachment, to produce a sample contacted with at least one triplet set of agents;

continuously measuring cell adhesion or attachment of the viable cancer cells in the sample contacted with the at least one triplet set of agents, relative to a sample of viable cancer cells obtained from the subject that is contacted with the first agent targeted therapeutic alone, the second agent activator alone or the third agent targeted therapeutic alone;

determining by mathematical analysis of the continuous measurements an output value for the at least one triplet set of agents that characterizes whether a change in cell adhesion or attachment has occurred in the sample contacted with the triplet set of agents, as compared to the sample contacted with the first agent targeted therapeutic alone, the second agent activator alone or the third agent targeted therapeutic alone; and administering to the subject at least one targeted therapeutic that affects the same signaling pathway as the first agent targeted therapeutic from the triplet set of agents when the output value is greater than a pre-determined cut-off value indicating the first agent targeted therapeutic agent is therapeutically active in the cell signaling pathway of the subject's cancer cells.

In one embodiment, the targeted therapeutic that is administered to the subject is the first agent targeted therapeutic. In another embodiment, the targeted therapeutic that is administered to the subject is different than the first agent targeted therapeutic but targets the same signaling pathway as said first agent targeted therapeutic. In another embodiment, the targeted therapeutic that is administered to the subject is the third agent targeted therapeutic. In another embodiment, the targeted therapeutic that is administered to the subject is different than the third agent targeted therapeutic but targets the same signaling pathway as said third agent targeted therapeutic. In another embodiment, the targeted therapeutics that are administered to the subject are both the first agent targeted therapeutic and the third agent targeted therapeutic. In another embodiment, two targeted therapeutics are administered to the subject that are different than the first and third agent targeted therapeutics but the two administered targeted therapeutics target the same signaling pathways as said first and third agent targeted therapeutics.

In another aspect, the invention pertains to a method of identifying a targeted therapeutic that is therapeutically active in the signaling pathway it is intended to address in a subject's cancer cells, the method comprising:

culturing a sample comprising viable cancer cells obtained from the subject;

contacting the sample simultaneously with at least one triplet set of agents, each triplet set comprised of a first agent targeted therapeutic, a second agent activator that is known to selectively affect the same signaling pathway the first agent is intended to address and a third agent targeted therapeutic that affects a different signaling pathway than the first agent or a different location within the signaling pathway that the first agent affects, so as to upregulate or downregulate the signaling pathway that the first agent affects as measured by an effect on cell adhesion or attachment, to produce a sample contacted with at least one triplet set of agents;

continuously measuring cell adhesion or attachment of the viable cancer cells in the sample contacted with the at least one triplet set of agents, relative to a sample of viable cancer cells obtained from the subject that is contacted with the first agent targeted therapeutic alone, the second agent activator alone or the third agent targeted therapeutic alone;

determining by mathematical analysis of the continuous measurements an output value for the at least one triplet set of agents that characterizes whether a change in cell adhesion or attachment has occurred in the sample contacted with the triplet set of agents, as compared to the sample contacted with the first targeted therapeutic alone, the second agent activator alone or the third agent targeted therapeutic alone; and identifying the first agent targeted therapeutic from the triplet set of agents when the output value is greater than a pre-determined cut-off value indicating the first agent targeted therapeutic agent is therapeutically active in the cell signaling pathway of the subject's cancer cells.

In one embodiment, the targeted therapeutic (e.g., first agent targeted therapeutic) is determined to have an output value percentage greater than 50% indicating the signaling pathway affected by the targeted therapeutic is active in the subject's cancer cells. In another embodiment, the targeted therapeutic (e.g., first agent targeted therapeutic) is determined to have an output value percentage greater than 50% indicating the targeted therapeutic is therapeutically active in the cell signaling pathway of the subject's cancer cells.

In one embodiment, the first agent targeted therapeutic, second agent activator and signaling pathway affected by the first and second agents are selected from the pairs of agent set forth in Table 2. In another embodiment, each set of paired agents is selected from the sets of paired agents set forth in Table 12.

The third agent targeted therapeutic affects a different signaling pathway than the first agent or a different location within the signaling pathway that the first agent affects. Thus, in one embodiment, the first agent targeted therapeutic and the third agent targeted therapeutic affect different signaling pathways. In another embodiment, the third agent targeted therapeutic affects the same signaling pathway as the first targeted therapeutic, but at a different location within the signaling pathway that the first agent affects (e.g., the binding site of the third agent targeted therapeutic can be upstream, downstream or lateral to the binding site of the first agent targeted therapeutic).

In one embodiment, the signaling pathways are selected from the group consisting of HER2/HER1, HER1, HER2/HER3, HER3, c-Met/HGF, ALK, FGFR, IGFR, EGFR, FLT3, Axl, PDGFR, SMO, Patched 1, Frizzled and Notch.

In one embodiment, the signaling pathways are selected from the group consisting of HER2/HER1, HER1, HER2/HER3, HER3, c-Met/HGF, ALK, ROS, FGFR, IGFR, EGFR, FLT3, Axl, Tyro 3, Mer, PDGFR, SMO, Patched 1, Frizzled, Notch, MAPK, RON, RHO, AKT, FAK1, RAS, RAF, PI3K/PTEN, MAK, MKK, MEK, MEKK, Mos, Erk, MLK, MLK3, TAK, DLK, p38, ASK, SAPK, JNK, BMK, PKC, PI3K, PIK3/PTEN, Bad, Bcl, Bak, Bax, BID, Bim, Noxa, Puma, BH3, caspase, p53, NIK, NFkB, ROCK, XIAP, MOMP, ILK, PDK, insulin receptor (IR), IGFR, mTOR, Jak, PIKK, 4E-BP1, Raptor, KMT, MLL, KDM, UTX, DOT1L, BRD, TET, SirT1, Hat, SNF, DNMT, EZH, AMPK, PLC, CaMKK, glucose transporter, PFK, FAS, Krebs Cycle, glycolysis, TNFR, TRAD, TRAF, TAB, NEMO, NIK, IKK, RelA, RelB, kB, IL1R, IRAK, Myd88, TRADD, FADD, FLIPs, ICAD, CAD, PARP, lamins, ZNRF, WntR, PAR, GSK, Dsh, LGR, catenin, WTX, APC, Src, CBP, Fringe, Furin, Delta Jagged, NIC, presenilin, CDO, BOC, Gli, KIF, cyclin D, cyclin E, SARA, Smad, Smurf, NLK, p28, Myc, Max, Fos, Jun, LIMK, cofilin, CD44, FAT, KIBRA, FRMD, Mst, YAP, LATS, MOB, SAV, TEAD, Mer, SAB, TAZ, Rho, Rac, PAK, CREB, HER2, HER3, HER4, estrogen receptors, progesterone receptors, androgen receptors, GPER30, VEGF receptor, TGFbeta/SMAD, WNT, Hedgehog/GLI, HIF1 alpha, JAK/STAT, control of G1/S transition, DNA damage control, and apoptosis.

In one embodiment, the first agent targeted therapeutic affects the MET signaling pathway (e.g., tepotinib), the second agent activator activates the MET signaling pathway (e.g., a MET ligand, such as HGF) and the third agent targeted therapeutic is an EGFR inhibitor (e.g., erlotinib). In another embodiment, the first agent targeted therapeutic affects the MET signaling pathway (e.g., tepotinib), the second agent activator activates the MET signaling pathway (e.g., a MET ligand, such as HGF) and the third agent targeted therapeutic is an CDK4/6 inhibitor (e.g., palbociclib).

Sample preparation and culturing, continuous monitoring of cell adhesion or attachment and mathematical analysis are described in further detail in the subsections below.

In one embodiment, cell adhesion or attachment is measured using an impedance biosensor or an optical biosensor. Use of biosensors is described in further detail in the subsections below.

In one embodiment, the cancer is selected from the group consisting of breast cancer, lung cancer, colorectal cancer, bladder cancer, kidney cancer, ovarian cancer and leukemia. Additional suitable cancers are described in the subsections below.

In one embodiment, the sample of viable cancer cells is cultured in a media comprising growth factors and free of serum. In another embodiment, the sample of viable cancer cells is also cultured in a media comprising an anti-apoptotic agent and free of serum. Culture conditions and culturing of cells is described in further detail in the subsections below.

In one embodiment, the at least one targeted therapeutic that is administered to the subject is selected from the group consisting of cetuximab, erlotinib, gefitinib, lapatinib, pazopanib, trastuzumab, fulvestrant, tamoxifen, letrozole, anastrozole, exemestane, everolimus, abiraterone, bicalutamide, bortezomib, vemurafenib, ipilimumab, Pertuzumab, MEDI4276, ONT-380, Neratinib, Afatinib, Duligotuzumab, Dacomitinib, Sapitinib, Poziotinib, ASLAN001, MM-111 MM-121, MM-141, LJM716, U3-1287 (AMG 888), TK-A3/TK-A4, Lumretuzumab, REGN1400, AV-203, AZD5363, Afuresertib, MK-2206, Ipatasertib, Ridaforolimus, Temsirolimus, Selemetinib, Cobimetinib, GDC-0994, Taselisib, Alpelisib, Buparlisib, AZD8186, AZD8835, Panitumumab, REGN955, MM-151, Osimertinib, Rociletinib, AZD5363, SGX-523, Onartuzumab, Cabozantinib, Volitinib, Tivantinib, Capmatinib, Emibetuzumab, Rilotumumab, Ficlatuzumab, SAR125844, emibetuzumab, Sym015, AMG337, JNJ-61186372, glesatinib, 1202, LY3023414, Gedatolisib, JI-101, Ponatinib, Sunitinib, Crizotinib, Ceritinib, Brigatinib, Alectinib, BGJ398, Linsitinib, Quizartinib, R428 (BGB324), gilteritinib, Vismodegib, Itraconazole, 5E1, LGK974, Semagacestat, Cobimetinib, AZD4547, JNJ-42756493, Dalotuzumab, MEDI-573, Ganitumab, Sonidegib, Vantictumab, Ipafricept, Tarextumab, Brontictuzumab, SB431542, EW-7197, RepSox, AZD9291, Rociletinib, abraxane, brentuximab vedoton, ofatumumab, bevacizumab, alemtuzumab, bicalutamide, gemcitabine, imatinib, ixabepilone, romidepsin, cabrazitaxel, sorafenib, infliximab, lenalidomide, rituximab, dasatinib, nilotinib, temozolomide, bortezomib, azacitidine, tepotinib, lorlatinib, merestinib, RG6114, tucantinib, pazopanib, crizotinib, vemurafenib, goserelin acetate, abiraterone, a BH3 mimetic, navitoclax, anastrozole, letrozole, an aromatase inhibitor, ixabepilone, aflibercept, temsirolimus, irbritumomab, abiraterone, custirsen, enzalutamide, nivolumab, palbociclib, regorafenib, entinostat, ARN-509, ARN-810, BIND-014, dabrafenib, daratumumab, lambrolizumab, LDK378, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof.

In one embodiment, the activator in each paired set of agents is a protein, peptide, nucleic acid, metabolite, ligand, reagent, organic molecule, signaling factor, growth factor, biochemical, or combinations thereof.

Various suitable targeted therapeutics, activators, signaling pathways and targeted therapeutic/activator pairs are described further in subsection B above, in the subsections below and in the Examples.

H. Signaling Pathways, Activators and Targeted Therapeutics

Often when a patient is diagnosed with a particular disease or condition, there is a range of treatment options. In some cases, treatments may be very expensive or the side effects associated with the treatment may be severe so it would be useful to know whether the patient is likely to be a responder or a non-responder to a treatment. In addition, if a patient becomes resistant, it would be useful to know which other treatments might be efficacious now that the patient's diseased cells have become resistant.

In certain embodiments, any therapeutic agent or agents that are used in the treatment of a condition for which some patients respond and others do not respond can be analyzed in the methods described herein. For example, for cancer, a number of targeted immunotherapies are available including a number of different chimeric and humanized antibodies. For autoimmune conditions, molecules such as those targeted to inflammatory cytokines or their receptors may be analyzed. Examples of agents targeted to inflammatory cytokines are anti-TNF a agents, agents targeting interferon alpha, interleukins, and the like. Immunosuppressive agents such as corticosteroids, tacrolimus (FK-506 or TACR) (inhibits T-cell metabolism and proliferation), sirolimus (SIRO/81768), myocophenolic acids, mycophenolate mofetil (MMF), calcineurin inhibitors (CI), cyclosporin (CsA), and rapamycin (mTOR inhibitor).

In other embodiments, the methods involve testing of one or more therapeutic agents, perturbing agents (e.g., activator agents), confirming agents, or combinations thereof, for the ability to cause a change in a physiological parameter of the diseased cells from the individual subject. In embodiments, the therapeutic agents are also label free. In some embodiments, two or more therapeutic agents may be tested separately or in combination on separate samples of the diseased cells from the same patient. A therapeutic agent is selected that causes the greatest change in the cellular response or physiological characteristic at a lower dose than other therapeutic agents. Combinations of compounds may be determined that offer the greatest therapeutic effect. In embodiments, the determination may be as compared to healthy cells of the patient or healthy cells of a non-diseased patient or pool of non-diseased patient results to determine therapeutic index and other individual safety and tolerance effects.

Examples of pathways targeted by the signaling pathway activator and the therapeutic agent include HER2, HER3, HER4, c-MET, HGF, ALK, FGFR, IGFR, EGFR, PDGFR, FLT3, Axl, SMO, Fz, γ-secretase, MAPK-PK, RAS/RAF, RHO kinase, FAK1, MEK/MAPK, MAK, MKK, AKT, PIK3/PTEN, and VEGFR, cell adhesion, TGFbeta/SMAD, WNT, Hedgehog/GLI, HIF1 alpha, JAK/STAT, Notch, control of G1/S transition, DNA damage control, and apoptosis. In some embodiments, the agents target cellular pathways involved in cell cycle regulation. Exemplary agents that affect cell cycle regulation include those targeted to Cyclin Dependent Kinases, CDK4, CDK6, and cyclins (e.g., cyclins A, B, C, D, E, or F, and G1/S cyclins), and BCR-ABL. In some embodiments, the agents target aromatase enzyme.

In exemplary embodiments, the signaling pathway activator and the targeted therapeutic agent act on a cellular pathway involved in at least one of the following cellular processes: MAP kinase signaling, apoptosis, PI3K/Akt/mTOR signaling, chromatin/epigenetic regulation, cellular metabolism, cell cycle control, immunology and inflammation, development and differentiation, and/or cytoskeletal regulation and adhesion.

Exemplary signaling pathway activators, and the pathways they target, are provided in Tables 3-12 below.

TABLE 3

| Cell Process-MAP Kinase Signaling |
|---|
| Pathways |
| Mitogen-Activated Protein Kinase Cascades
MAPK/Erk in Growth and Differentiation
G-Protein-Coupled Receptors Signaling to MAPK/Erk |

TABLE 3-continued

Cell Process-MAP Kinase Signaling

SAPK/JNK Signaling Cascades
Signaling Pathways Activating p38 MAPK

| Ligands/Signaling pathway activators | Pathway & examples of members | References |
|---|---|---|
| Mitogens | Ras, Raf, Mos, MEK, Erk, MAPK | *Cell. Mol. Life Sci.* 64(21), 2771-89 (2007) Regulatory mechanisms of mitogen-activated kinase signaling. |
| Growth Factors-EGF, FGF, PDGF | MLK3, TAK, DLK, MKK, P38, MAPK, MEK, Erk, EGFR, FGFR, PDGFR | *FASEB J.* 22(4), 954-65 (2008) Phosphatase-mediated crosstalk between MAPK signaling pathways in the regulation of cell survival |
| Pro- & Anti-Inflammatory cytokines-IL-1, IL-6, IL-10, TNF-alpha | MEKK, MLK, ASK, MKK, SAPK, JNK, MAPK | Expert Opin Ther Targets. 2008 February; 12(2): 171-83. doi: 10.1517/14728222.12.2.171-Pro-inflammatory cytokine-induced SAPK/MAPK and JAK/STAT in rheumatoid arthritis and the new anti-depression drugs |
| Stress-temperature, heat shock, osmotic pressure, pressure, partial pressure of oxygen or CO2 | MEKK, MEK, Erk, BMK, SAPK, p38, MAPK | Biochem & Biophys Res Comm Volume 239, Issue 3, 29 Oct. 1997, Pages 840-844 Hypoxia and Hypoxia/Reoxygenation Activate p65PAK, p38Mitogen-Activated Protein Kinase (MAPK), and Stress-Activated Protein Kinase (SAPK) |
| GPCR ligands-dopamine, 5-HT, histamine, acetylcholine, amino acids and ions (glutamate, calcium, GABA), nucleotides, prostaglandins, leukotrienes, chemokines, thrombin, angiotensin | Erk, JNK, p38, MAPK | *Oncogene* 26(22), 3122-42 (2007) G protein regulation of MAPK networks |

TABLE 4

Cell Process-Apoptosis Pathways

Apoptosis (Overview)
Inhibition of Apoptosis
Death Receptor Signaling
Mitochondrial Control of Apoptosis

| Ligands/Signaling pathway activators | Pathway & examples of members | References |
|---|---|---|
| Trophic factors-Ex. NGF, neutrophins, BDNF | PKC & PI3K/AKT & Bad, Bcl, Bak, Bax, BID or Bim, Noxa, Puma, Caspase | Nature Reviews Molecular Cell Biology 9, 378-390 (May 2008) 1 doi: 10.1038/nrm2393-Expansion and evolution of cell death programmes |
| TNF, TRAIL | ASK, JNK, P53 & NIK, NF-kB, Caspase, ROCK | Biochim Biophys Acta. 2011 June; 1807(6): 735-45. doi: 10.1016/j.bbabio.2011.03.010. Recent advances in apoptosis, mitochondria and drug resistance in cancer cells |
| FasL | Caspase, BH3, Bid, XIAP, Bcl-2-regulated apoptotic pathway, Bax/Bak, MOMP | Cell Death Differ. 2012 January; 19(1): 42-50. doi: 10.1038/cdd.2011.121. Fas death receptor signaling: roles of Bid and XIAP |

TABLE 5

Cell Process-PI3 Kinase/Akt/mTOR Signaling

Pathways

PI3K/Akt Signaling
PI3K/Akt Binding Partners Table
PI3K/Akt Substrates Table
ALK signaling pathway

| Ligands/Signaling pathway activators | Pathway & examples of members | References |
|---|---|---|
| Integrins bind ECM/RGD peptides | PI3K, FAK, ILK, PDK, Akt | Integrin signalling during tumour progression Nature |

TABLE 5-continued

Cell Process-PI3 Kinase/Akt/mTOR Signaling

| | | |
|---|---|---|
| Insulin | IR, IGFR, PI3K, Akt, mTOR, Bel | Reviews Molecular Cell Biology 5, 816-826 (October 2004) doi: 10.1038/nrm1490 Diabetes February 2003 vol. 52 no. 2 227-231 doi: 10.2337/diabetes.52.2.227 Insulin Activation of Phosphatidylinositol 3-Kinase |
| NRG, HRG, IGF. PDGF | PI3K, PDK, Akt, mTOR, HER Family, PDGFR | Curr Cancer Drug Targets 8(3), 187-98 (2008) The PTEN/PI3K/AKT signalling pathway in cancer, therapeutic implications. |
| FAM150A, FAM150B | ALK | eLife 2015; 4: e09811, DOI: 10.7554/eLife.098H; FAM150A and FAM150B are activating ligands for anaplastic lymphoma kinase |
| Cytokines-GM-CSF, IL-3 | Jak, Ras, PI3K, PDK, Akt | The EMBO Journal (2006) 25, 479-489 doi: 10.1038/sj.emboj.7600948, & Protein Kinase Activity of Phosphoinositide 3-Kinase Regulates Cytokine-Dependent Cell Survival PLOS Biology Published: Mar. 19, 2013 DOI: 10.1371/journal.pbio. 1001515 |
| Rapamycin | PIKK, PI3K, Akt, 4E-BP1, Raptor, PDK | The tor pathway: a target for cancer therapy. Nature Reviews Cancer 4, 335-348 (1 May 2004) 1 doi: 10.1038/nrc1362 |
| Breakpoint cluster region protein (BCR)-ABL protein | PI3K, PDK, Akt, mTOR, PKC | Leukemia. 2004 February; 18(2): 189-218 JAK/STAT, Raf/MEK/ERK, PI3K/Akt and BCR-ABL in cell cycle progression and leukemogenesis |

The two TORCs and Akt. *Dev. Cell* 12(4), 487-502 (2007)

TABLE 6

Cell Process-Chromatin/Epigenetic Regulation

| Ligands/Signaling pathway activators | Pathway & examples of members | References |
|---|---|---|
| See steroid/hormone ligands of nuclear receptors, see ligands of Wnt pathway, see MAPK pathway ligands, see PI3K pathway ligands | KMT, MLL, KDM, UTX, DOT1L, BRD, TET, SirT1, Hat, SNF, DNMT, EZH | *Epigenetics & Chromatin* 2013, 6: 28 doi: 10.1186/1756-8935-6-28 Epigenetic coordination of signaling pathways during the epithelial-mesenchymal transition & Cancer Res. 2011 Mar. 1; 71(5): 1752-1762. doi: 10.1158/0008-5472.CAN-10-3573 Epigenetic Silencing Mediated Through Activated PI3K/AKT Signaling in Breast Cancer |

TABLE 7

Cell Process-Cellular Metabolism

Pathways

Insulin Receptor Signaling
AMPK Signaling
Warburg Effect

TABLE 7-continued

Cell Process-Cellular Metabolism

| Ligands/Signaling pathway activators | Pathway & examples of members | References |
|---|---|---|
| Stress, low glucose, heat shock, thrombin, | AMPK, PLC, CaMKK | (2011) AMP-activated protein kinase: nature's energy sensor. *Nat. Chem. Biol.* |

TABLE 7-continued

Cell Process-Cellular Metabolism

| | | |
|---|---|---|
| histamine, adrenergic receptor ligands | | 7(8), 512-8. |
| Insulin | AMPK, PI3K, Akt, Ras, Raf, Erk, | (2010) AMP-activated protein kinase and its downstream transcriptional pathways. *Cell. Mol. Life Sci.* 67(20), 3407-23 |
| Glucose, lactate, citrate | Glucose transporter & metabolism, Ras, PFK, FAS, Krebs Cycle,, AKT. Bim/Bad/Bcl | (2010) The Warburg effect and mitochondrial stability in cancer cells. *Mol. Aspects Med.* 31(1), 60-74 & (2011) Aerobic glycolysis: meeting the metabolic requirements of cell proliferation. *Annu. Rev. Cell Dev. Biol.* 27, 441-64 |
| Insulin & growth factors | PI3K, Akt, mTOR, glycolysis | (2011) Regulation of cancer cell metabolism. *Nat. Rev. Cancer* 11(2), 85-95 |

TABLE 8

Cell Process-Cell Cycle/DNA Damage

Pathways

Cell Cycle Control: G1/S Checkpoint
Cell Cycle Control: G2/M DNA Damage Checkpoint

TABLE 9

Cell Process-Immunology and Inflammation

Pathways

Jak/Stat Signaling: IL-6 Receptor Family
NF-κB Signaling
TLR Pathway
B Cell Receptor Signaling
T Cell Receptor Signaling

| Ligands/Signaling pathway activators | Pathway & examples of members | References |
|---|---|---|
| TNF | TNFR, NFkB, TRAD, TRAF, TAK, TAB, NEMO, NIK, IKK, MEKK, RelA, RelB, kB, | (2011) Regulation of TNF-induced NF-κB activation by different cytoplasmic ubiquitination events. *Cytokine Growth Factor Rev.* 22(5-6), 277-86 |
| IL-1 | IL1R, IRAK, MydBB, TRAF, TAB, TAK, NEMO, NFkB, RelA, RelB | (2008) Shared principles in NF-kappaB signaling. *Cell* 132(3), 344-62 |
| Fas/DR ligands | ASK, TRADD, FADD, MKK, JNK, Caspases, FLIPs, Bid, ICAD, CAD, PARP, Lamins | (2011) Non-canonical NF-κB signaling activation and regulation: principles and perspectives. *Immunol. Rev.* 244(1), 44-54 |
| Mitogens, Growth Factors and Hormones | | See individual references |
| Bone morphogenic protein 2 | NFkB | Mohan et al, 1998 |
| Bone morphogenic protein 4 | NFkB | Mohan et al, 1998 |
| Connective tissue growth factor CCN2 | NFkB | Gao et al, 2005 |
| Corticotropin-releasing Hormone | NFkB | Zbytek et al, 2004 |

TABLE 9-continued

Cell Process-Immunology and Inflammation

| | | |
|---|---|---|
| Endothelin-1 | NFkB | Gerstung et al, 2007 |
| Epidermal Growth Factor | NFkB | Biswas et al, 2000; Sethi et al, 2007 |
| Estrogen/beta-estradiol | NFkB | Hirano et al, 2006 |
| Folicle Stimulating Hormone | NFkB | Delfino & Walker, 1998 |
| Gastrin | NFkB | Ogasa et al, 2003 |
| GMCSF | NFkB | Ebner et al, 2003 |
| Hepatocyte Growth Factor | NFkB | Yao et al, 2004; Kaibori et al, 2004; Shen et al, 1997 |
| Insulin | NFkB | Bertrand et al, 1995; Madonna et al, 2007 |
| Insulin-like growth factor 1 | NFkB | Liu et al, 2001 |
| Lysophosphatidic acid | NFkB | Raj et al, 2004; Hwang et al, 2006; Chen et al, 2008 |
| M-CSF | NFkB | Brach et al, 1991 |
| Mullerian Inhibiting Substance | NFkB | Hoshiya et al, 2003 |
| Nerve Growth Factor | NFkB | Wood, 1995; Carter et al, 1996 |
| Neurokinin A | NFkB | Sun et al, 2008 |
| Pigment epithelium-derived factor (PEDF) | NFkB | Yabe et al, 2001 |
| Platelet Activating Factor (PAF) | NFkB | Fernandes et al, 2003; Seo et al, 2006 |
| Platelet-Derived Growth Factor | NFkB | Olashaw et al, 1992 |
| Plant steroids (diosgenin, hecogenin, tigogenin) | NFkB | Corbiere et al, 2003 |
| Progastrin | NFkB | Rengifo-Cam et al, 2007; Umar et al, 2008 |
| Prostratin | NFkB | Williams et al, 2004 |
| Relaxin | NFkB | Ho et al, 2007 |
| Resistan | NFkB | Silswal et al, 2005 |
| All-trans retinoic acid | NFkB | Farina et al, 2002; Mathieu et al, 2005 |
| RET/PTC3 Fusion oncoprotein | NFkB | Russell et al, 2003 |
| S100B | NFkB | Adami et al, 2004 |
| Serum | NFkB | Baldwin et al, 1991 |
| Sulphatide (L-selectin crosslinker) | NFkB | Turutin et al, 2003 |
| TGF-alpha | NFkB | Lee et al, 1995 |
| TGF-beta2 | NFkB | Lu et al, 2004 |
| Thromboxane | NFkB | Wei et al, 2007 |

TABLE 10

Cell Process-Development, and Differentiation

Pathways

Hippo Signaling
TGF-β Signaling
Hedgehog Signaling
Notch Signaling
Wnt/β-Catenin Signaling
Angiogenesis
Nuclear Receptor Signaling
ErbB/HER Signaling
Ras Signaling

| Ligands/Signaling pathway activators | Pathway & examples of members | References |
|---|---|---|
| FGF, IGF, VEGF, SLIT, PDGF | PI3K/Akt, FGFR, IGFR, PDGFR, | Angiogenesis-pathway map |

TABLE 10-continued

Cell Process-Development, and Differentiation

| | | |
|---|---|---|
| estradiol, androgen, testosterone | hormone/steroid and non-steroid activated signaling | Nuclear Receptor Signaling-pathway map |
| epidermal growth factors, neuregulins, or heregulins. | PI3K & MAPK | ErbB/HER Signaling-pathway map |
| R-spondin, Wnt | ZNRF, Frizzled, WntR, PAR, GSK, Dsh, LGR, catenin, WTX, APC | (2009) Wnt/beta-catenin signaling: components, mechanisms, and diseases. *Dev. Cell* 17(1), 9-26. & (2009) PARsing the phrase "all in for Axin"-Wnt pathway targets in cancer. *Cancer Cell* 16(5), 366-8 & |
| E-cadherin binds ECM peptide sequences, catenins | Src, catenin, CBP, GSK | Journal of Mammary Gland Biology and Neoplasia October 2003, Volume 8, Issue 4, pp 435-447 Wnt-Cadherin Connections in Normal and Neoplastic Mammary Epithelium |
| TACE, ADAM, Epsin, Neur, Mib, juxtacrin factors, DLL, JAG, γ-secretase | NOTCH, Fringe, Furin, Delta Jagged, NIC, presenilin | (2011) Notch signaling in solid tumours: a little bit of everything but not all the time. *Nat. Rev. Cancer* 11(5), 338-51 & (2011) Notch signaling: simplicity in design, versatility in function. *Development* 138(17), 3593-612. & (2011) Notch signalling in T-cell lymphoblastic leukaemia/lymphoma and other haematological malignancies. *J. Pathol.* 223(2), 262-73 |
| Hh, Shh, Dhh, SAG1.3 | CDO, BOC, Patched1, Smo, Gli, KIF, myc, cyclins D, E | (2010) Interactions between Hedgehog proteins and their binding partners come into view. *Genes Dev.* 24(18), 2001-12 & (2009) Paracrine Hedgehog signaling in cancer. *Cancer Res.* 69(15), 6007-10 & (2011) The Hedgehog's tale: developing strategies for targeting cancer. *Nat. Rev. Cancer* 11(7), 493-501. |
| TGF | SARA, Smad, Smurf, Ras, ERK, TAK, TAB, NLK, MKK, p28, JNK, Myc, Max, Fos, Jun | (2010) TGFbeta signalling: a complex web in cancer progression. *Nat. Rev. Cancer* 10(6), 415-24. |
| BMP, Mis | Smad, Smurf, LIMK, MKK, Erk, p38, Cofilin | (2007) Cross-talk between the bone morphogenetic protein pathway and other major signaling pathways results in tightly regulated cell-specific outcomes. *FEBS J.* 274(12), 2977-85 |
| GPCR ligands | CD44, FAT, KIBRA, FRMD, Mst, YAP, LATS, MOB, SAV, TEAD, Smad | (2010) The hippo signaling pathway in development and cancer. *Dev. Cell* 19(4), 491-505. |
| Dachsous (Ds), Ex | Mer, KIBRA, Mst, SAB, LATS, MOB, YAP, TAZ, Smad, TEAD | (2011) Snapshot: The hippo signaling pathway. Cell 145(3), 484-484.e1 |
| GTP and See also MAPK, PI3K ligands | Rho, Rac, Raf, PAK, MEK, Erk, Myc/Max, JNK, HIF, CREB, PI3K | "The Ras superfamily at a glance". *J. Cell. Sci.* 118 (Pt 5): 843-6. doi: 10.1242/jcs.01660. |

TABLE 11

Cell Process-Cytoskeletal Regulation and Adhesion

Regulation of Actin Dynamics-related to many pathways, see for example integrin receptor binds ECM ligands, GPCR ligands, growth factors binding receptors (receptor tyrosine kinases)
Regulation of Microtubule Dynamics-related to many pathways above, see for example Wnt signaling, neutrophins/trophins
Adherens Junction Dynamics-related to many pathways above, see for example PI3K, MAPK

TABLE 12

List of Pairs of Signaling Pathway Activator Agents and Targeted Therapeutic Agents That Affect the Same Signaling Pathway

| Pathway | Ligand | Targeted Therapy | Pathway | Ligand | Targeted Therapy |
|---|---|---|---|---|---|
| HER2/HER1 | EGF | Trastuzumab | ALK | FAM150A | Crizotinib |
| HER2/HER1 | EGF | Pertuzumab | ALK | FAM150A | Ceritinib |
| HER2/HER1 | EGF | MEDI4276 | ALK | FAM150A | Brigatinib |
| HER2/HER1 | EGF | ONT-380 | ALK | FAM150A | Alectinib |
| HER2/HER1 | EGF | Lapatinib | ALK | FAM150A | AZD5363 |
| HER2/HER1 | EGF | Neratinib | ALK | FAM150A | Afuresertib |
| HER2/HER1 | EGF | Afatinib | ALK | FAM150A | MK-2206 |
| HER2/HER1 | EGF | Duligotuzumab | ALK | FAM150A | Ipatasertib |
| HER2/HER1 | EGF | Dacomitinib | ALK | FAM150A | Everolimus |
| HER2/HER1 | EGF | Sapitinib | ALK | FAM150A | Ridaforolimus |
| HER2/HER1 | EGF | Poziotinib | ALK | FAM150A | Temsirolimus |
| HER2/HER1 | EGF | ASLAN001 | ALK | FAM150A | Selemetinib |
| HER2/HER3 | NRG1 | Trastuzumab | ALK | FAM150A | Cobimetinib |
| HER2/HER3 | NRG1 | Pertuzumab | ALK | FAM150A | GDC-0994 |
| HER2/HER3 | NRG1 | MEDI4276 | ALK | FAM150A | Taselisib |
| HER2/HER3 | NRG1 | ONT-380 | ALK | FAM150A | Alpelisib |
| HER2/HER3 | NRG1 | Lapatinib | ALK | FAM150A | Buparlisib |
| HER2/HER3 | NRG1 | Neratinib | ALK | FAM150A | AZD8186 |
| HER2/HER3 | NRG1 | Afatinib | ALK | FAM150A | AZD8835 |
| HER2/HER3 | NRG1 | Duligotuzumab | FGFR | bFGF | AZD4547 |
| HER3 | NRG1 | MM-121 | FGFR | bFGF | JNJ-42756493 |
| HER3 | NRG1 | MM-141 | FGFR | bFGF | BGJ398 |
| HER3 | NRG1 | LJM716 | FGFR | bFGF | AZD5363 |
| HER3 | NRG1 | U3-1287 (AMG888) | FGFR | bFGF | Afuresertib |
| HER3 | NRG1 | TK-A3/TK-A4 | FGFR | bFGF | MK-2206 |
| HER3 | NRG1 | Lumretuzumab | FGFR | bFGF | Ipatasertib |

TABLE 12-continued

List of Pairs of Signaling Pathway Activator Agents and Targeted Therapeutic Agents That Affect the Same Signaling Pathway

| Pathway | Ligand | Targeted Therapy | Pathway | Ligand | Targeted Therapy |
|---|---|---|---|---|---|
| HER3 | NRG1 | REGN1400 | FGFR | bFGF | Everolimus |
| HER3 | NRG1 | AV-203 | FGFR | bFGF | Ridaforolimus |
| HER3 | NRG1 | AZD5363 | FGFR | bFGF | Temsirolimus |
| HER3 | NRG1 | Afuresertib | FGFR | bFGF | Selemetinib |
| HER3 | NRG1 | MK-2206 | FGFR | bFGF | Cobimetinib |
| HER3 | NRG1 | Ipatasertib | FGFR | bFGF | GDC-0994 |
| HER3 | NRG1 | Everolimus | FGFR | bFGF | Taselisib |
| HER3 | NRG1 | Ridaforolimus | FGFR | bFGF | Alpelisib |
| HER3 | NRG1 | Temsirolimus | FGFR | bFGF | Buparlisib |
| HER3 | NRG1 | Selemetinib | FGFR | bFGF | AZD8186 |
| HER3 | NRG1 | Cobimetinib | FGFR | bFGF | AZD8835 |
| HER3 | NRG1 | GDC-0994 | IGFR | IGF | Linsitinib |
| HER3 | NRG1 | Taselisib | IGFR | IGF | Dalotuzumab |
| HER3 | NRG1 | Alpelisib | IGFR | IGF | MEDI-573 |
| HER3 | NRG1 | Buparlisib | IGFR | IGF | Ganitumab |
| HER3 | NRG1 | AZD8186 | IGFR | IGF | MM-141 |
| HER3 | NRG1 | AZD8835 | IGFR | IGF | AZD5363 |
| EGFR | EGF | Neratinib | IGFR | IGF | Afuresertib |
| EGFR | EGF | Gefitinib | IGFR | IGF | MK-2206 |
| EGFR | EGF | Erlotinib | IGFR | IGF | Ipatasertib |
| EGFR | EGF | Cetuximab | IGFR | IGF | Everolimus |
| EGFR | EGF | Panitumumab | IGFR | IGF | Ridaforolimus |
| EGFR | EGF | REGN955 | IGFR | IGF | Temsirolimus |
| EGFR | EGF | MM-151 | IGFR | IGF | Selemetinib |
| EGFR | EGF | Osimertinib | IGFR | IGF | Cobimetinib |
| EGFR | EGF | Rociletinib | IGFR | IGF | GDC-0994 |
| EGFR | EGF | Duligotuzumab | IGFR | IGF | Taselisib |
| EGFR | EGF | Lapatinib | IGFR | IGF | Alpelisib |
| EGFR | EGF | Afatinib | IGFR | IGF | Buparlisib |
| EGFR | EGF | AZD5363 | IGFR | IGF | AZD8186 |
| EGFR | EGF | Afuresertib | IGFR | IGF | AZD8835 |
| EGFR | EGF | MK-2206 | SMO | SAG1.3 | Vismodegib |
| EGFR | EGF | Ipatasertib | SMO | SAG1.3 | Itraconazole |
| EGFR | EGF | Everolimus | SMO | SAG1.3 | Sonidegib |
| EGFR | EGF | Ridaforolimus | Patched1 | SHH | Vismodegib |
| EGFR | EGF | Temsirolimus | Patched1 | SHH | Itraconazole |
| EGFR | EGF | Selemetinib | Patched1 | SHH | 5E1 |
| EGFR | EGF | Cobimetinib | Frizzled | Wnt | LGK974 |
| EGFR | EGF | GDC-0994 | Frizzled | Wnt | Vantictumab |
| EGFR | EGF | Taselisib | Frizzled | Wnt | Ipafricept |
| EGFR | EGF | Alpelisib | Notch | γ-secretase | Semagacestat |
| EGFR | EGF | Buparlisib | Notch | γ-secretase | Tarextumab |
| EGFR | EGF | AZD8186 | Notch | γ-secretase | Brontictuzumab |
| EGFR | EGF | AZD8835 | c-MET/HGF | HGF | Ipatasertib |
| c-MET/HGF | HGF | SGX-523 | c-MET/HGF | HGF | Everolimus |
| c-MET/HGF | HGF | Onartuzumab | c-MET/HGF | HGF | Ridaforolimus |
| c-MET/HGF | HGF | Cabozantinib | c-MET/HGF | HGF | Temsirolimus |
| c-MET/HGF | HGF | Volitinib | c-MET/HGF | HGF | Selemetinib |
| c-MET/HGF | HGF | Tivantinib | c-MET/HGF | HGF | Cobimetinib |
| c-MET/HGF | HGF | Capmatinib | c-MET/HGF | HGF | GDC-0994 |
| c-MET/HGF | HGF | Emibetuzumab | c-MET/HGF | HGF | Taselisib |
| c-MET/HGF | HGF | Rilotumumab | c-MET/HGF | HGF | Alpelisib |
| c-MET/HGF | HGF | Ficlatuzumab | c-MET/HGF | HGF | Buparlisib |
| c-MET/HGF | HGF | AZD5363 | c-MET/HGF | HGF | AZD8186 |
| c-MET/HGF | HGF | Afuresertib | c-MET/HGF | HGF | AZD8835 |
| c-MET/HGF | HGF | MK-2206 | TGFbR | TGFb | SB431542 |
| PDGFR | PDGF | JI-101 | TGFbR | TGFb | EW-7197 |
| PDGFR | PDGF | Ponatinib | TGFbR | TGFb | RepSox |
| PDGFR | PDGF | Sunitinib | PDGFR | PDGF | pazopanib |
| PDGFR | PDGF | Imatinib | | | |

Therapeutic agents can include without limitations agents that are targeted to a particular cellular pathway and/or agents that inhibit cell proliferation or cause cell killing. Examples of pathways that therapeutic agents target include MAPK-PK, RAS/RAF, RHO, FAK1, MEK/MAPK, MAK, MKK, AKT, EGF receptor, Her2 receptor, Her 3 receptor, Her 4 receptor, estrogen receptors, progesterone receptors, androgen receptors, PDGF receptor, GPER30, PIK3/PTEN, VEGF receptor pathway inhibitors, cell adhesion, TGFbeta/SMAD, WNT, Hedgehog/GLI, HIF1 alpha, JAK/STAT, Notch, control of G1/S transition, DNA damage control, and apoptosis. In some embodiments, the therapeutic agents target cellular pathways involved in cell cycle regulation. Exemplary targeted therapeutic agents that affect cell cycle regulation include those targeted to CDK4, CDK6, PD-1, and cyclins (e.g., cyclins A, B, C, D, E, or F, and G1/S cyclins). In some embodiments, the targeted therapeutic agents target aromatase enzyme.

In other embodiments, the therapeutic agents are selected from a number of small molecule and antibody drugs such as cetuximab, erlotinib, gefitinib, lapatinib, pazopanib, trastuzumab, fulvestrant, tamoxifen, letrozole, anastrozole, exemestane, everolimus, abiraterone, bicalutamide, bortezomib, vemurafenib, ipilimumab, Pertuzumab, MEDI4276, ONT-380, Neratinib, Afatinib, Duligotuzumab, Dacomitinib, Sapitinib, Poziotinib, ASLAN001, MM-111 MM-121, MM-141, LJM716, U3-1287 (AMG 888), TK-A3/TK-A4, Lumretuzumab, REGN1400, AV-203, AZD5363, Afuresertib, MK-2206, Ipatasertib, Ridaforolimus, Temsirolimus, Selemetinib, Cobimetinib, GDC-0994, Taselisib, Alpelisib, Buparlisib, AZD8186, AZD8835, Panitumumab, REGN955, MM-151, Osimertinib, Rociletinib, AZD5363, SGX-523, Onartuzumab, Cabozantinib, Volitinib, Tivantinib, Capmatinib, Emibetuzumab, Rilotumumab, Ficlatuzumab, SAR125844, emibetuzumab, Sym015, AMG337, JNJ-61186372, glesatinib, 1202, LY3023414, Gedatolisib, JI-101, Ponatinib, Sunitinib, Crizotinib, Ceritinib, Brigatinib, Alectinib, BGJ398, Linsitinib, Quizartinib, R428 (BGB324), gilteritinib, Vismodegib, Itraconazole, 5E1, LGK974, Semagacestat, Cobimetinib, AZD4547, JNJ-42756493, Dalotuzumab, MEDI-573, Ganitumab, Sonidegib, Vantictumab, Ipafricept, Tarextumab, Brontictuzumab, SB431542, EW-7197, RepSox, AZD9291, Rociletinib, abraxane, brentuximab vedoton, ofatumumab, bevacizumab, alemtuzumab, bicalutamide, gemcitabine, imatinib, ixabepilone, romidepsin, cabrazitaxel, sorafenib, infliximab, lenalidomide, rituximab, dasatinib, nilotinib, temozolomide, bortezomib, azacitidine, tepotinib, lorlatinib, merestinib, RG6114, tucantinib, pazopanib, crizotinib, vemurafenib, goserelin acetate, abiraterone, a BH3 mimetic, navitoclax, anastrozole, letrozole, an aromatase inhibitor, ixabepilone, aflibercept, temsirolimus, irbritumomab, abiraterone, custirsen, enzalutamide, nivolumab, palbociclib, regorafenib, entinostat, ARN-509, ARN-810, BIND-014, dabrafenib, daratumumab, lambrolizumab, LDK378, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof. The targets of these therapeutic agents are known. Additional combinations of therapeutic agents can be selected using the Chou and Talalay method (Chou, Cancer Res., 70(2):440-446 (2010)).

In some embodiments, the therapeutic agent is targeted to a cell surface receptor that is a member of a cellular pathway. These samples can be contacted with a therapeutic agent before the sample is activated with an activator agent or perturbant of the pathway. In other embodiments, the activator agent or perturbant comprises a specific growth factor, vascular endothelial growth factors, phosphatidyl inositol, epidermal growth factors, hepatocyte growth factors, m-CSF, RANK ligand, Tumor Necrosis Factors (TNF-α), neuregulin, estrogen, progesterone, folate, adenosine triphosphate, and FAS Ligand, Platelet derived growth factors (PDGF), or other agents of cellular pathway or signaling perturbation such as the subject's plasma or serum, Na+, K+, Mg+, Cl-, Ca+2, glucose, glutamine, histidine, mannitol, and tryptophan, antibiotics (rapamycin), essential and non-essential amino acids, vitamins, other organic compounds, trace minerals and inorganic salts, serum, cell extracts, fractionated cell extracts or fractionated serum, extracellular signaling factors, intracellular signaling factors, insulin, transferrin, sodium selenite, hydrocortisone, ethanolamine, phosphophorylethanoloamine, triidothyronine, sodium pyruvate, L-glutamine. In other embodiments, therapeutic agents are those that affect diseased cells by inhibiting cell proliferation, enhancing cell killing, and rendering the cell unresponsive or less responsive to signals that lead to a diseased state. Examples of such therapeutic agents include cyclophosphamide, 5-FU, capecitabine, and other pyrimidine drugs, others SN-38 metabolite analogs (Ex. irinotecan), taxols, and platinum containing drugs (Ex. cisplatin).

In some embodiments, the response of a sample to one or more of these agents can also be measured in the presence or absence of a growth factor that perturbs cell proliferation or of an anti-apoptotic agent. Growth factors that perturb cell proliferation include growth hormone, epidermal growth factor, vascular endothelial growth factor, platelet derived growth factor, hepatocyte growth factor, transforming growth factor, fibroblast growth factor, nerve growth factors, and others known to those practiced in the art. Anti-apoptotic agents include compounds that regulate anti-apoptotic proteins or pathways (e.g., taxols on Bcl-2 protein activity and Gefitinib for control of the anti-apoptotic Ras signaling cascade).

Suitable activator agents that affect the ERα signaling pathway are known in the art and disclosed herein, such as estradiol. In another embodiment, the viable cancer cells are further contacted with a confirming agent that inhibits estrogen related signaling pathway activity, such as a selective estrogen receptor down regulator. In another embodiment, the cancer cells are further contacted with a targeted therapeutic that targets the ERα signaling pathway and the effect of the targeted therapeutic on cell adhesion or attachment is measured. Suitable targeted therapeutics that target the ERα signaling pathway are known in the art and disclosed herein, such as fulvestrant and tamoxifen. The method can further comprise administering the targeted therapeutic to the subject.

Suitable activator agents that affect an ErbB signaling pathway are known in the art and disclosed herein. In one embodiment, the viable cancer cells are contacted with a confirming agent known to inhibit ErbB related signaling pathway signaling, such as 2C4 mouse monoclonal antibody or a tyrosine kinase inhibitor. In another embodiment, the viable cancer cells are further contacted with a targeted therapeutic that targets an ErbB signaling pathway and the effect of the targeted therapeutic on cell adhesion or attachment is measured. Suitable targeted therapeutics that target an ErbB signaling pathway are known in the art and disclosed herein. The method can further comprise administering the targeted therapeutic to the subject.

Table 13 below summarizes the pathways, drug targets, and targeted therapies intended to treat ErbB signaling pathway cancers.

TABLE 13

| Pathway | Drug Target | Drug |
|---|---|---|
| MAPK; PI3K/Akt | HER2 | Trastuzumab |
| | | Tucatinib |
| | | Pertuzumab |
| | HER3 | MM-121 |
| | | LJM716 |
| | | U3-1287 |
| | | (AMG 888) |
| | | TK-A3/TK-A4 |
| | | Lumretuzumab |
| | | REGN1400 |
| | | AV-203 |
| | HER1 & HER2 | Lapatinib |
| | | Neratinib |
| | | Afatinib |
| | HER1 & HER3 | Duligotuzumab |
| | HER2 & HER3 | MM-111 |
| | HER1, HER2, HER3 | Dacomitinib |
| | | Sapitinib |

TABLE 13-continued

| Pathway | Drug Target | Drug |
|---|---|---|
| | HER1, HER2, HER4 | Poziotinib ASLAN001 |
| MAPK | HER1 (homodimer) | Gefitinib Erlotinib Cetuximab Panitumumab REGN955 MM-151 |
| | HER1 (T790m+) | AZD9291 Rociletinib |

In various embodiments, the signaling pathway is selected from the group consisting of MAPK, RHO, AKT, FAK1, RAS/RAF, PI3K/PTEN, MAK, MKK, and MEK. Additional suitable signaling pathways include other signaling pathways disclosed herein. In various embodiments, the activator agent can be, for example, a protein, peptide, nucleic acid, metabolite, ligand, reagent, organic molecule, signaling factor, growth factor, biochemical, or combinations thereof.

Non-limiting examples of targeted therapeutics include cetuximab, erlotinib, gefitinib, lapatinib, pazopanib, trastuzumab, fulvestrant, tamoxifen, letrozole, anastrozole, exemestane, everolimus, abiraterone, bicalutamide, bortezomib, vemurafenib, ipilimumab, Pertuzumab, MEDI4276, ONT-380, Neratinib, Afatinib, Duligotuzumab, Dacomitinib, Sapitinib, Poziotinib, ASLAN001, MM-111 MM-121, MM-141, LJM716, U3-1287 (AMG 888), TK-A3/TK-A4, Lumretuzumab, REGN1400, AV-203, AZD5363, Afuresertib, MK-2206, Ipatasertib, Ridaforolimus, Temsirolimus, Selemetinib, Cobimetinib, GDC-0994, Taselisib, Alpelisib, Buparlisib, AZD8186, AZD8835, Panitumumab, REGN955, MM-151, Osimertinib, Rociletinib, AZD5363, SGX-523, Onartuzumab, Cabozantinib, Volitinib, Tivantinib, Capmatinib, Emibetuzumab, Rilotumumab, Ficlatuzumab, SAR125844, emibetuzumab, Sym015, AMG337, JNJ-61186372, glesatinib, 1202, LY3023414, Gedatolisib, JI-101, Ponatinib, Sunitinib, Crizotinib, Ceritinib, Brigatinib, Alectinib, BGJ398, Linsitinib, Quizartinib, R428 (BGB324), Gilteritnib, Vismodegib, Itraconazole, 5E1, LGK974, Semagacestat, Cobimetinib, AZD4547, JNJ-42756493, Dalotuzumab, MEDI-573, Ganitumab, Sonidegib, Vanticumab, Ipafricept, Tarextumab, Brontictuzumab, SB431542, EW-7197, RepSox, AZD9291, Rociletinib, abraxane, brentuximab vedoton, ofatumumab, bevacizumab, alemtuzumab, bicalutamide, gemcitabine, imatinib, ixabepilone, romidepsin, cabrazitaxel, sorafenib, infliximab, lenalidomide, rituximab, dasatinib, nilotinib, temozolomide, bortezomib, azacitidine, tepotinib, lorlatinib, merestinib, RG6114, tucantinib, pazopanib, crizotinib, vemurafenib, goserelin acetate, abiraterone, a BH3 mimetic, navitoclax, anastrozole, letrozole, an aromatase inhibitor, ixabepilone, aflibercept, temsirolimus, irbritumomab, abiraterone, custirsen, enzalutamide, nivolumab, palbociclib, regorafenib, entinostat, ARN-509, ARN-810, BIND-014, dabrafenib, daratumumab, lambrolizumab, LDK378, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof. In certain embodiments, the method further comprises administering the targeted therapeutic to the subject.

I. Sample Preparation and Culturing

Embodiments of the invention include systems, kits, and methods to determine the effectiveness of a therapeutic, monitor the effectiveness, or identify a dose of a therapeutic when administered to a subject's diseased cells.

Traditionally, disease has been classified by the tissue or organ that the disease affects. Due to better knowledge of the underlying mechanisms (e.g., genetic, autoimmune response, etc.), it is now understood that diseases which affect the same tissue/organ, or produce the same symptoms, may have different etiologies and may have heterogeneous gene expression profiles. In addition, it has been shown in many diseases that there are responders and non-responders to therapeutic agents. In embodiments, any disease type, for which responders and non-responders are identified, can be employed in the methods herein in order to predict or prognosticate whether a particular therapeutic drug combination of drugs will be effective for a particular individual, e.g. a determination whether the individual is a responder or a non-responder.

One example of a disease type that is known to be heterogeneous in nature and to have responders and many non-responders is cancer. Cancer is typically classified according to tissue type. However, a more accurate description of the heterogeneity of cancer is reflected in the different mutations of the different cancers. An even more accurate description of the heterogeneity of cancer is the actual functional, physiological result of the mutation in a particular patient's cells. For instance, breast cancer has different types and different mutations that cause cancer of this organ. Outcomes and treatments can be different based on whether the mutation causing the cancer is a gain of function (e.g., proto-oncogene causing increase protein production) or loss of function mutation (e.g., tumor suppressor) and in which gene. Due to the heterogeneity of a particular cancer, it would be expected that there would a heterogeneous response to a particular therapeutic agent. Embodiments of this invention allow the testing of a particular subject's cancer cells to a therapeutic agent or a panel of therapeutic agents to determine the efficacy of a specific therapeutic agent or the most effective therapeutic agent for a particular subject's cancer to select a treatment for the subject.

Embodiments of the invention include disease cell samples of cancer cells from individual subjects. Such cancer cells can be derived from, but not limited to, Acute Lymphoblastic Leukemia (ALL), Acute Myeloid Leukemia (AML), Adrenocortical Carcinoma, Anal Cancer, Appendix Cancer, Astrocytomas, basal cell carcinoma, Extrahepatic Bile Duct Cancer, Bladder Cancer, Bone Cancer, Osteosarcoma, Malignant Fibrous Histiocytoma, Brain Stem Glioma, Central Nervous System Atypical Teratoid/Rhabdoid Tumor, Central Nervous System Embryonal Tumors, Central Nervous System Germ Cell Tumors, Craniopharyngioma, Ependymoblastoma, Ependymoma, Medulloblastoma, Medulloepithelioma, breast cancer, Pineal Parenchymal Tumors of Intermediate Differentiation, Supratentorial Primitive Neuroectodermal Tumors, Pineoblastoma, Bronchial Tumors, Carcinoid Tumor, Cervical Cancer, Chronic Lymphocytic Leukemia (CLL), Chronic Myelogenous Leukemia (CML), Chronic Myeloproliferative Disorders, Colon Cancer, Colorectal Cancer, Cutaneous T-Cell Lymphoma, Ductal Carcinoma In Situ (DCIS), Endometrial Cancer, Esophageal Cancer, Esthesioneuroblastoma, Ewing Sarcoma, Extragonadal Germ Cell Tumor, Intraocular Melanoma, Retinoblastoma, fibrous histiocytoma, Gallbladder Cancer, Gastric Cancer, Gastrointestinal Carcinoid Tumor, Gastrointestinal Stromal Tumors (GIST), Gestational Trophoblastic Tumor, Glioma, Hairy Cell Leukemia, Heart Cancer, Hepatocellular Cancer, Langerhans Cell Histiocytosis, Hodgkin Lymphoma, Hypopharyngeal Cancer, islet cell tumors, Kaposi sarcoma, renal cell cancer, Laryngeal Cancer, Lip Cancer, Liver Cancer, Lobular Carcinoma In Situ (LCIS), Lung Cancer, Merkel cell carcinoma, Melanoma, mesothelioma, mouth cancer, multiple myeloma, Nasal Cavity and Paranasal Sinus Cancer, Nasopharyngeal Cancer, Neuroblastoma, Non-Hodgkin Lymphoma, Non-Small Cell Lung Cancer, Oral Cavity Cancer, Oropharyngeal Cancer, Ovarian Cancer, Pancreatic Cancer, Papillomatosis, Paraganglioma, Parathyroid Cancer, Penile Cancer, Pharyngeal Cancer, Pheochromocytoma, Pineal Parenchymal, Pituitary Tumor, Pleuropulmonary Blastoma, Prostate Cancer, rectal cancer, rhabdomyosarcoma, salivary gland cancer, squamous cell carcinoma, small intestinal cancer, testicular cancer, throat cancer, thyroid cancer, ureter cancer, urethral cancer, uterine cancer, vaginal cancer, vulvar cancer, and Wilm's tumor.

Autoimmune diseases are characterized by increased inflammation due to immune system activation against self antigens. Current therapies target immune system cells such as B cells and inflammatory molecules such as anti TNFα. Therapies can be broadly characterized as immune modulating or immunosuppressant. Drugs may be targeted to particular molecules such as TNF alpha, Integrins, sphingosine receptors, and interleukins. Other drugs act as anti-inflammatory agents such as corticosteroids. In yet other cases, drugs are immunosuppressants such as mercaptopurines and cyclophosphamide. With respect to autoimmune conditions, peripheral blood cells may be examined for the response to a certain therapeutic. In other embodiments, tissue samples of the site of inflammation, for example, synovial tissue in rheumatoid arthritis or colon tissue for ulcerative colitis.

For example, some patients with rheumatoid arthritis are known to be non-responders to anti-TNFα antibodies. In an embodiment, peripheral blood cells can be obtained from a patient suspected as having RA and a decrease in cell signaling ability of the patient's TNF Receptor and associated MAPK pathway can be used to determine whether the patient is likely to be a responder or non-responder to an immunomodulating or immunosuppressant compound. Likewise other therapeutics such as those targeting to IL-6, Interferon alpha, Interferon gamma, and the like may be tested in the same way. In other embodiments, it is known that patients that have multiple sclerosis are nonresponders to interferon beta. Cell samples from subjects can be tested against a panel of drugs to see which if any of the drugs are effective for a particular subject by inducing a change in a cellular physiological parameter. Examples of advantageous outcomes would be a reduction in cellular inflammation parameters, as determined by the American College of Rheumatology (ACR) criteria or an increase in cell adhesion for strengthening the blood-brain barrier function.

In other embodiments, patients may have a disease caused by infection of cells by a microorganism, a foreign body, or a foreign agent. Blood cells or tissue samples infected with a microorganism may be evaluated for responsiveness to various antibiotics, antivirals, or other therapeutic candidates. For example, there are a number of different therapeutic agents for hepatitis C infection that reduce viral function, infected tissue samples can be contacted with one or more therapeutic agents and a change in a cellular physiological parameter is detected. Therapeutic agents are selected that provide a change in a cellular physiological parameter of the infected tissue, and/or a therapeutic agent that provides a change in a cellular physiological parameter at the lowest dose. Outcomes such as increase in cell survival or increase in cell growth would be considered advantageous. In other embodiments where the therapeutic is designed to effect the human cell directly such as by blocking viral entry via a specific receptor type or activation of a cellular pathway, the patient cell could be tested for receptor binding or pathway activation by said therapeutic as described in other embodiments herein.

In embodiments, the cell samples can be obtained before therapy is initiated, during therapy, after therapy, during remission, and upon relapse. The methods as described herein are useful to predict therapeutic efficacy prior to treatment, during treatment, when a patient develops resistance, and upon relapse. The methods of the disclosure are also useful as to predict responders or non-responders to a therapeutic agent or combination of agents.

In certain embodiments, the cells are not contacted or treated with any kind of fixative, or embedded in paraffin or other material, or any detectable label. In other embodiments, it is preferred that the cells remain whole, viable and/or label free. Thus, viable primary cells can be used as the cell sample. In some other embodiments, a cell sample is provided for both the diseased tissue and healthy tissue. In some embodiments, the cell sample is provided in both viable and fixed form. A cell sample provided in fixed form can serve as a control for comparison to the viable cells that are analyzed in accord with the methods as described herein particularly for improved identification and correlation of additional biomarkers.

In other embodiments of the invention, cells from an individual subject are used to determine therapeutic effectiveness. Cells can be collected and isolated by well-known methods (i.e., swab, biopsy, etc.). Both diseased and non-diseased cells can be used. Non-diseased cells can be used as a negative control, a baseline measure, a comparison for measures over time, etc. In embodiments, a control sample of tissue cells from the same subject may also be obtained. A control sample may be taken from another healthy tissue in the subject or from healthy tissue from the same organ as the diseased tissue sample or more preferably healthy tissue is taken from an individual without disease. Diseased cells are cells extracted from a tissue with active disease. In an embodiment, diseased cells can be tumor cells, such as breast cancer cells. Cancerous cells do not necessarily have to be extracted from a tumor. For instance, leukemic cells can be collected from the blood of a patient with leukemia. Cells can be collected from different tissue sites such as the sites of metastasis, circulating tumor cells, primary tumor sites, and recurrent tumor sites, and cellular responsiveness compared to one another. In another embodiment, diseased cells can be extracted from a site of autoimmune disease, such as rheumatoid arthritis. In certain embodiments, the number of cells in each tissue sample is preferably at least about 5000 cells. In other embodiments, the cell number in the tissue sample may range from about 5000 to 1 million cells or greater. Cell samples include isolation from, but are not limited to, blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, marrow, or hair. In some other embodiments, the cell samples can contain or be derived from patient serum, fractions thereof, organoids, fibroblasts, stromal cells, mesenchymal cells, epithelial cells, white blood cells, red blood cells, B cells, T cells, immune cells, stem cells, or combinations thereof.

In one embodiment, the extraction of cells from a subject is performed at the same location as method of evaluating signaling pathway activity (e.g, the CReMS system described herein) (e.g., at a laboratory, hospital). As such, the cells can be suspended or preserved in a well-known transfer medium to bridge the time from subject to biosensor. In another embodiment, the extraction of cells from a subject is at a different location from the method of evaluating signaling pathway activity (e.g, the CReMS system described herein). Once obtained the cell samples are maintained in a medium that retains the cell viability. Depending on the length of time for transportation to the site of analysis, different media may employed. In embodiments, when transportation of the tissue sample may require up to 10 hours, the media has an osmolality of less than 400 mosm/L and comprises Na+, K+, Mg+, Cl−, Ca+2, glucose, glutamine, histidine, mannitol, and tryptophan, penicillin, streptomycin, contains essential amino acids and may additionally contain non-essential amino acids, vitamins, other organic compounds, trace minerals and inorganic salts, serum, cell extracts, or growth factors, insulin, transferrin, sodium selenite, hydrocortisone, ethanolamine, phosphophorylethanoloamine, triiodothyronine, sodium pyruvate, L-glutamine, to support the proliferation and plating efficiency of human primary cells. Examples of such a media include Celsior media, Roswell Park Memorial Institute medium (RPMI), Hanks Buffered Saline, and McCoy's 5A, Eagle's Essential Minimal Media (EMEM), Dulbecco's modified Eagle's medium (DMEM), Leibovitz L-15, or modifications thereof for the practice of primary cell care. In embodiments, the media and containers are endotoxin free, nonpyrogenic and DNase- and RNase-free.

In other embodiments, the diseased cells obtained from a tissue specimen of an individual subject are extracted using steps that include mincing and enzyme digestion of a tissue specimen, separation of extracted cells by cell type, and/or culturing of the extracted cells. The culturing reagent can include various supplements, for example, patient serum or patient derived factors.

A further aspect includes a method of extracting organoids from a tissue specimen, which can subsequently be used to determine the efficacy of a therapeutic agent in an individual subject. Such a method comprises mincing and enzyme digestion steps. A further aspect includes a method of culturing organoids from a tissue specimen, which can subsequently used to determine the efficacy of a therapeutic agent in an individual subject. Such a method comprises mincing, enzyme digestion, separation by cell type, and culturing steps. A further aspect may include the specific recombination of the so separated cells to perform the methods described herein.

In certain embodiments, prior to assessing signaling pathway activity in a sample of viable cells from a subject, the cells are first cultured in a media free of serum and any agents that could perturb the signaling pathway to be assessed (i.e., the signaling pathway addressed by a targeted therapeutic being evaluated for effectiveness in the subject's cells) such that the cells are synchronized with respect to physiological state and pathway activation. In certain embodiments, the cell sample is cultured in a media free of serum and growth factors. In other embodiments, the cells are cultured in a media that maintains functional cellular cyclic adenosine monophosphate (cAMP), functional thyroid receptors and/or functional G-protein-coupled receptors (or any combination of two or three of the aforementioned properties) in order to support proliferation and plating efficacy of human primary cells.

In one embodiment, the sample of viable cancer cells is cultured in a media comprising growth factors and free of serum. In another embodiment, the sample of viable cancer cells is also cultured in a media comprising an anti-apoptotic agent and free of serum. Non-limiting examples of anti-apoptotic agents include kinase inhibitors, protease inhibitors, stress inhibitors, death receptor inhibitors, cytochrome C inhibitors, anoikis inhibitors, including Rho-associated kinase inhibitors, ALK5 inhibitors, caspase inhibitors, matrix metalloprotease inhibitors, redox buffering agents, reactive oxygen species inhibitors, TNFα inhibitors, TGFβ inhibitors, cytochrome C release inhibitors, carbonic anhydrase antagonists without calcium channel activation, integrin stabilizers, integrin ligands, Fas inhibitors, FasL inhibitors, Bax inhibitors and Apaf-1 inhibitors.

Additional suitable culturing conditions for preparation of a primary cell sample, e.g., a viable cancer cell sample obtained from a subject, are described in detail in PCT Application No. PCT/US2016/057923, the entire contents of which is expressly incorporated herein by reference.

J. Sample Analysis

Systems and methods of the invention utilize a system referred to herein as a cellular response measurement system (CReMS). CReMS refers to a device (e.g., biosensor) that can quantitatively determine a change in a physiological parameter in a cell, in and between cells, and between cells and the instrumentation device. A change in a physiological parameter is measured by determining change in an analyte (including non-limiting examples such as extracellular matrix, cell signaling molecule, or cell proliferation, tissue, cells, metabolites, catabolites, biomolecules, ions, oxygen, carbon dioxide, carbohydrates, proteins etc.). In embodiments, the biosensor is measuring a change in the physiological parameter in isolated whole label free viable cells. In embodiments, a biosensor is selected that can measure an expected change due to the type of therapeutic and/or activator agent.

An example of a CReMS is a biosensor. Examples of biosensors are electrochemical biosensors, electrical biosensors, optical biosensors, mass sensitive biosensors, thermal biosensors, and ISFET biosensors. Electrochemical biosensors measure potentiometric, amperometric and/or voltammetric properties. Electrical biosensors measure surface conductivity, impedance, resistance or electrolyte conductivity. Optical biosensors measure fluorescence, absorption, transmittance, density, refractive index, and reflection. Mass sensitive biosensors measure resonance frequency of piezocrystals. Thermal biosensors measure heat of reaction and adsorption. ISFET biosensors measure ions, elements, and simple molecules like oxygen, carbon dioxide, glucose, and other metabolites of interest in the life sciences. In embodiments, the biosensor is selected from the group consisting of an impedance device, a photonic crystal device, an optical waveguide device, a surface plasmon resonance device, quartz crystal resonators/microbalances, and a microcantilever device. In embodiments, an optical biosensor can comprise an optical transducer for converting a molecular recognition or molecular activation event in a living cell, a pathogen, or combinations thereof. In a specific embodiment, the device is an impedance device.

In an example of a biosensor used to measure protein or other in vitro biomolecular interactions, the capture of a specific protein mass is translated into meaningful biochemical and biophysical values. Applying a simple calculation with the captured mass involving the molecular weight of the specific protein captured, the number of moles are evaluated, leading to equilibrium binding constants and other interaction descriptive values known to those experienced in the art. In an example of a biosensor used for cell assays, specific adhesion molecules on the cell surface modulate their attachment and morphology close to the surface of the sensor and other nearby cells upon application of external chemical or other stimulus via specific cellular pathways.

The biosensor can detect these modulations that can be selected in such a way as to be unique to the stimulus and pathway within the cell employed to respond to stimuli. When designed properly, the biosensor result for said cell assay can be exquisitely quantitative in molecular and functional terms. Said biosensor result can be a temporal pattern of response for further uniqueness. Biomolecular activators or perturbants known to turn on and turn off specific pathways within the cell can be used as controls for determining the specificity of the CReMS biosensor signal. Methods for curve deconvolution of the temporal response of the bio sensor result (e.g. non-linear Euclidean comparison with control responses) can be applied to further more finely detail specific cellular responses. Use of titrating external stimuli in a cellular biosensor assay can also provide further biochemical and biophysical parameter description.

One example of a label-free sensor is a high frequency quartz resonator or quartz crystal microbalance (QCM) or resonating cantilever. The resonator includes a quartz crystal with a patterned metal electrode upon its surface. The quartz material has well-characterized resonance properties when a voltage is applied. By applying an alternating voltage to the electrodes at a particular frequency, the crystal will oscillate at a characteristic frequency. The oscillation frequency is modulated in quantitative ways when mass is captured on the sensor surface; additional mass results in lower resonator frequency. Therefore, by measuring small changes in the resonant frequency of the quartz oscillator, very small changes in deposited mass can be measured without attaching a label to the biomolecule or cell under study.

Ion Selective Field Effect Transistor (ISFET) devices are miniaturized, nanoscale, devices that are capable of measuring selected ions, elements, and simple molecules like oxygen, carbon dioxide, glucose, and other metabolites of interest in the life sciences. They have been extensively described at the electromechanical operational level as well as at the bioapplication level. To date they have not been described for the use with a specific patient's cells to discern response or resistance or temporal patterns thereof to proposed therapeutic intervention in disease processes.

Optical biosensors are designed to produce a measurable change in some characteristic of light that is coupled to the sensor surface. The advantage of this approach is that a direct physical connection between the excitation source (the source of illumination of the sensor), the detection transducer (a device that gathers reflected or transmitted light), and the transducer surface itself is not required. In other words, there is no need for electrical connections to an optical biosensor, simplifying methods for interfacing the sensor with fluid required for stabilizing and studying most biological systems. Rather than detecting mass directly, all optical biosensors rely on the dielectric permittivity of detected substances to produce a measurable signal. The changes in dielectric permittivity are related to the difference in ratio of the speed of light in free space to that in the medium. This change essentially represents the refractive index of the medium. The refractive index is formally defined as the square root of the dielectric constant of a medium (see Maxwell's equation for more explicit treatment of this relationship). An optical biosensor relies on the fact that all biological material, such as proteins, cells, and DNA, have a dielectric constant that is higher than that of free space. Therefore, these materials all possess the intrinsic ability to slow down the speed of light that passes through them. The optical biosensors are designed to translate changes in the propagation speed of light through a medium that contains biological material into a quantifiable signal that is proportional to the amount of biological material that is captured on the sensor surface.

Different types of optical biosensors include but are not limited to ellipsometers, surface plasmon resonant (SPR) devices, imaging SPR devices, grating coupled imaging SPR devices, holographic biosensors, interference biosensors, Reflectometric Interference Spectroscopy (RIFS), Colorimetric Interference Biosensors, Difference Interferometers, Hartman Interferometers, Dual Polarization Interferometers (DPI), Waveguide sensor chips, Integrated Input Grating Coupler devices, Chirped Waveguide Grating devices, Photonic crystal devices, Guided Mode Resonant Filter devices based upon Wood's Anomalies, Trianglular Silver Particle Arrays. And further include devices that measure a variety of wavelengths of the electromagnetic spectrum including but not limited to visible, ultraviolet, near infrared, and infrared. The modes of operation include but are not limited to scattering, inelastic scattering, reflection, absorbance, Raman, transmittance, transverse electric wave, and transverse magnetic wave.

The surface plasmon resonance device is an optical biosensor that measures binding events of biomolecules at a metal surface by detecting changes in the local refractive index. In general, a high-throughput SPR instrument consists of an auto-sampling robot, a high resolution CCD (charge-coupled device) camera, and gold or silver-coated glass slide chips each with more than 4 array cells embedded in a plastic support platform. SPR technology exploits surface plasmons (special electromagnetic waves) that can be excited at certain metal interfaces, most notably silver and gold. When incident light is coupled with the metal interface at angles greater than the critical angle, the reflected light exhibits a sharp attenuation (SPR minimum) in reflectivity owing to the resonant transfer of energy from the incident light to a surface plasmon. Binding of biomolecules at the surface changes the local refractive index and results in a shift of the SPR minimum. By monitoring changes in the SPR signal, it is possible to measure binding activities at the surface in real time.

Since SPR measurements are based on refractive index changes, detection of an analyte is label free and direct. The analyte does not require any special characteristics or labels (radioactive or fluorescent) and can be detected directly, without the need for multistep detection protocols. Measurements can be performed in real time, allowing collection of kinetic data and thermodynamic data. Lastly, SPR is capable of detecting a multitude of analytes over a wide range of molecular weights and binding affinities. Thus, SPR technology is quite useful as a cellular response measurement system.

A CReMS for the measurement of complex impedance changes (delta Z, or dZ) of live patient cells is described in this embodiment where impedance (Z) is related to the ratio of voltage to current as described by Ohm's law ($Z=V/I$). For example a constant voltage is applied to electrodes to which patient cells are attached, producing a current that at differential frequencies flows around, between cells and through cells. This CReMS is sensitive to the local ionic environment at the electrode interface with the cells and detects these changes as a function of voltage and current fluctuations. Physiologic changes of the cells as a result of normal function or activation thereof result in quantifiable changes to the flow of current around the electrodes and influence the magnitude and characteristics of the signal measured in such a CReMS.

In certain embodiments, the biosensor detects a change in global phenotype with event specificity. A global phenotype comprises one or more cellular response parameters selected from the group consisting of pH, cell adhesion, cell attachment pattern, cell proliferation, cell signaling, cell survival, cell density, cell size, cell shape, cell polarity, $O_2$, $CO_2$, glucose, cell cycle, anabolism, catabolism, small molecule synthesis and generation, turnover, and respiration, ATP, calcium, magnesium, and other charged ions, proteins, specific pathway member molecules, DNA and or RNA in various cellular compartments, genomics, and proteomics, post-translational modifications and mechanisms, levels of secondary messenger, cAMP, mRNA, RNAi, microRNAs and other RNA with physiologic function, and combinations thereof. With respect to event specificity, a cellular parameter is selected that reflects a change in a cell sample that is an expected change for that type of therapeutic and/or activator agent. For example, if a therapeutic agent is known to target a cytoskeletal element, a cell contacted with such an agent would be expected to show a change in cell adhesion in the presence of the agent.

In other embodiments, the change in attachment pattern is a change in cell adhesion. In some cases, the change in cell adhesion is indicated by a change in a refractive index or a change in impedance. In yet other embodiments, the change in attachment pattern is a change in basal morphology, a change in cell density, or a change in cell size or cell shape. In a specific embodiment, the change in basal morphology is a change in cell polarity. In embodiments, a decrease in cell signaling indicates a change in cytoskeletal organization.

In other embodiments, the methods of the disclosure provide for analysis of cell samples that are label free and that can be measured in real time. In one embodiment, the cell sample analyzed is a label free, viable, and not subject to any treatments to fix the cells. In another embodiment, the therapeutic and/or activator agents used in the methods and kits of the disclosure are also label free. To date label free methods have not been applied to determining therapeutic efficacy in effective ways.

Label free assays can reduce the time and cost of screening campaigns by reducing the time and misleading complications of label assays. Assays that can identify and quantify gene expression, gene mutation, and protein function are performed in formats that enable large-scale parallelism. Tens-of-thousands to millions of protein-protein or DNA-DNA interactions may be performed simultaneously more economically with label-free assays.

In contrast to the large variety of labeled methods, there are relatively few methods that allow detection of molecular interaction and even fewer still for cellular function without labels. Label-free detection removes experimental uncertainty created by the effect of the label on molecular folding of therapeutic and activator agents, blocking of active sites on cells, or the inability to find an appropriate label that functions equivalently for all molecules in an experiment that can be placed effectively within a cell. Label-free detection methods greatly simplify the time and effort required for assay development, while removing experimental artifacts from quenching, shelf life, and background interference.

Labels are a mainstay of biochemical and cell-based assays. Labels comprise the majority of all assay methods and have to overcome several problems, especially in the context of the study of complex dynamic activities in live human cells. Use of radioactive labels create large quantities of contaminated materials and must be used in specialized facilities with regulatory methods to prevent harm (at the cellular level) to those that use them. The excitation/emission efficiency of fluorophores is degraded by time and exposure to light, reducing the ability of the label to be accurate and precise, and requiring that assays be read once only in an end point manner so that temporal information cannot be obtained. All label-based assays require a significant amount of time to develop a process for attaching the label in a homogenous and uniform manner, determining that the label will be linearly quantitative, and will not interfere or affect the interaction or process being measured. The uniform application of labels in complex mixtures is complicated by the presence of all the molecules that are needed for the process to proceed naturally. Addition of the label only allows for visualization of that molecule function indirectly, not the entire system function directly (i.e. some extended assumptions may be necessary). Cellular activities are even more difficult to measure accurately with labels. A useful test must figure out how the label will get onto the right molecule, the right way, in the right location with respect to the cell, and be certain that the label is not disturbing the normal cellular processes.

Label-free detection generally involves the use of a transducer that is capable of directly measuring some physical property of a biological compound or bioentity such as a DNA molecule, peptide, protein, or cell. All biochemical molecules and cells have finite physical values for volume, mass, viscoelasticity, dielectric permittivity, heat capacity and conductivity that can be used to indicate their presence or absence, increase or decrease, and modification using a type of sensor. Additionally living systems utilize molecules to provide energy and carry out their life processes, such as $O_2/CO_2$ consumption/generation, glucose production/consumption, ATP production/consumption that cause measurable changes such as pH in their environ over finite periods of time. The sensor functions as a transducer that can convert one of these physical properties into a quantifiable signal such as a current or voltage that can be measured.

In some cases, in order to use a transducer as a bio sensor, the surface of the transducer must have the ability to selectively capture specific material such as a protein or specific cell type, while not allowing undesired material to attach. Selective detection capability is provided by building of a specific coating layer of chemical molecules on the surface of the transducer. The material that is attached to the sensor surface is referred to as the sensor coating while the detected material is called the analyte. Thus, in some cases, a biosensor is the combination of a transducer that can generate a measurable signal from material that attaches to the transducer, and a specific recognition surface coating containing a receptor ligand that can bind a targeted analyte from a test sample.

In certain embodiments, a coating is selected for a biosensor that is associated with a particular cellular component or pathway. For example, in those cases, where the cellular physiological parameter is change in cell adhesion, a coating is selected that provides for adhesion of the cells in the cell sample to the biosensor surface. In embodiments, the coating that enhances adhesion of the cells to the biosensor includes extracellular matrix, fibronectin, integrins and the like. In other embodiments, a coating is selected that binds to a particular cell type based on a cell surface marker. In embodiments, such cell surface markers include clusters of differentiation (CD), CD20, CD30, EGFR, HER2 receptor, HER3 receptor, HER4 receptor, VEGFR, and other cell surface cancer biomarkers.

In other embodiments, the biosensor is coated with a biomolecular coating. CReMS surfaces contacting cells may contain a biomolecular coating prior to addition of cells, during addition of cells, or after addition of cells. The coating material may be synthetic, natural, animal derived, mammalian, or created by cells placed on the sensor. For example, a biomolecular coating can comprise an extracellular matrix component known to engage integrins, adherins, cadherins and other cellular adhesion molecules and cell surface proteins (e.g., fibronectin, laminin, vitronectin, collagens, IntercellularCAMs, VascularCAMs, MAdCAMs), or a derivative thereof, or can comprise a biochemical such as polylysine or polyornithine, which are polymeric molecules based on the naturally occurring biochemicals lysine and ornithine, polymeric molecules based on naturally occurring biochemicals such as amino acids can use isomers or enantiomers of the naturally-occurring biochemical, antibodies, fragments or peptide derivatives of antibodies, complement determining region (CDR), designed to attach specific cell surface proteins to the biosensor.

Methods for attaching viable cells to a microplate may include, for example, coating the sensor microplate surface with a reactive molecule having one end designed to interact with the surface of the biosensor, and another end that designed to react with functional groups on a peptide. For example, when using a gold-coated biosensor, the reactive molecule could include a sulfur atom or other chemical moiety designed to chemically interact with the biosensor surface. The other end of the molecule can specifically react with, for example, the amide or carboxy groups on a peptide.

Methods for attaching viable (e.g., primary cells) to a biosensor surface are also described in detail in PCT Application No. PCT/US2016/0579023, the entire contents of which is expressly incorporated herein by reference.

In another example, the biosensor surface can be coated with molecules that adhere through van der waals forces, hydrogen bonding, electrostatic attraction, hydrophobic interaction, or any combination of these such as one practiced in the art might use to apply proteins. An extracellular matrix (ECM) molecule can also be added to the first surface molecular coating. Humphries 2006 Integrin Ligands at a Glance. Journal of Cell Science 119 (19) p 3901-03 describes adhesion molecules useful in this invention. Additional ECM molecules that can be used to contact specific cell adhesion molecules include those described in Table 1 of Takada et al., Genome Biology 8:215 (2007). This example is for integrins involved in cell-ECM and cell-cell adhesion. Many other adhesion molecules have been described with properties related to physiologic control and response (see Table 14 below).

TABLE 14

| Ligand-binding specificities of human integrins Integrins | ECM and cell-cell Ligands |
| --- | --- |
| α1β1 | Laminin, collagen |
| α2β1 | Laminin, collagen, thrombospondin, E-cadherin, tenascin |
| α3β1 | Laminin, thrombospondin, uPAR |
| α4β1 | Thrombospondin, MAdCAM-1, VCAM-1, fibronectin, osteopontin, ADAM, ICAM-4 |
| α5β1 | Fibronectin, osteopontin, fibrillin, thrombospondin, ADAM, COMP, L1 |
| α6β1 | Laminin, thrombospondin, ADAM, Cyr61 |
| α7β1 | Laminin |
| α8β1 | Tenascin, fibronectin, osteopontin, vitronectin, LAP-TGF-β, nephronectin, |
| α9β1 | Tenascin, VCAM-1, osteopontin, uPAR, plasmin, angiostatin, ADAM [25], VEGF-C, VEGF-D[26] |
| α10β1 | Laminin, collagen |
| α11β1 | Collagen |
| αvβ1 | LAP-TGF-β, fibronectin, osteopontin, L1 |
| αLβ2 | ICAM, ICAM-4 |
| αMβ2 | ICAM, iC3b, factor X, fibrinogen, ICAM-4, heparin |
| αXβ2 | ICAM, iC3b, fibrinogen, ICAM-4, heparin, collagen [27] |
| αDβ2 | ICAM, VCAM-1, fibrinogen, fibronectin, vitronectin, Cyr61, plasminogen |
| αIIbβ3 | Fibrinogen, thrombospondin, , fibronectin, vitronectin, vWF, Cyr61, ICAM-4, L1, CD40 ligand [28] |
| αVβ3 | Fibrinogen, vitronectin, vWF, thrombospondin, fibrillin, tenascin, PECAM-1, fibronectin, osteopontin, BSP, MFG-E8, ADAM-15, COMP, Cyr61, ICAM-4, MMP, FGF-2 [29], uPA [30], uPAR [31], L1, angiostatin [32], plasmin [33], cardiotoxin [34], LAP-TGF-β, Del-1 |
| α6β4 | Laminin |
| αVβ5 | Osteopontin, BSP, vitronectin, CCN3 [35], LAP-TGF-β |
| αVβ6 | LAP-TGF-β, fibronectin, osteopontin, ADAM |
| α4β7 | MAdCAM-1, VCAM-1, fibronectin, osteopontin |
| αEβ7 | E-cadherin |
| αVβ8 | LAP-TGF-β |

Additional coatings may include antibodies or other proteins known to have affinity for patient cell surface proteins so as to bring the patient cells into close proximity to the biosensor for the purpose of performing the methods described herein. It may also be beneficial to confirm that the patient cells are attached in the desired manner to the microplate. Specific biosensor coatings can additionally be used to enhance, improve, clarify, segregate, or detect specific cell signals from specific patient cell types and cell signaling responses to activation and therapeutics by linking the sensor coating to specific cellular pathways (see, e.g., Hynes, Integrins, Cell, 110:673-687 (2002)). A biosensor comprises an area to seed cells. For example, a biosensor can comprise a microtiter plate containing wells to seed cells. One or more cell samples can be seeded on a biosensor by physical adsorption to a surface in a distinct location. A biosensor can comprise 1, 10, 24, 48, 96, 384, or more distinct locations. A cell sample can comprise about 100 to about 100,000 individual cells or any cell number in between. An optimal cell sample depends on the size and nature of a distinct location on a biosensor. A cell sample can comprise about 5000 cells or less; about 10,000 cells or less; about 15,000 cells or less; about 20,000 cells or less; about 25,000 cells or less; or about 50,000 cells or less. A cell sample can comprise about 1000 to about 2500 cells; about 1000 to about 5000 cells; 5000 to about 10,000 cells; about 5000 to about 15,000 cells; about 5000 to about 25,000 cells; about 1000 to about 10,000 cells; about 1000 to about 50,000 cells; and about 5000 to about 50,000 cells. In certain embodiments, a change in a cellular response or physiological parameter is measured over a defined period of time. In other embodiments, the defined period of time is the amount of time that it takes for the control cells to reach a steady state in which a change in the output of the physiological parameter varies by 20% or less. In other embodiments, the change is observed in cells in 1 hour or less. In other embodiments, the change is observed in cells for at least 1 min. to about 60 min. and every minute in between. In other embodiments, the change in cell response is measured from about 10 minutes to about one week or 200 hours. In other embodiments, when a therapeutic agent is targeted to a cellular pathway, the cellular response is measured from about 10 minutes to about 5 hours, about 10 minutes to about 4 hours, about 10 minutes to about 3 hours, about 10 minutes to about 2 hours, about 10 minutes to about 1 hour, or about 10 minutes to about 30 minutes or any time point in between. In other embodiments, when a therapeutic agent affects cell proliferation or cell killing or cellular resistance, the cellular response is measured from about 1 hour to about 200 hours. In yet other embodiments, a combination of responses (otherwise described as a full temporal pattern) between 1 minute and 200 hours is used to determine therapeutic effect of a compound on cells and the cells ability to develop resistance. This timeframe encompasses the important process of short-term pathway signaling, dynamic reprogramming and longer term cellular responses important in assessing a probable response and maintenance thereof in a patient.

Once cells of a particular subject have been seeded on a biosensor, baseline measurements can be determined. Baseline measurements can be taken on the same cell sample, or a control cell sample. The control sample can comprise healthy cells or diseased cells from the same patient and/or same tissue. The control sample can comprise diseased cells that do not receive activator or agent. A control sample can comprise disease cells known to respond to the agent. In other embodiments, the control sample comprises disease cells known not to respond to the agent. The control sample may include application of an activator agent to healthy or diseased cells of a particular patient, designed to elicit a standardized response relating to cell health, cell metabolism, or cell pathway activity.

The control would be determined for each disease and/or drug type. In one embodiment, this involves a comparison against a healthy cell control from the same patient or comparison against a result for a pool of non-diseased patients (e.g. a normal reference range). For example, with cell killing drugs, the method will show benefit of killing disease cells over healthy cells to achieve a significant therapeutic index. Other embodiments include the use of pathway tools to determine pathway function and control by the drug. For targeted therapeutics, the tools can be activator agents (e.g., activator agents), bioreagents or small molecules which are used as controls to perturb a pathway and determine a targeted drug's ability to disrupt the activation. In yet other embodiments, the physiologic effect of a drug on a cell is measured without exogenous perturbation by an activator agent noting, for example, the temporal pattern or rate of oxygen consumption, the rate or temporal pattern of acidification, ion flux, or metabolite turnover.

In a particular embodiment, the biosensor signal is measured over a continuous time course. There are distinctive patterns on the time vs. biosensor signal plot that are indicative of a patient cell response to drug treatment. Evaluation of these patterns is useful to identify the presence of an efficacious event. A time course or constantly changing measurement of live and fully functional cells is more beneficial than the current practice used in typical whole cell assays that only represent a point in time. The methods described herein measure dynamic systems as they would occur in a patient and represent the most accurate means of determining patient response. In the case of pathway responses, recording of a complete time course or temporal pattern is superior in ability to support more complex analysis and obviates selecting the optimum time point for a single measurement.

Comparison against controls could occur at a temporal maxima, minima, or as differences between maximal signal-minimal signal, or by comparing integrated areas under a curve (AUC) for a time course plot or other non-linear comparisons (e.g. summation of difference vectors) of the test well against positive or negative control wells or comparisons of perturbed and unperturbed wells for the same patient viable diseased cells. Additional analyses supported only by measuring with a biosensor are time to reach maxima/minima, and other derivatives of the temporal time course. In the case of longer term responses, the time of comparison may be of a specific time point after a few days or a week of treatment or multiple applications of drug. The longer time course may also compare changes in slope or compare second derivatives of the time versus biosensor signal plot at the beginning, middle or end of a week of drug treatment. Significant changes compared to control may include absolute drop in biosensor signal related to curtailment of cellular metabolism. Alternatively, the drop may be followed by an increase that could indicate development of resistance to the drug during the assay. Additionally, non-linear Euclidean analyses could be used to produce a measure of total differences between controls and patient samples over a complete time-course. This too would be significant with respect to predicting the outcome for a patient.

In certain embodiments, the output of a biosensor over a defined period of time is represented as a cell index. The cell index is the change in impedance from a test starting point. Cell Index is defined as a measurement of impedance and can be applied in one instance of the present invention by measuring at a fixed electrical frequency of, for example, 10 kHz and fixed voltage.

And calculated by the equation $\text{Cell Index}_i = (R_{tn} - R_{t0})/F$

Where:

i=1, 2, or 3 time point.

F=15 ohm in one example when the instrument is operated at 10 kHz frequency $R_{t0}$ is the background resistance measured at time point T0.

$R_{tn}$ is the resistance measured at a time point Tn following cell addition, cell physiologic change, or cell perturbation.

Cell index is a dimensionless parameter derived as a relative change in measured electrical impedance to represent cell status. When cells are not present or are not well-adhered on the electrodes, the CI is zero. Under the same physiological conditions, when more cells are attached on the electrodes, the CI values are larger. CI is therefore a quantitative measure of cell number present in a well. Additionally, change in a cell physiological status, including cell morphology, changes in basal, stable, or quiescent condition, cell adhesion, or cell viability will lead to a changes in CI.

The cell index is a quantitative measure of the presence, density, attachment or changes thereof based upon a starting point or baseline impedance measurement. The baseline starting point impedance is a physical observable characteristic and an indication of the health, viability, and physiologic status of a cell prior to any treatment with drug or other activator. The baseline starting point can be used as a qualitative control for the CELx test. Addition of drug or activator causes the impedance to change in temporal patterns reflective of the specificity of the cellular physiologic change experienced by the cell. Changes in a cell physiological status, for example cell morphology, cell number, cell density, cell adhesion, or cell viability will lead to a change in the cell index.

Physiologic response parameters can additionally include cell cycle analysis and can be measured using any number of chemical biosensors such as fluorescent dyes conjugated or unconjugated or other colorimetric changes in patient cells associated with functional and dysfunctional pathways. For example changes in cell cycle for a population of cells using an unconjugated dye can be quantified with propidium iodide or similar dyes known to intercalate into DNA and correlate with cell cycling through G0, G1, S, G2, Gm phases of growth and replication by assessing changes in the amount of DNA. With one dye type, propidium iodide, the fluorescence of cells in the G2/M phase will be twice as high as that of cells in the G0/G1 phase. Propidium iodide can also intercalate into RNA and often ribonucleases are used to differentiate fluorescence signal from DNA compared to RNA. Examples also include dyes specific for particular proteins linked to cell cycle check points and provide additional cell cycle status measurement. Common instruments useful for performing these measurements but not limited to those listed here are fluorescence microscopy, confocal laser scanning microscopy, flow cytometry, fluorometry, fluorescence polarization, homogenous time resolved fluorescence, and fluorescence activated cell sorting (FACS).

Unconjugated dyes can be utilized with the present invention as a chemical biosensor of physiologic status of a cell or pathway while measuring metabolic parameters such as anabolism, catabolism, small molecule synthesis and generation, turnover, and respiration. A well-known cell physiologic response, named the Warburg Effect, describes the shift from oxidative phosphorylation to lactate production for energy generation in tumor and other diseased cells, and key signaling pathways, oncogenes and tumor suppressors (for example but not limited to Akt, mTor, c-myc, p53) can be measured by any of the chemical biosensor methods described here or by opto-electronic biosensors. Cellular oxygen consumption or respiration and glycolysis in cellular responses produces protons and causes rapid, easily measurable changes to the concentrations of dissolved oxygen and free protons or acidity.

An additional but not limiting example of a physiologic response parameter utilizing a chemical biosensor is the amount of ATP being utilized by cells in culture based on quantitation of the ATP present (Ex. CellTiterGlo and similar luciferase driven assays), an indicator of metabolically active and inactive cellular function.

Calcium, magnesium, and other charged ions that are important for biomolecular folding and function are in flux due to physiologic response. These too can be measured by chemical biosensors such as Cal-520, Oregon Green BAPTA-1, fura-2, indo-1, fluo-3, fluo-4, Calcium Green-1, and other EGTA or EDTA-like chemistries for specific ion complexation and measurement. These physiologic response parameters can be measured using many types of unconjugated reactive or binding dyes or other electronic or spectroscopic means. Many of these methods can be arranged so as to be non-destructive to the cells allowing the physiologic function of the same cell population to be continuously measured repeatedly over time.

Conjugated dyes such as those attached to natural cell protein binding ligands or attached to immunoparticles (antibodies or fragments of antibodies or high specificity high affinity synthetic molecules such as aptamers), or nucleic acid polymer hybridization probes can be used to measure physiologic response parameters related to proteins, specific pathway member molecules, DNA and or RNA in various cellular compartments, genomics, and proteomics, and are able to measure specific post-translational modifications and mechanisms. The post-translational modification and epigenetic means of cellular control can involve regulation by a multitude of enzymes performing pathway functions that include but are not limited to ribozymes, kinases, phosphatases, ubiquitinases, deubiquitinases, methylases, demethylases, and proteases. Examples of these molecules used for staining formalin fixed paraffin mounted samples of dead cells can be found in the DAKO Immunohistochemical Staining Methods Education Guide—Sixth Edition or at Cell Signaling Technology tutorials and application guides. These two examples may be even more useful with the present invention for measuring live cell response. Common instruments useful for performing this measurement but not limited to these methods are fluorescence microscopy, confocal laser scanning microscopy, flow cytometry, fluorometry, homogenous time resolved fluorescence, fluorescence polarization, and fluorescence activated cell sorting (FACS).

Combinations of conjugated and non-conjugated dyes can also be employed by the present invention to measure physiologic response of cells. Following activation, one type of receptor responsible for controlling physiologic response are GPCRs. They transmit information and control cells via two signaling pathways: changes in the level of secondary messenger cAMP, or changes in the level of intracellular Ca2+, which is liberated by secondary messenger inositol (1,4,5) triphosphate (IP3). cAMP detection for example can be based on a competitive immunoassay using cryptate-labeled anti-cAMP antibody (or other immunocapture molecule) and d2-labeled cAMP that competes with cellular cAMP for the GPCR reaction and subsequent antibody binding. The specific signal (i.e. energy transfer) is inversely proportional to the concentration of cAMP in the standard or sample.

Measurement of physiologic response by quantifying mRNA, RNAi, microRNAs and other RNA with physiologic function can be a very sensitive method employed with the practice of the present invention for determining activation of a cellular change at the transcription level. RNA can be quantified for example but not limited to these listed here by using rtPCR, qPCR, selective sequence probing, selective sequence capture, and sequence hybridization methods that all employ chemical sensors.

Immuno-capture and hybridization methods include those using bead based methods such as Luminex or fiber optic tip technologies such as Illumina or protein, DNA, RNA, or other hybridization microarray technologies where the specific capture reagent is immobilized onto a solid surface that is used to fish out, isolate, and accurately measure the physiologic response molecule(s) from the cells. These methods offer the benefit of measuring a multitude of response parameters in a single experiment.

A change in a cellular response or physiological parameter is determined by comparison to a baseline measurement. The change in cellular parameter or physiological response depends on the type of CReMS. For example, if the change in cellular response is determined optically, physically observable changes could be measured for example as a function of optical density at spectral wavelengths for chemical absorbance or transmittance, changes in a surface plasmon measurement device, or changes detected by photonic crystal devices. If the change in cellular parameter or physiological response is determined electrically, physically observable changes could be measured for example using milli or micro impedance changes of cells adhered to electrodes. Changes in pH, glucose, carbon dioxide, or ions, could be measured electronically using ion selective field effect transistors (ISFET).

In other embodiments, a rate of change is determined by a method measuring a CReMS response for a period of time required to determine a difference in cellular physiologic response to a therapeutic. The rate of change is described by various interpretation of the time course data and can be expressed as a rate or further derivative function of the rate including acceleration of the rate.

Tests that measure a physiological condition of a patient can derive one or more cutoff values above which and below which the patient is predicted to experience different clinical outcomes. In embodiments, one or more cutoff values for determining a change in cellular response is determined by a method comprising: determining a standard deviation, a signal to noise ratio, a standard error, analysis of variance, or other statistical test values known by those practiced in the art for determining appropriate confidence intervals for statistical significance of a set of samples from known responding cell samples and from a set of samples from known nonresponding patients; and determining the difference between the two and setting the cutoff value between the confidence intervals for both groups. An additional embodiment utilizes a cutoff determined from a normal reference range defined by CReMS response from patients known not to be diseased. In this embodiment, a single patient disease material test result is reported by comparing perturbed and unperturbed viable cancer cell results as described further elsewhere in the present invention to the non-diseased reference range interval.

A normal (healthy) reference range test result establishes what "normal" pathway activity is by conducting a study using normal tissue from healthy subjects. The test result then assesses whether any patients who are not expected to have the diseased pathway (e.g. biomarker negative patients) do in fact have abnormal pathway activity when compared to the values derived from the normal reference interval study. Results of the present invention are also compared for the abnormal measurements observed from biomarker-negative patients against the measurements made from those subjects who are currently diagnosed with the disease (biomarker positive patients) to see if the patients who are biomarker negative have pathway activity that is both abnormal and comparable to the pathway activity of biomarker positive patients. Those patients who have abnormal pathway activity that is comparable to the pathway activity of patients currently receiving and benefiting from therapies intended to disrupt the pathway activity would thus be diagnosed as having the pathway disease and should thus be treated with the drug that targets the biomarker in order to disrupt the pathway activity.

The present invention thus enables physicians to create more precise means of diagnosing a disease based on the functional activity of a diseased pathway. This is in contrast to the approach taken with when a single biomarker is measured that relies on a correlative, not a causative model. Current biomarker approaches can result in a high percentage of false negative and false positive results. The present invention will reduce the percentage of false results.

Preferred embodiments include 80-90% confidence intervals, more preferred embodiments include >90% confidence intervals and most preferred embodiments include >95% or >99% confidence intervals.

In embodiments, a cutoff value is validated by determining the status of blinded known samples as responders or non-responders using a cutoff value and unblinding the sample and determining the accuracy of predicting the status of the sample. In the case of a single cutoff value, output values that fall below the cutoff value or are closer to the output values for the known responders indicate the patient sample is exhibiting responsiveness to the therapeutic agent. If the output values are at or above the cutoff output value or are closer to the output values for the known non-responders output value, the cell sample is identified as a non-responder to the therapeutic agent. In some embodiments an output value of the biosensor at a defined period of time is classified as no response, weakly responsive or responsive.

In preferred embodiments, a cutoff value is validated by determining the status of blinded known samples as having the disease pathway response (e.g. cancer patients with abnormal EGF signaling) or not having the disease pathway response (e.g. cancer patients with normal EGF signaling) using a cutoff value and unblinding the samples and determining the accuracy of predicting the status of the sample. In the case of a single cutoff value, output values that fall below the cutoff value or are closer to the output values of the samples not having the disease pathway response indicate the patient sample is exhibiting no pathway disease. If the output values are at or above the cutoff value or are closer to the output values for the known diseased pathway samples values, the cell sample is identified as diseased pathway present. In some embodiments an output value of the biosensor at a defined period of time is classified as pathway disease not present, pathway disease inconclusive, or pathway disease present.

An output value at a defined period of time is selected in order to classify the output into the categories. In other embodiments, the defined period of time is the end point of the time period for which the cells have been continuously monitored in the biosensor. In other embodiments, the time period is at least 60 minutes, 240 minutes, 300 minutes, 10 hours, 24 hours, 60 hours, or 120 hours. In preferred embodiments the output at a defined period of time is between 30 minutes and 10 hours. In more preferred embodiments, the output at a defined period of time is between 180 minutes and 600 minutes or is 240 minutes.

In other embodiments, the cancer cells of a randomly selected population of cancer patients are tested using the methods described herein. It is expected that the cancer cells obtained from a population of cancer patients will exhibit a wide range of signaling activity levels or output values. To characterize the population distribution of signaling activity levels or output values, a finite mixture model analysis, or other statistical analysis of the individual output values using statistical analysis software (e.g. mixtools, an R package for analyzing finite mixture models) is performed. If two or more groups are identified within the population of cancer patients analyzed, a cut-off value between the mean output value of one group and the mean output value of the second or other groups is selected.

In embodiments, an output value classified as no response, is indicated by an output value that differs from the output value of the baseline prior to administration of a therapeutic agent or a control cell not treated with the therapeutic agent no more than at least 20% or less, 15% or less, 10% or less, or 5% or less.

In other embodiments, an output value classified as weakly responsive is indicated by an output value that differs from the output value of the baseline prior to administration of a therapeutic agent or a control cell not treated with the therapeutic agent of at least 50% or less and greater than 5%. In other embodiments, an output value percentage classified as responsive is indicated by an output value that differs from the baseline prior to administration of a therapeutic agent or a control cell not treated with the therapeutic agent of at least greater than 50%. In embodiments, the control sample is a sample of the disease cells from the same subject and not treated with the therapeutic agent.

A further aspect of the methods described herein involves developing an algorithm that can be used to predict the efficacy of a therapeutic agent in an individual subject. The algorithm incorporates the values derived using the methods described herein, in combination with values assigned to one or more patient characteristics that define an aspect of an individual subject's health. The patient characteristics can include, but are not limited to, the presence of metastases, the location of metastases, nodal status, disease free interval from initial diagnosis of cancer to diagnosis of metastases, receipt of adjuvant chemotherapy, receipt of other drug therapies, receipt of radiation therapy, dominant site of disease, tumor mass size, body-mass index, number of tender joints, number of swollen joints, pain, disability index, physician global assessment, patient global assessment, Bath Ankylosing Spondylitis Functional Index, Bath Ankylosing Spondylitis Disease Activity Index, Bath Ankylosing Spondylitis Metrology Index, C-Reactive Protein, total back pain, inflammation, genetic status, history of other illnesses, other vital health statistics status, and any combinations thereof. The algorithm that incorporates these values would weight these values according to their correlation to disease progression in a population of patients with the disease that the therapeutic agent is intended to treat. Disease characteristics that did not demonstrate any correlation with differential response would not be included in the algorithm.

In one embodiment, a numerical value representing the patient characteristics can be derived from a regression analysis of the test results (i.e., values derived from the methods of determining responsiveness to a therapeutic agent, an activator agent, a combination of a therapeutic agent(s) and an activator agent(s), etc. as described herein), the patient characteristics, and the clinical outcome of a group of patients studied. In one example, optimization of an algorithm using the test results in combination with variables based on patient characteristics data can be performed by dividing the test output values into 10 intervals based on 9 equally spaced cut-points of width 0.10 beginning with 0.10. For each cut-point, a Cox regression can be run using an indicator variable which takes on the value "one" if a subject has an algorithm value less than or equal to the cut-point and "zero" otherwise. The hazard ratio, being the comparison of those at or below the cut-off, versus those above the cut-off, will be determined for each cut-point. The value of the cut-point that minimizes the estimated hazard ratio is then selected.

For example, it may be found that when a patient's total tumor mass is above a certain value, their responsiveness to a drug, as determined by the methods described herein, will not be sufficient to prolong the patient's potential progression free period beyond the median result found for those patients not responsive to the drug. In the case when a test result indicates that the drug is functional in the patient, and that they would otherwise be expected to benefit from it, the algorithm including the patient characteristics variables would report that the result is indeterminate since the tumor mass variable offsets the test result value.

Another aspect of the methods described herein provides a method for determining a cut-off value for a test that identifies patients likely or unlikely to respond to a targeted therapeutic agent. This method involves a) selecting a group of patients, each of whom has the same disease and is prescribed the same therapeutic, b) using the methods described herein to derive a test value for each subject within a group of patients, c) observing the health status of each member of the group of patients tested over a period of time sufficient for a significant percentage of the total patients tested to reach a predefined clinical endpoint and record the length of time required for each of the patients to reach, if they did, the predefined clinical endpoint, d) identifying two or more candidate cut-off values that are equidistant in value to the other, wherein each candidate cut-off value represents a value below which a patient is predicted to respond or not respond and above which a patient is predicted to respond in opposite manner of those whose scores fell below the cut-off value, e) using a statistical method to analyze the difference between the clinical endpoint periods for patients whose test value was at or below the cut-off and the clinical endpoint periods for those patients whose test value was above the cut-off, and f) selecting the cut-off value that results in the greatest percentage of patients who are predicted not to respond to the therapy amongst the group of candidate cut-off values that indicates there is a statistically significant difference between the group of patients above and below the cut-off value.

Using the methods described herein, it is possible to derive a numeric test result value for an individual subject that can be compared to the test value derived from other individuals with the same disease whose cells were tested with the same therapeutic. This makes it possible to predict the efficacy of a therapeutic on an individual subject by: a) recording the test result values for a group individual subjects who have the same disease and were tested with the same therapeutic, b) compiling those values into a list, c) ordering the list on the basis of test results values for the individual subjects tested on the basis of each individual subject's absolute numeric test value, and d) determining the percentile rank of an individual subject's test value, wherein the percentile rank of an individual subject's test value is predictive of the efficacy of the therapeutic agent for the disease in the individual subject.

Another embodiment includes analyzing the results obtained from a clinical trial testing the efficacy of the same therapy to estimate the percentile ranking of a particular result and then identifying the percentile rank for an individual subject's test value, and identifying the clinical trial end point result that corresponds to the same percentile ranking, wherein the clinical trial end point result at the same percentile ranking as the individual subject's test value is predictive of the clinical result an individual subject is likely to obtain from the therapeutic agent for the disease. The clinical trial end points can include, for example, time-to-progression period, progression-free survival period, overall survival period, objective response period, ACR response, change in Total Sharp Score, erosion score, and Joint Space Narrowing, clinical response, pain, disability index, clinical remission, body-surface area involvement, physicians global assessment, and psoriasis area and severity index.

Another embodiment includes a method to determine the statistical correlation between the test result values derived from the methods described herein and the clinical outcome for an individual who received the therapeutic that was tested. This method comprises: a) selecting a group of patients, each of whom has the same disease and is prescribed the same therapeutic, b) using the methods described herein to derive a test result value for an individual, c) compiling a list of test result values for each subject within a group of patients who have the same disease and were tested with the same therapeutic, d) observing the health status of each member of the group of patients tested over a period of time sufficient for a significant percentage of the total patients tested to reach a predefined clinical endpoint, e) recording the length of time required for each of the patients to reach, if they did, the predefined clinical end-point, f) analyzing the end-point data (e.g. time-to-progression period, progression-free survival, ACR response) in such a manner that the statistical relationship between the end point result and the test value is determined.

By way of example, once the results from a clinical trial are available, the determination of an estimate of the cut-off value—"C*"—proceeds as follows. Assuming that a Cox regression test indicates that the test value is predictive of a patient outcome, such as time-to-progression (TTP), the test values will be divided into 10 intervals based on 9 equally spaced cut-points of width 0.10 beginning with 0.10. For each cut-point, a Cox regression will be run using an indicator variable which takes on the value "one" if a subject has an assay value less than or equal to the cut-point, and "zero" otherwise. The hazard ratio, being the comparison of those at or below the cut-off versus those above the cut-off, will be determined for each cut-point. The value of the cut-point that maximizes the estimated hazard ratio will be selected for use in the subsequent pivotal phase of the study. For the final analysis, a Cox proportional hazard regression can be run with an indicator variable (below the cut-point versus above the cut-point). The final analysis can also include other putative predictive patient characteristic variables of TTP.

When a therapeutic agent is a targeted therapeutic agent that binds to a cell surface receptor, the change in cellular responsiveness is measured in the absence or presence of an activator agent or perturbant that binds to the receptor. In embodiments, the therapeutic agent is administered to the cell sample before, at the same time or after the activator or perturbant. In embodiments, the activator agent or perturbant is label free. A therapeutic agent is selected that inhibits the cellular responsiveness to the activator agent or perturbant as compared to baseline measurement and optionally, as compared to other therapeutic agents, regardless of the density of the cell surface receptors. In some embodiments, a therapeutic agent is selected that inhibits the action of the activator agent or perturbant independent of the density of cell receptors.

The change in the physiological parameter can be an increase or a decrease in the parameter as compared to baseline or healthy or unperturbed cell control. The changes could represent full agonism, superagonism, irreversible agonism, selective agonism, co-agonism, inverse agonism, or partial limiting agonism, reversible and irreversible antagonism, competitive antagonism, non-competitive antagonism, un-competitive antagonism. The changes can occur sooner, later or not at all as compared to an appropriate control. The changes could be selected to occur for a longer or shorter period of time. Changes could be selected that are reversible or irreversible.

For example, a therapeutic agent that results in a decrease in cell signaling would be selected for treatment of an autoimmune condition. Peripheral blood cells that respond to an agent that inhibits the action of a cytokine show a decrease in cell signaling. In another example, for disease cells responsive to an anticancer agent, such as a humanized antibody targeted to a receptor like Her2, the disease cells would show a significant reduction in EGF family pathway signaling. In other cases, for disease cells responsive to an anti-angiogenic agent, the disease cells would show a reduction in VEGF pathway signaling or reduction in proliferative ability. The CReMS response or physically observable characteristic measured for each type of agent is dependent upon the intended physiological response the drug was designed to illicit and can be as specific or general as needed. The key is the use of the CReMS for physiological measurement of a live cell for a period of time to test the response the drug was intended to alter.

A particular therapeutic agent or agents can be administered to the diseased cells, and optionally, healthy cells to determine the effectiveness of the particular therapeutic or therapeutics. Diseased cells and/or healthy cells can also be untreated so as to compare the effect of the therapeutic or therapeutics on treated and untreated diseased and/or healthy cells. A single therapeutic can be administered to determine how a subject will respond to the therapeutic treatment. In another embodiment, a panel of different therapeutics can be administered to cells of a particular subject.

In certain embodiments, a cutoff value for efficacy of a therapeutic agent to inhibit activation of a cellular pathway is determined in one embodiment by adding the drug and measuring the physiologic response. In another embodiment, the pathway is perturbed with and without drug pre-treatment. Changes to the physiologic baseline signal or reductions of the activation signal by the drug at the 85% confidence interval or ideally greater than the 90% confidence interval or more ideally greater than the 95% or 99% confidence interval are deemed efficacious. In embodiments, a cutoff value for efficacy of a therapeutic agent that inhibits cell proliferation or enhances cell killing is determined by recording the physiologic response over time. Reductions to the physiologic baseline signal or deviation from the temporal pattern as compared to non-treated or healthy cells or a combination thereof by the drug at the 85% confidence interval or ideally greater than the 90% confidence interval or more ideally greater than the 95% or 99% confidence interval are deemed efficacious.

The sensitivity and specificity of the therapeutic agent for treating the disease of an individual subject is determined by comparing the cellular physiologic pathway response as measured by the CReMS to determine that the drug is working as it was designed on a specific target and determining that a cutoff value for efficacy has been attained.

In some embodiments, the activator agent and/or the therapeutic agent are titrated in order to obtain the Hill Slope, $EC_{50}$ or $IC_{50}$ value for either agent. The data obtained from the activating agent titration and/or the therapeutic agent titration may be used to assess the potency (what concentration achieves one half maximal effect) and or efficacy (maximum achievable effect) of either agent. A further aspect includes a method of predicting efficacy of a therapeutic agent in an individual subject using diseased cells obtained from the subject, by titrating an activator agent or a therapeutic agent in order to develop an IC50 value, where the activating agent reduces cellular pathway activity and the therapeutic agent agonizes cellular pathway activity.

In one embodiment, the method for determining therapeutic efficacy of an agent for a disease in an individual subject comprises: administering the agent to at least one isolated disease cell sample from the individual subject in a cellular response measurement system (CReMS); and determining whether a change in a cellular response parameter of the cell sample to the agent occurs as compared to a baseline measurement, wherein the change in cellular response indicates that the agent has therapeutic efficacy for the disease in the individual subject. In embodiments, a method further comprises administering to at least one isolated disease cell sample from the individual subject in a cellular response measurement system an activator agent or perturbant that perturbs the cellular response pathway before or after administering the therapeutic agent.

The test can measure the effectiveness of a drug in a range of concentrations from below 1 nM to greater than 100 uM generally with less than 20% standard deviation and optimally with less than 5% standard deviation. The compound test range will correspond to dosing levels as defined on a drug packaging label known as the maximum tolerated dose. Unlike most tests that cannot ascertain the number of live cells in the actual set of cells in the test, this test is only working with the live cells as determined in a quality control and baseline physiologic determination step at the beginning of the test. The result of this feature reduces the variance of the test result. The test can be conducted using a temperature, oxygen, humidity, and carbon dioxide range generally acceptable for cell viability commonly known to those practiced in the art. In some cases, a preferred temperature range is between 25° C.-40° C. In other cases the temperature may be optimized further to ±0.5° C. within this range for specific perturbations and maintained using standard temperature controlled incubator cabinets.

Methods of the invention include administering candidate therapeutics to a subject's cells to determine safety and to determine therapeutic effectiveness. Additionally, administration of a candidate therapeutic to a subject's diseased cells may be used as a method of selecting the proper patient population for a phase II or III clinical trial. Methods of the invention include testing diseased cells against known therapeutic combinations. Additionally, methods of the invention include testing known and candidate therapeutics.

Methods of the invention also including administering combinations of therapeutic agents to determine if a particular combination of agents produces a more effective result (i.e., amelioration or cure of disease symptoms). A combination of therapeutic agents is two or more therapeutic agents administered to the same cell sample. In an embodiment of the invention, the combination of therapeutic agents is administered to a cell sample concurrently. In an embodiment, at least one therapeutic agent is administered to the cell sample at a time different than the administration of the other at least one therapeutic agent of the combination.

After administration of therapeutic agents to a cell sample, real time data can be collected on multiple aspects of the cell sample. For instance, pH and temperature can be measured. Additionally, other factors, such as "cell death factors", can be determined. A cell death factor as determined by a CReMS can be a change in a physicochemical property as measured by the CReMS. For instance, cancer cells will attach to a surface and provide a baseline reading for a refractive index. Administration of a therapeutic agent that promotes cancer cell death would cause a change in the refractive index since the cancer cells in a sample would round up and detach from a surface. This could be measured by an optical biosensor utilizing surface plasmon resonance in a continuous real-time manner.

In certain embodiments, the methods involve determining an optimal dose range for a particular therapeutic. Determination of a dose range allows for proper design of clinical trials and/or allows the physician to balance efficacy with detrimental side effects. In embodiments, a method comprises administering a range of doses of a therapeutic agent to separate samples of diseased cells from the same patient, and determining the dose range that results in a change in a physiological parameter of the cells as described herein as compared to baseline and/or healthy control cells.

Once any of the methods described herein are used to determine whether an individual subject's disease cells respond to one or more therapeutic agents, the results are communicated to a health care worker to allow for selection of a therapeutic agent for treatment of the subject. In embodiments, the methods further comprise administering the selected therapeutic agent to the subject.

Measuring the signaling pathway activity can detect the presence of abnormalities consistent with the disease. To accomplish this, a platform has been developed that leverages the intimate connection between cellular signaling pathway operation and cell adhesion processes. Interaction of transmembrane cell adhesion receptors, such as integrins, cadherins, Ig CAMs, and selectins, with their cognate binding sites in the extracellular matrix or on other cells, has demonstrated connection to multiple cellular signaling processes. The adhesion connections communicate through organized membrane-proximal cyto skeletal structures that are directly linked to intracellular signaling cascades. This makes it possible to affect specific adhesion molecules via specific cellular pathways upon application of pathway activators.

To measure how activation of a cellular pathway effects cell adhesion, a device is used that measures complex impedance changes of viable patient cells attached to specific extracellular matrix (ECM) materials coating a microelectrode. Known as cellular impedance biosensors, these devices are comprised of a standard microplate with thin gold electrodes covering the bottom of each well. Wells employed with a selective extracellular matrix attach viable cells in a specific manner to the microplate well electrodes. The presence of viable cells on top of the well electrodes affects the local ionic environment at the electrode/cell interface, leading to an increase in electrode impedance. When cells are perturbed or stimulated to change their function, the accompanying changes in cell adhesion thus alter the impedance. Specificity of the adhesion response can be determined by the application of specific ECM or tool compounds or drugs known to act at various points in the pathway. Impedance results are further supported by immunodetection of specific proteome changes at time points indicated by the impedance temporal pattern. Systems are capable of detecting adhesion changes in the sub-nanometer to micrometer range and generate data for categorizing various pathway pharmacologies on live cells. The amount of impedance measured, referred to as a cell attachment signal (CAS), expressed in ohms, can be used to monitor cell viability, adhesion, and signaling pathway activation. Data generated is impedance versus time.

Therefore, in a diagnostic test of the invention, the analyte is the cell attachment signal (CAS) that viable patient cells generate, alone or in the presence of cell activators, when placed in the well of a microplate and analyzed with a biosensor such as an impedance biosensor. For every test, the CAS is measured and analyzed for two groups of patient cell samples.

1) Patient cells only (C)
2) Patient cells+activator pathway factor(s) (CF)
3) Patient cells+activator pathway factor(s)+confirming agent (CCF)

To detect whether the signaling pathway is functioning normally or abnormally, the signaling pathway in a patient's diseased cells are perturbed with one or more pathway factors and a confirming agent and the resulting activity is compared to the effect the activator and/or the confirming agent has on a cut-off value. The cut-off value can be derived from a study involving analysis of the signaling pathway activity of a sample set of healthy cells obtained from subjects who do not have cancer. The assay measurand reflects the change in CAS between the CF and C cells in a patient's diseased cells and the change in CAS between the CF and CCF diseased cells. If the signaling pathways are abnormal, the CAS change between the CF and C diseased cells and/or the CAS change between the CF and CCF diseased cells will be above a cut-off value. The cut-off value is typically above the upper limit of the normal reference interval for the pathway activity of interest. In a simplified embodiment, the measurement of the CAS of the CF and CCF samples after the point of activation compared to the CAS at the point in time immediately before activation with the pathway factor or confirming agent may also be a useful measurand.

The diagnostic assays of the invention can be used in essentially any clinical situation, in particular those in which currently a genetic or protein biomarker is used as an indicator of disease and thus as an indicator for therapeutic decision-making. Table 15 below shows a list of FDA approved therapeutic agents together with the biomarkers associated with their use in treatment of various disease conditions. In accordance with the methods of the invention, the approach described herein can be used to examine the activity of the signaling pathway involved that is affected by the therapeutic agent to thereby determine whether treatment with that therapeutic agent should be prescribed to a patient, regardless of whether they exhibit a positive result using the standard biomarker assay.

TABLE 15

Pharmacogenomic Biomarkers in Drug Labeling

| HUGO Symbol | Referenced Subgroup | Therapeutic Area | Drug |
|---|---|---|---|
| ALK | ALK gene rearrangement positive | Oncology | Crizotinib |
| BCR-ABL T315I | BCR-ABL T315I mutation | Oncology | Ponatinib |
| BCR/ABL1 | Philadelphia chromosome (t(9;22)) positive | Oncology | Bosutinib |
| BCR/ABL1 | Philadelphia chromosome (t(9;22)) positive; T315I mutation-positive | Oncology | Dasatinib |
| BCR/ABL1 | Philadelphia chromosome (t(9;22)) positive | Oncology | Imatinib |
| BCR/ABL1 | Philadelphia chromosome (t(9:22)) positive | Oncology | Nilotinib |
| BCR/ABL1 | BCR-ABL T315I | Oncology | Omacetaxine |
| BRAF | BRAF V600E mutation positive | Oncology | Dabrafenib |
| BRAF | BRAF V600E/K mutation positive | Oncology | Trametinib |
| BRAF | BRAF V600E mutation positive | Oncology | Vemurafenib |
| CCR5 | CCR5 positive | Infectious Diseases | Maraviroc |
| CFTR | CFTR G551D, G1244E, G1349D, G178R, G551S, S1251N, S1255P, S549N, or S549R mutation carriers | Pulmonary | Ivacaftor |
| CYB5R1-4 | NADH cytochrome b5 reductase deficient | Gastroenterology | Metoclopramide |
| CYP1A2 | CYP1A2 genotypes | Gastroenterology | Dexlansoprazole |
| CYP2C19 | CYP2C19 poor metabolizers | Rheumatology | Carisoprodol |
| CYP2C19 | CYP2C19 poor metabolizers | Psychiatry | Citalopram |
| CYP2C19 | CYP2C19 poor metabolizers | Neurology | Clobazam |
| CYP2C19 | CYP2C19 intermediate or poor metabolizers | Cardiology | Clopidogrel |
| CYP2C19 | CYP2C19 poor metabolizers | Gastroenterology | Dexlansoprazole |
| CYP2C19 | CYP2C19 poor metabolizers | Psychiatry | Diazepam |
| CYP2C19 | CYP2C19 poor metabolizers | Neurology | Drospirenone and Ethinyl Estradiol |
| CYP2C19 | CYP2C19 poor metabolizers | Gastroenterology | Esomeprazole |
| CYP2C19 | CYP2C19 poor metabolizers | Gastroenterology | Lansoprazole |
| CYP2C19 | CYP2C19 poor metabolizers | Gastroenterology | Omeprazole |
| CYP2C19 | CYP2C19 poor metabolizers | Gastroenterology | Pantoprazole |
| CYP2C19 | CYP2C19 poor metabolizers | Cardiology | Prasugrel |
| CYP2C19 | CYP2C19 poor metabolizers | Gastroenterology | Rabeprazole |
| CYP2C19 | CYP2C19 poor metabolizers | Cardiology | Ticagrelor |
| CYP2C19 | CYP219 intermediate or poor metabolizers | Infectious Diseases | Voriconazole |

TABLE 15-continued

Pharmacogenomic Biomarkers in Drug Labeling

| HUGO Symbol | Referenced Subgroup | Therapeutic Area | Drug |
|---|---|---|---|
| CYP2C9 | CYP2C9 poor metabolizers | Rheumatology | Celecoxib |
| CYP2C9 | CYP2C9 poor metabolizers | Rheumatology | Flurbiprofen |
| CYP2C9 | CYP2C9 intermediate or poor metabolizers | Cardiology or Hematology | Warfarin |
| CYP2D6 | CYP2D6 poor metabolizers | Psychiatry | Amitriptyline |
| CYP2D6 | CYP2D6 poor metabolizers | Psychiatry | Aripiprazole |
| CYP2D6 | CYP2D6 poor metabolizers | Psychiatry | Atomoxetine |
| CYP2D6 | CYP2D6 poor metabolizers | Cardiology | Carvedilol |
| CYP2D6 | CYP2D6 poor metabolizers | Dental | Cevimeline |
| CYP2D6 | CYP2D6 poor metabolizers | Psychiatry | Citalopram |
| CYP2D6 | CYP2D6 poor metabolizers | Psychiatry | Clomipramine |
| CYP2D6 | CYP2D6 poor metabolizers | Psychiatry | Clozapine |
| CYP2D6 | CYP2D6 ultra-rapid metabolizers | Anesthesiology | Codeine |
| CYP2D6 | CYP2D6 poor metabolizers | Psychiatry | Desipramine |
| CYP2D6 | CYP2D6 poor metabolizers | Neurology | Dextromethorphan and Quinidine |
| CYP2D6 | CYP2D6 poor metabolizers | Psychiatry | Doxepin |
| CYP2D6 | CYP2D6 poor metabolizers | Psychiatry | Fluoxetine |
| CYP2D6 | CYP2D6 poor metabolizers | Psychiatry | Fluvoxamine |
| CYP2D6 | CYP2D6 poor metabolizers | Neurology | Galantamine |
| CYP2D6 | CYP2D6 poor metabolizers | Psychiatry | Iloperidone |
| CYP2D6 | CYP2D6 poor metabolizers | Psychiatry | Imipramine |
| CYP2D6 | CYP2D6 poor metabolizers | Cardiology | Metoprolol |
| CYP2D6 | CYP2D6 poor metabolizers | Psychiatry | Modafinil |
| CYP2D6 | CYP2D6 poor metabolizers | Psychiatry | Nefazodone |
| CYP2D6 | CYP2D6 poor metabolizers | Psychiatry | Nortriptyline |
| CYP2D6 | CYP2D6 poor metabolizers | Psychiatry | Paroxetine |
| CYP2D6 | CYP2D6 poor metabolizers | Psychiatry | Perphenazine |
| CYP2D6 | CYP2D6 poor metabolizers | Psychiatry | Pimozide |
| CYP2D6 | CYP2D6 poor metabolizers | Cardiology | Propafenone |
| CYP2D6 | CYP2D6 poor metabolizers | Cardiology | Propranolol |
| CYP2D6 | CYP2D6 poor metabolizers | Psychiatry | Protriptyline |
| CYP2D6 | CYP2D6 poor metabolizers | Cardiology | Quinidine |
| CYP2D6 | CYP2D6 poor metabolizers | Psychiatry | Risperidone |
| CYP2D6 | CYP2D6 poor metabolizers | Infectious Diseases | Terbinafine |
| CYP2D6 | CYP2D6 poor metabolizers | Neurology | Tetrabenazine |
| CYP2D6 | CYP2D6 poor metabolizers | Psychiatry | Thioridazine |
| CYP2D6 | CYP2D6 poor metabolizers | Genitourinary | Tolterodine |
| CYP2D6 | CYP2D6 poor metabolizers | Analgesic | Tramadol |
| CYP2D6 | CYP2D6 poor metabolizers | Psychiatry | Trimipramine |
| CYP2D6 | CYP2D6 poor metabolizers | Psychiatry | Venlafaxine |
| CYP2D6 | CYP2D6 poor metabolizers | Neurology | Vortioxetine |
| del (5q) | Chromosome 5q deletion | Hematology | Lenalidomide |
| DPYD | DPD deficient | Oncology | Capecitabine |
| DPYD | DPD deficient | Dermatology | Fluorouracil |
| DPYD | DPD deficient | Oncology | Fluorouracil |
| EGFR | EGFR exon 19 deletion or exon 21 substitution (L858R) mutation positive | Oncology | Afatinib5 |
| EGFR | EGFR protein expression positive | Oncology | Cetuximab |
| EGFR | EGFR protein expression positive | Oncology | Erlotinib |
| EGFR | EGFR exon 19 deletion or exon 21 substitution (L858R) positive | Oncology | Erlotinib |
| EGFR | EGFR protein expression positive | Oncology | Panitumumab |
| ERBB2 | HER2 protein overexpression or gene amplification positive | Oncology | Ado-Trastuzumab Emtansine |
| ERBB2 | HER2 protein overexpression negative | Oncology | Everolimus |
| ERBB2 | HER2 protein overexpression positive | Oncology | Lapatinib |
| ERBB2 | HER2 protein overexpression positive | Oncology | Pertuzumab |
| ERBB2 | HER2 protein overexpression positive | Oncology | Trastuzumab |
| ESR1 | Estrogen receptor positive | Oncology | Everolimus |
| ESR1 | Estrogen receptor positive | Oncology | Exemestane |
| ESR1 | Estrogen receptor positive | Oncology | Fulvestrant |
| ESR1, PGR | Hormone receptor positive | Oncology | Anastrozole |
| ESR1, PGR | Hormone receptor positive | Oncology | Letrozole |
| ESR1, PGR | Hormone receptor positive | Oncology | Tamoxifen |
| F2 | Prothrombin mutation G20210A positive | Oncology | Tamoxifen |
| F5 | Factor V Leiden carriers | Hematology | Eltrombopag |
| F5 | Factor V Leiden carriers | Oncology | Tamoxifen |
| FIP1L1/PDGFRA | FIP1L1/PDGFRα fusion kinase (or CHIC2 deletion) positive | Oncology | Imatinib |

TABLE 15-continued

Pharmacogenomic Biomarkers in Drug Labeling

| HUGO Symbol | Referenced Subgroup | Therapeutic Area | Drug |
|---|---|---|---|
| G6PD | G6PD deficient | Infectious Diseases | Chloroquine |
| G6PD | G6PD deficient | Endocrinology | Chlorpropamide |
| G6PD | G6PD deficient | Oncology | Dabrafenib |
| G6PD | G6PD deficient | Dermatology | Dapsone |
| G6PD | G6PD deficient | Infectious Diseases | Dapsone |
| G6PD | G6PD deficient | Endocrinology | Glimepiride |
| G6PD | G6PD deficient | Endocrinology | Glipizide |
| G6PD | G6PD deficient | Endocrinology | Glyburide |
| G6PD | G6PD deficient | Infectious Diseases | Mafenide |
| G6PD | G6PD deficient | Hematology | Methylene Blue |
| G6PD | G6PD deficient | Infectious Diseases | Nalidixic Acid |
| G6PD | G6PD deficient | Infectious Diseases | Nitrofurantoin |
| G6PD | G6PD deficient | Gastroenterology | PEG-3350, Sodium Sulfate, Sodium Chloride, Potassium Chloride, Sodium Ascorbate, and Ascorbic Acid |
| G6PD | G6PD deficient | Rheumatology | Pegloticase |
| G6PD | G6PD deficient | Infectious Diseases | Primaquine |
| G6PD | G6PD deficient | Infectious Diseases | Quinine Sulfate |
| G6PD | G6PD deficient | Oncology | Rasburicase |
| G6PD | G6PD deficient | Antidotal Therapy | Sodium Nitrite |
| G6PD | G6PD deficient | Hematology | Succimer |
| G6PD | G6PD deficient | Infectious Diseases | Sulfamethoxazole and Trimethoprim |
| HLA-A | HLA-A*3101 allele carriers | Neurology | Carbamazepine |
| HLA-B | HLA-B*5701 allele carriers | Infectious Diseases | Abacavi |
| HLA-B | HLA-B*1502 allele carriers | Neurology | Carbamazepine |
| HLA-B | HLA-B*1502 allele carriers | Neurology | Phenytoin |
| HPRT1 | HGPRT deficient | Transplantation | Mycophenolic Acid |
| IFNL3 | IL28B rs12979860 T allele carriers | Infectious Diseases | Boceprevir |
| IFNL3 | IL28B rs12979860 T allele carriers | Infectious Diseases | Peginterferon alfa-2b |
| IFNL3 | IL28B rs12979860 T allele carriers | Infectious Diseases | Simeprevir |
| IFNL3 | IL28B rs12979860 T allele carriers | Infectious Diseases | Sofosbuvir |
| IFNL3 | IL28B rs12979860 T allele carriers | Infectious Diseases | Telaprevir |
| IL2RA | CD25 antigen positive | Oncology | Denileukin Diftitox |
| KIT | c-KIT D816V mutation negative | Oncology | Imatinib |
| KRAS | KRAS codon 12 and 13 mutation negative | Oncology | Cetuximab |
| KRAS | KRAS codon 12 and 13 mutation negative | Oncology | Panitumumab |
| LDLR | Homozygous familial hypercholesterolemia | Endocrinology | Atorvastatin |
| LDLR | Homozygous familial hypercholesterolemia | Endocrinology | Lomitapide |
| LDLR | Homozygous familial hypercholesterolemia | Endocrinology | Mipomersen |
| LDLR | Homozygous familial hypercholesterolemia | Endocrinology | Pravastatin |
| LDLR | Homozygous familial hypercholesterolemia | Endocrinology | Rosuvastati |
| MS4A1 | CD20 positive | Oncology | Ibritumomab Tiuxetan |
| MS4A1 | CD20 positive | Oncology | Obinutuzumab |
| MS4A1 | CD20 positive | Oncology | Ofatumumab |
| MS4A1 | CD20 positive | Oncology | Rituximab |
| MS4A1 | CD20 antigen positive | Oncology | Tositumomab |
| NAGS | N-acetylglutamate synthase deficient | Metabolic Disorders | Carglumic Acid |
| NAGS, CPS1, ASS1, OTC, ASL, ABL2 | Urea cycle enzyme deficient | Neurology | Valproic Acid |
| NAT1-2 | Slow acetylators | Cardiology | Isosorbide and Hydralazine |
| NAT1-2 | Slow inactivators | Infectious Diseases | Rifampin, Isoniazid, and Pyrazinamide |
| PDGFRB | PDGFR gene rearrangement positive | Oncology | Imatinib |
| Ph Chromosome | Ph Chromosome negative | Oncology | Busulfan |
| PML/RARA | PML/RARα (t(15;17)) gene expression positive | Oncology | Arsenic Trioxide |
| PML/RARA | PML/RARα (t(15;17)) gene expression positive | Oncology | Tretinoin |

TABLE 15-continued

Pharmacogenomic Biomarkers in Drug Labeling

| HUGO Symbol | Referenced Subgroup | Therapeutic Area | Drug |
|---|---|---|---|
| POLG | POLG mutation positive | Neurology | Valproic Acid |
| PROC | Protein C deficient | Cardiology or Hematology | Warfarin |
| SERPINC1 | Antithrombin III deficient | Hematology | Eltrombopag |
| T790M | EGFR mutation | Oncology | Osimertinib |
| TNFRSF8 | CD30 positive | Oncology | Brentuximab Vedotin |
| TPMT | TPMT intermediate or poor metabolizers | Rheumatology | Azathioprine |
| TPMT | TPMT intermediate or poor metabolizers | Oncology | Cisplatin |
| TPMT | TPMT intermediate or poor metabolizers | Oncology | Mercaptopurine |
| TPMT | TPMT poor metabolizers | Oncology | Thioguanine |
| UGT1A1 | UGT1A1*28 allele homozygotes | Pulmonary | Indacaterol |
| UGT1A1 | UGT1A1*28 allele carriers | Oncology | Irinotecan |
| UGT1A1 | UGT1A1*28 allele homozygotes | Oncology | Nilotinib |
| UGT1A1 | (TA)7/(TA)7 genotype (UGT1A1*28/*28) | Oncology | Pazopanib |
| VKORC1 | VKORC1 rs9923231 A allele carriers | Cardiology or Hematology | Warfarin |

Methods of analyzing the continuous measurements to determine whether a change in a physiological response parameter occurs in the cellular sample are described herein (e.g., magnitude of response (positive or negative), time to max or min, slope of time vs. magnitude at any point of the response timeline, etc.). These and other methods of non-linear analysis can be used to determine whether a change in a physiological response parameter occurs in the presence of an activator agent.

Baselines and controls can be used to adjudge the status of the cellular pathway. Suitable baselines can include, but are not limited to, a sample without the activator agent, a sample of infinite dilution of the activator agent, the same sample prior to or following sufficiently lengthy time after the addition of the activator agent, and other such baselining activities known to those skilled in the art of cell based assays.

Suitable controls can include, but are not limited to, a sample of healthy material from the same patient, a set of samples of healthy material from a sufficient number of patients lacking the disease of interest to derive a normal reference interval, a sample with a similar but different activating agent, a cell line of known positive or negative response, a sample treated with the inverse activity of the activating agent, a sample of diseased material from one or more patients, and other such positive and negative controls known to those practiced in the art of cell based assays.

K. Analysis and Interpretation of Test Results

The test results obtained using the methods described herein can be analyzed and interpreted in a variety of ways to provide information to a clinician and/or a patient. Certain embodiments are set forth as follows.

(i) Diseased Pathway Analysis. This analysis identifies whether diseased pathway activity is found in a patient ex vivo. The analysis will provide physicians, for the first time, with a dynamic evaluation of whether a disease process is present in a patient's diseased cells. In this embodiment, tested pathways can be classified into one of four groups categories: constitutively active, hyperactive, not active at all (hypo-active), or normally active. To determine whether the pathway is diseased and thus suitable for treatment with a targeted therapy known to inhibit the pathway activity of interest, the pathway activity as determined by the methods described herein for a patient suspected of having the disease is compared to a cut-off value derived from a statistical analysis of that pathway activity in a randomly selected population of patients suspected of having the disease. A drug targeting pathways found to have pathway activity that is abnormal (e.g. above a cut-off delineating abnormal and normal pathway activity) would be expected to disrupt that activity, thereby producing the intended effect in a patient.

(ii) Drug Functionality Analysis. This analysis provides two measures of the functionality of a drug ex vivo.

1) Response Score (RS): The response score characterizes the functional effect that a tested drug had on the targeted pathway. It can be reported on a 0-1 scale, where a higher score indicates greater drug functionality.

2) Response Score Percentile Ranking (RSPR): RSPR characterizes how a patient's Response Score ranks relative to the scores received by other patients tested with the same agent. For each patient, the percentile of their Response Score within the total group is determined. Once a percentile ranking has been assigned, patients can then be classified into one of three groups: a) below median, b) near median, or c) above median. For certain drugs, a wide variation in patient drug response as measured by a clinical endpoint such as time to progression (TTP) will be mirrored in the variation in Response Scores. Since it is often the case that the TTP period of the 75th percentile patient in a clinical trial is 5-10 times greater than the TTP period of the 25th percentile patient, providing physicians with the relative rank of their patient's response score gives them important interpretive context. For instance, they could estimate the TTP period for an individual patient based on the TTP period of patients in a clinical trial at the percentile range that corresponds to the Response Score percentile of the individual patient.

(iii) Prediction of Likely Clinical Outcome. This analysis reflects the correlation found in a clinical trial between the Response Score and the clinical endpoint for patients tested and observed after receiving the agent in question. With this correlation, it is possible to identify the clinical outcome that is consistent with patients who received a certain Response Score in a clinical trial. For example, if TTP was the clinical outcome measured, a patient's results could be classified into one of three categories.
1) Likely TTP Period—Lowest: Patients falling into this sub-population are likely to experience a TTP period that is well below the median TTP period the entire population of patients would experience.
2) Likely TTP Period—Indeterminate: No assessment is provided for patients who receive a Response Score that falls in this category.
3) Likely TTP Period—Highest: Patients falling into this sub-population are likely to experience a TTP period that is well above the median TTP period the entire group of patients would experience.

Clinicians would use the results of the CELx Profile test as guidance as they determine which drug therapy to select. When a patient's cells are tested with multiple activating agents and targeted therapeutics, the likely clinical outcome of each drug or combination of drugs can be compared so that the physician can select the drug or combination of drugs with a test result that correlates to the greatest likely clinical outcome.

L. Kits

In another aspect of the invention, kits are provided. In certain embodiments, the kit comprises a container for a disease cell sample from an individual subject containing a transport medium; a container for a control cell sample from the individual subject containing a transport medium; a biosensor; a non-transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, cell cycle, anabolism, catabolism, small molecule synthesis and generation, turnover, and respiration, ATP, calcium, magnesium, and other charged ions, proteins, specific pathway member molecules, DNA and or RNA in various cellular compartments, genomics, and proteomics, post-translational modifications and mechanisms, levels of secondary messenger, cAMP, mRNA, RNAi, microRNAs and other RNA with physiologic function, and combinations thereof; classifying the output as above or below a cutoff value indicating status as a responder or nonresponder and/or classifying the sample as having no response, weakly responsive, and responsive; and generating a report with the classification.

Types and amount of a disease cell samples are described herein. In certain embodiments, the disease cell sample is a whole cell label free viable cell sample having at least 5,000 cells. In embodiments, a control cell sample is selected from the group consisting of a disease cell sample from the same subject, a healthy cell sample from the same subject, a healthy cell sample from a subject known to be free from disease, a set of samples of healthy material from a sufficient number of patients lacking the disease of interest to derive a normal reference interval, a cell sample known to respond to the therapeutic agent, a cell sample known not to respond to the therapeutic agent, and combinations thereof.

The containers and the transport medium are designed to maintain cell viability and to minimize cell activation. In embodiments, the media and containers are endotoxin free, nonpyrogenic and DNase- and RNase-free. Once obtained the cell samples are maintained in a transport medium that retains the cell viability. Depending on the length of time for transportation to the site of analysis, different media may be employed. In embodiments, when transportation of the tissue sample may require up to 10 hours, the media has an osmolality of less than 400 mosm/L and comprises Na+, K+, Mg+, Cl−, Ca+2, glucose, glutamine, histidine, mannitol, and tryptophan, penicillin, streptomycin, contains essential amino acids and may additionally contain non-essential amino acids, vitamins, other organic compounds, trace minerals and inorganic salts, serum, cell extracts, or growth factors, insulin, transferrin, sodium selenite, hydrocortisone, ethanolamine, phosphophorylethanoloamine, tridothyronine, sodium pyruvate, L-glutamine, to support the proliferation and plating efficiency of human primary cells. Examples of such a media include Celsior media, Roswell Park Memorial Institute medium (RPMI), Hanks Buffered Saline, and McCoy's 5A, Eagle's Essential Minimal Media (EMEM), Dulbecco's modified Eagle's medium (DMEM), Leibovitz L-15, or modifications thereof for the practice of primary cell care.

Biosensors are described herein. In certain embodiments a biosensor is selected from the group consisting of a biosensor that detects a cellular parameter selected from the group consisting of, cell adhesion, cell attachment, cell morphology, cell phenotype, cell proliferation, cell signaling, cell density, cell polarity, pH, $O_2$, $CO_2$, glucose, and combinations thereof. In embodiments, the device is an impedance or an optical device. Biosensors may be optionally coated as described herein. In embodiments, a biosensor is selected that measures a change in a physiological parameter associated with the type of therapeutic and/or activator agent as described herein.

In other embodiments, the kit comprises a non-transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof; classifying the output as a responder or nonresponder and/or no response, weakly responsive, and responsive; and generating a report with the classification.

In other embodiments, the invention provides a computing device or computer readable medium with instructions to implement the methods of the disclosure. The computer readable medium includes non-transitory CD, DVD, flash drive, external hard drive, and mobile device.

The kits and methods described herein can employ the use of a processor/computer system. For example, a general purpose computer system comprising a processor coupled to program memory storing computer program code to implement the method, to working memory, and to interfaces such as a conventional computer screen, keyboard, mouse, and printer, as well as other interfaces, such as a network interface, and software interfaces including a database interface find use one embodiment described herein.

The computer system accepts user input from a data input device, such as a keyboard, input data file, or network interface, or another system, such as the system interpreting, for example, the data generated by the biosensor over a defined period of time, and provides an output to an output device such as a printer, display, network interface, or data storage device. Input device, for example a network interface, receives an input comprising a change in a cellular physiological parameter as described herein and/or quantification of these changes. The output device provides an output such as a display, including one or more numbers and/or a graph depicting the detection and/or quantification of the change in a cellular parameter.

The computer system can be coupled to a data store which stores data generated by the methods described herein. This data is stored for each measurement and/or each subject; optionally a plurality of sets of each of these data types is stored corresponding to each subject. One or more computers/processors may be used, for example, as a separate machine, for example, coupled to computer system over a network, or may comprise a separate or integrated program running on computer system. Whichever method is employed these systems receive data and provide data regarding detection/diagnosis in return.

In some embodiments, the computing device can include a single computing device, such as a server computer. In other embodiments, the computing device can include multiple computing devices configured to communicate with one another over a network (not shown). The computing device can store multiple databases within memory. The databases stored on the computing device can be organized by clinic, practicing clinician, programmer identification code, or any other desired category.

Data from the biosensor can be sent to the remote computing system or another data storage device. The communication process initializes and begins at a start module and proceeds to a connect operation. The connect operation communicatively couples the stored information of the health care provider to the remote computing system, for example, via a cabled connection, a wireless local area network (WLAN or Wi-Fi) connection, a cellular network, a wireless personal area network (WPAN) connection, e.g., BLUETOOTH®, or any desired communication link.

A transfer operation transmits data from the biosensor to the computing device. In an embodiment, the transfer operation encrypts the data before transmitting the data between the devices. The communication process can complete and end at a stop module. Once the biosensor data is transferred to a remote computing device, the data is converted to an output, such as a cell index measurement over time. In certain embodiments, a defined endpoint is selected and is used to classify the cell sample as no response, weakly responsive or responsive as described herein. In embodiments, the status of the analysis of the sample as a responder or non responder is communicated back to the health care provider using a similar process over cabled connection, a wireless local area network (WLAN or Wi-Fi) connection, a cellular network, a wireless personal area network (WPAN) connection, e.g., BLUETOOTH®, or any desired communication link.

In certain embodiments, the computer readable storage medium has computer-executable instructions that, when executed by a computing device, cause the computing device to perform steps comprising: converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof in the presence and/or absence of a therapeutic agent; classifying the output as no response, and responsive at a defined endpoint by comparing the output from biosensor from the cell sample in the presence of the therapeutic agent to the output from biosensor from the cell sample in the absence of the therapeutic agent; and generating a report with the classification. In embodiments, the computer executable instructions comprise instructions for communicating the classification to a health care provider.

In other embodiments, the computer readable storage medium may include instructions for identifying which pathways are operative in the disease cell sample of the subject. The instructions that when executed by a computing device comprise determining whether there is a difference between the output of the biosensor data from a disease cell sample from a subject treated with a first activating or perturbing agent to the output of the biosensor data from a second disease cell sample from the same subject not treated with the first activating or perturbing agent to one another to determine whether the pathway responsive to the first activator or perturbant agent is active in the disease cell sample; identifying the presence of the difference in output as an indication of activity of the pathway, and communicating the activity of the pathway to a health care provider. Activator or perturbant agents and their pathways are described herein.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Discussion of Experimental Design

The methods for measuring cell adhesion changes initiated by activation or inhibition of a signaling pathway as described in the present disclosure are used to make treatment decisions based on identifying the most active signaling pathway in a patient's tumor cells or identifying a signaling pathway that is ultra-sensitive. In light of the fact that the biochemical principles of protein binding are universal across cell types, the methods described herein are thus broadly applicable to all cells and cell pathways where protein and other biomolecular binding can occur.

The current state-of-the-art diagnostic tests cannot directly compare the level of activity of different signaling pathways in a patient's tumor cells or determine whether a specific signaling pathway is ultrasensitive. Hence, they do not provide a method of treating patients with the targeted therapy most likely to benefit a patient. By identifying the most active signaling pathway or identifying a signaling pathway that is abnormally ultra-sensitive, the targeted therapy that affects the most active or ultra-sensitive pathway can be selected and administered to a patient.

The four examples provided below demonstrate various embodiments of the methods of characterizing signaling pathway activity to guide selection of optimal targeted therapies for the purpose of treating a patient. In particular, the examples demonstrate that it is possible to: 1) identify the most active signaling pathways (e.g. HER1, HGFR, FGFR, etc.) in a patient's tumor cells and that the signaling pathways in different patients with the same type of cancer (e.g. breast, lung, colon, etc.) have different levels of activity; 2) identify an abnormally ultra-sensitive signaling pathway in a patient's tumor cells; and 3) identify pathways that are co-activated and require a combination of drugs to get the greatest CELx test output value. These examples confirm that a treatment decision can be made using the status (e.g., most active or ultra-sensitive) of the signaling pathway activity in a patient's tumor cells determined by the present invention.

Example 1: Multiple Pathway Testing

Methods:
Biosensor and transducer: A 96-well impendence E-Plate (ACEA, San Diego, CA) was placed onto an xCELLigence RTCA MP Station impendence biosensor (ACEA, San Diego, CA). The biosensor measured simultaneously the impedance of every well. The change in impedance for a particular well is proportional to the number of cells and type of attachment the cells have with the impedance microplate. Changes in impedance indicate a response to perturbation of these small cell populations.
Coatings: The 96-E-Plate were wells were coated with fibronectin and or collagen. Collagen is purchased from Advanced BioMatrix (Carlsbad, CA) and fibronectin from Sigma-Aldrich (St. Louis, MO).
Tissue and cell samples: A total of 18 samples of human tumor cells from breast, lung, colon, ovarian, kidney, bladder cancer were studied. For each of these six different cancer types, tumor cell samples from three different patients were tested. Any biomarkers that are used to guide selection of targeted therapy are listed in Table 18 for each patient if they were present.
Signaling Pathways activator agent and targeted therapeutic pairs: Eleven different signaling pathways were studied in each human tumor cell sample using ten different signaling pathway activator agent and targeted therapeutic pairs. Each of the signaling pathway activator agent and targeted therapeutic pairs affect the same signaling pathway. Each of the signaling pathway activator agents is a well-characterized and specific agonist of its associated signaling pathway and each of the targeted therapeutic agents is a well-characterized and specific antagonist of the same associated signaling pathway. The signaling pathway activator agents and targeted therapeutics used to characterize the activity level of the associated signaling pathway are summarized in Table 16 below:

TABLE 16

Signaling Pathway Activator and Targeted Therapeutic Agents
Used to Test the Activity Level of Their Corresponding Pathways

| Pathway | Signaling Pathway Activator Agent | Targeted Therapeutic Agent |
| --- | --- | --- |
| HER2/HER1 | EGF | Pertuzumab |
| HER2/HER3 | NRG1 | Pertuzumab |
| EGFR | EGF | Neratinib |
| HER3 | NRG1 | Neratinib |
| HER2 | — | Pertuzumab |
| c-MET/HGF | HGF | SGX-523 |
| FGFR | FGF | BGJ398 |
| IGFR | IGF | Linsitinib |

TABLE 16-continued

Signaling Pathway Activator and Targeted Therapeutic Agents
Used to Test the Activity Level of Their Corresponding Pathways

| Pathway | Signaling Pathway Activator Agent | Targeted Therapeutic Agent |
| --- | --- | --- |
| ALK | FAM150A | Ceritinib |
| Axl | Gas6 | R428 (BGB324) |
| FLT3 | FL | Gilteritnib |

Other Reagents: Standard media antibiotics (e.g. penicillin, streptomycin) and other buffers were purchased and used as delivered from ATCC (Manassas, VA, USA) or Life Technologies (Grand Island, NY).
Procedure: For each test of a patient cell sample with a pair of signaling pathway activator and targeted therapeutic agents, six wells were seeded with approximately 15,000 cells in 120 uL culture media. Twenty microliters of the targeted therapeutic agent were added to two wells of each patient's cells and 20 microliters of standard media were added to the other four wells for each patient 18 hours in advance of addition of the signaling pathway activator agent. Signaling pathway stimulation was initiated with the addition of 20 ul of the signaling pathway activator agent in the two wells that received a targeted therapeutic agent and in two additional wells for each patient's set of cells without the targeted therapeutic. The impedance recording of attachment and adhesion change was performed at 37° C., 5% C02. Data was recorded on a continuous basis throughout the test, where the data presented is from the initial baseline level of cell attachment compared to the subsequent effects following the targeted therapeutic agent and the signaling pathway activator agent additions on the 18 different patient samples.
Results:
Table 17 presents the results, expressed as an output value, for each of the 167 tests performed using the methods described above. For each of the 18 patient samples, up to 11 different signaling pathways were tested. The output value represents the difference between the amount of cell adhesion change resulting from addition of the signaling pathway activator agent and the amount of cell adhesion change resulting from addition of the targeted therapeutic agent. For each patient tested, the activity of at least one signaling pathway was significantly higher than the other nine signaling pathways tested. The targeted therapeutic agent associated with the most active signaling pathway is the one administered to the patient.

TABLE 17

Results for a Test of Signaling Pathway Activity using Different Pairs of Signaling Pathway Activator and Targeted Therapeutic Agents (Up to 11 Pathways tested in 18 sets of patient tumor cells)

| Pathway | Breast | | | Lung | | |
| --- | --- | --- | --- | --- | --- | --- |
| | C34 | C2 | C21 | C23 | C24 | C25 |
| HER2/HER1 | −176 | 28 | 40 | −6 | 54 | 38 |
| HER2/HER3 | 88 | 426 | −48 | 61 | 13 | 9 |
| EGFR | 247 | −19 | 503 | 298 | 245 | 209 |
| HER3 | 4 | −1 | 234 | 373 | 194 | 116 |
| HER2 | −90 | 454 | −9 | −55 | 66 | 47 |
| FGFR | 33 | 14 | 15 | 1 | −6 | 14 |
| c-MET/HGF | 6 | 0 | 222 | 469 | 78 | 132 |
| IGFR | 34 | 20 | 69 | 32 | −61 | −44 |
| ALK | 15 | 5 | 10 | 16 | 2 | 8 |
| Axl | 44 | 5 | 6 | 24 | 7 | 30 |

TABLE 17-continued

Results for a Test of Signaling Pathway Activity using Different Pairs of Signaling Pathway Activator and Targeted Therapeutic Agents (Up to 11 Pathways tested in 18 sets of patient tumor cells)

| | | | | | | |
|---|---|---|---|---|---|---|
| FLT3 | 10 | 7 | 9 | — | — | — |

| | Colorectal | | | Bladder | | |
|---|---|---|---|---|---|---|
| Pathway | C71 | C72 | C62 | C82 | C87 | C81 |
| HER2/HER1 | −10 | 0 | 0 | 1 | 46 | 1 |
| HER2/HER3 | 175 | 21 | 24 | 5 | 477 | 4 |
| EGFR | 179 | 5 | 28 | 345 | 334 | 344 |
| HER3 | 28 | 5 | 2 | 31 | 10 | 13 |
| HER2 | 165 | 21 | 24 | 6 | 523 | 5 |
| FGFR | 43 | −20 | 4 | −94 | 8 | 75 |
| c-MET/HGF | 53 | −110 | −6 | 41 | 28 | 419 |
| IGFR | −2 | −22 | 6 | 21 | 210 | 351 |

| | Kidney | | | Ovarian | | |
|---|---|---|---|---|---|---|
| Pathway | C90 | C88 | C92 | C69 | C77 | C54 |
| HER2/HER1 | 35 | −24 | 3 | −115 | 67 | 180 |
| HER2/HER3 | −3 | 46 | −20 | 95 | 294 | 356 |
| EGFR | 150 | −67 | 290 | 614 | −78 | 654 |
| HER3 | −32 | 5 | 36 | 178 | 128 | 244 |
| HER2 | 32 | 16 | 23 | −20 | 361 | 537 |
| FGFR | −47 | 251 | 6 | −19 | 12 | 65 |
| c-MET/HGF | 368 | −13 | 154 | −27 | 227 | 123 |
| IGFR | −607 | 143 | 73 | −111 | 56 | −8 |

TABLE 17-continued

Results for a Test of Signaling Pathway Activity using Different Pairs of Signaling Pathway Activator and Targeted Therapeutic Agents (Up to 11 Pathways tested in 18 sets of patient tumor cells)

| | | | | | | |
|---|---|---|---|---|---|---|
| ALK | — | — | — | 16 | 37 | 14 |
| Axl | — | — | — | 10 | 5 | 12 |
| FLT3 | — | — | — | — | 6 | 10 |

Discussion:

Table 18 below lists for each patient the biomarkers present (if any) in their cells that would be used to guide selection of a targeted therapy. The Table also lists the corresponding targeted therapy that would be used to treat the patient if a biomarker was present. Many of the patients lack any treatment-relevant biomarker and thus without the present invention, they would not be eligible to receive a targeted therapy. In addition, the table lists the potential targeted therapeutic that is recommended for administration to the patient based on the methods described by the present invention.

For 17 of the 18 patients tested, the targeted therapeutic that is administered using the results of this method described herein is different than the targeted therapy current standard-of-care treatment guidelines recommend. In many cases, no targeted therapeutic would be prescribed based on current treatment guidelines. This example confirms the importance of measuring the activity of a cancer's patients signaling pathways since in many cases, the current standard-of-care therapies prescribed do not treat the underlying disease mechanism, i.e. a demonstrated specific signaling pathway dysfunction in that patient.

TABLE 18

Targeted Therapeutic Selection Standard-of Care Method Using a Biomarker vs. CELx Method of Selecting Targeted Therapeutic that Treats Most Active Signaling Pathway

| | Breast | | | Lung | | |
|---|---|---|---|---|---|---|
| | C34 | C2 | C21 | C23 | C24 | C25 |
| Status of Biomarkers (+/−) used to Select SOC Targeted Drugs | HER2− ER+ | HER2− ER+ | HER2− ER+ | ALK− EGFR− | ALK− EGFR− | ALK− EGFR− |
| Targeted Drug Eligible to Receive based on Biomarker Status | Letrozole Tamoxifen | Letrozole Tamoxifen | Letrozole Tamoxifen | None | None | None |
| Targeted Therapeutic selected with CELx method | Neratinib | Pertuzumab | Neratinib + SGX-523 | SGX-523 | Neratinib | Neratinib |
| Did CELx Method Result in Selection of New Drug | Yes | Yes | Yes | Yes | Yes | Yes |

| | Colorectal | | | Bladder | | |
|---|---|---|---|---|---|---|
| Pathway | C71 | C72 | C62 | C82 | C87 | C81 |
| Status of Biomarkers (+/−) used to Select SOC Targeted Drugs | EGFR− | EGFR− | EGFR− | None | None | None |
| Targeted Drug Eligible to Receive based on Biomarker Status | None | None | None | None | None | None |
| Targeted Therapeutic selected with CELx method | Pertuzumab | SGX-523 | None | Neratinib | Neratinib + Lisitinib | SGX-523 + Lisitinib |

TABLE 18-continued

| | | | | | | |
|---|---|---|---|---|---|---|
| Did CELx Method Result in Selection of New Drug | Yes | Yes | No | Yes | Yes | Yes |

| | Kidney | | | Ovarian | | |
|---|---|---|---|---|---|---|
| Pathway | C90 | C88 | C92 | C69 | C77 | C54 |
| Status of Biomarkers (+/−) used to Select SOC Targeted Drugs | None | None | None | BRCA− | BRCA− | BRCA− |
| Targeted Drug Eligible to Receive based on Biomarker Status | None | None | None | None | None | None |
| Targeted Therapeutic selected with CELx method | SGX-523 + Lisitinib | SGX-523 + BGJ938 | Neratinib + SGX-523 | Neratinib | Neratinib + SGX-523 | Neratinib |
| Did CELx Method Result in Selection of New Drug | Yes | Yes | Yes | Yes | Yes | Yes |

Example 2: Pathway Ultrasensitivity Testing

Methods:

Biosensor and transducer: A 96-well impendence E-Plate (ACEA, San Diego, CA) was placed onto an xCELLigence RTCA MP Station impendence biosensor (ACEA, San Diego, CA). The biosensor measured simultaneously the impedance of every well. The change in impedance for a particular well is proportional to the number of cells and type of attachment the cells have with the impedance microplate. Changes in impedance indicate a response to activation of these small cell populations.

Coatings: The 96-E-Plate were wells were coated with fibronectin and or collagen. Collagen is purchased from Advanced BioMatrix (Carlsbad, CA) and fibronectin from Sigma-Aldrich (St. Louis, MO).

Tissue and cell samples: Five different samples of human cells from breast tumors (R131, R39, R36, R20, R82) and two different samples of human cells from non-small cell lung cancer (NSCLC) tumors were studied (C15 and C23). Any biomarkers that are used to guide selection of targeted therapy are listed in Table 20 for each patient if they were present.

Signaling Pathways activator: NRG1, a HER3 agonist, was used to stimulate the HER3 pathway in each of the five breast cancer cell samples. The EC90 and EC10 concentrations of the signaling pathway activator agent were also derived for each breast cancer sample. Table 19 provides a summary.

TABLE 19

| Cell Sample | R131 | R39 | R36 | R20 | R82 |
|---|---|---|---|---|---|
| Pathway stimulated | HER3 | HER3 | HER3 | HER3 | HER3 |
| Activating agent | NRG1 | NRG1 | NRG1 | NRG1 | NRG1 |
| EC90 Concentration | 1,227 pM | 1,597 pM | 1,955 pM | 2,144 pM | 1,787 pM |
| EC10 Concentration | 133 pM | 173 pM | 215 pM | 236 pM | 193 pM |

In each of the two NSCLC cell samples, four different activating agents were used to stimulate either the EGF or HER3 pathways. The EC90 and EC10 concentrations of the signaling pathway activator agent were also derived for each NSCLC cell sample. Table 20 provides a summary.

TABLE 20

| Cell Sample | C15 | | | |
|---|---|---|---|---|
| Pathway stimulated | EGF | EGF | EGF | EGF |
| Activating Agent | Amphiregulin | Betacellulin | HB-EGF | TGF alpha |
| EC90 Concentration | 3000 pM | 100 pM | 102 pM | 362 pM |
| EC10 Concentration | 45.7 pM | 2.4 pM | 1.6 pM | 8.2 pM |

| Cell Sample | C23 | | | |
|---|---|---|---|---|
| Pathway stimulated | EGF | EGF | EGF | HER3 |
| Activating Agent | Betacellulin | HB-EGF | TGF alpha | NRG1 |
| EC90 Concentration | 194 pM | 200 pM | 187 pM | 4463 pM |
| EC10 Concentration | 6.6 pM | 3.0 pM | 8.8 pM | 399 pM |

Other Reagents: Standard media antibiotics (e.g. penicillin, streptomycin) and other buffers were purchased and used as delivered from ATCC (Manassas, VA, USA) or Life Technologies (Grand Island, NY).

Procedure: For each test of a patient cell sample with two different concentrations of signaling pathway activator, six wells were seeded with approximately 15,000 cells in 120 uL culture media. Twenty microliters of the signaling pathway activator agent representing approximately the EC90 concentration was added to two wells of each patient's cells, 20 microliters of the signaling pathway agent representing approximately the EC10 concentration was added to two wells of each patient's cells, and 20 microliters of standard media were added to the other two wells for each patient. The impedance recording of attachment and adhesion change was performed at 37° C., 5% CO2. Data was recorded on a continuous basis throughout the test, where the data presented is from the initial baseline level of cell attachment compared to the subsequent effects following the additions of two concentrations of the signaling pathway activator agent on the 12 different patient samples.

Results:

Tables 21, 22, and 23 summarize the results. For each patient cell sample tested, output values were calculated for the signaling pathway activity measured after addition of the two different concentrations of the signaling pathway activator agent. To determine the sensitivity of the signaling pathway to the signaling pathway activator agent, the sensitivity was calculated using the two output values. When the ratio of the EC90 to EC10 is less than 81, the pathway is considered to be ultra-sensitive; otherwise the pathway is considered to be normally sensitive.

Table 21 presents the results for the breast cancer cell samples tested. Four of the five breast cancer patient samples studied here had EC90 to EC10 ratios less than 81, which means the signaling pathways tested were ultra-sensitive. A targeted therapeutic that affects the same signaling pathway found to be ultra-sensitive was identified so that it could be compared the therapeutic that would have been prescribed for the patient based on their biomarkers status.

TABLE 21

Evaluation of Patient Tumor Cell Samples with Ultra-Sensitive Signaling Pathways

| Tumor Type Cell Sample | Breast R131 | Breast R39 | Breast R36 | Breast R20 | Breast R82 |
|---|---|---|---|---|---|
| Pathway | HER3 | HER3 | HER3 | HER3 | HER3 |
| Activating Agent | NRG1 | NRG1 | NRG1 | NRG1 | NRG1 |
| Sensitivity Calculation Result* | 38.32 | 45.96 | 27.61 | 18.44 | 95.1 |
| Pathway Sensitivity Status (normal or ultra) | Ultra | Ultra | Ultra | Ultra | Normal |
| Status of Biomarkers (+/−) used to Select SOC Targeted Drug | HER2− ER+ | HER2− ER+ | HER2− ER+ | HER2− ER+ | HER2− ER+ |
| Targeted Drug Patient is Eligible to Receive based on Biomarker Status (SOC) | Letrozole | Letrozole | Letrozole | Letrozole | Letrozole |
| Targeted Therapeutic affecting signaling pathway tested | Neratinib | Neratinib | Neratinib | Neratinib | Neratinib |
| Is targeted therapeutic affecting ultra-sensitive signaling pathway different than therapy selected on basis of biomarker status? | Yes | Yes | Yes | Yes | No |

*$EC_{90}/EC_{10}$ ratio is reported

Tables 22 and 23 present the results for the NSCLC cell samples tested. In both NSCLC cell samples, each of the four activating agents studied here had EC90 to EC10 ratios less than 81, which means the signaling pathways tested were ultra-sensitive. A targeted therapeutic that affects the same signaling pathway found to be ultra-sensitive was identified so that it could be compared the therapeutic that would have been prescribed for the patient based on their biomarkers status.

TABLE 22

| Tumor Type | NSCLC | | | |
|---|---|---|---|---|
| Cell Sample # | C15 | | | |
| Pathway | EGF | EGF | EGF | EGF |
| Activating Agent | Amphiregulin | Betacellulin | HB-EGF | TGF alpha |
| Sensitivity Calculation Result* | 65.65 | 41.67 | 63.75 | 44.15 |
| Pathway Sensitivity Status (normal or ultra) | Ultra | Ultra | Ultra | Ultra |
| Status of Biomarkers (+/−) used to Select SOC Targeted Drug | EGFR− | EGFR− | EGFR− | EGFR− |

TABLE 22-continued

| Tumor Type | NSCLC | | | |
|---|---|---|---|---|
| Cell Sample # | C15 | | | |
| Pathway | EGF | EGF | EGF | EGF |
| Targeted Drug Patient is Eligible to Receive based on Biomarker Status (SOC) | Chemotherapy | Chemotherapy | Chemotherapy | Chemotherapy |
| Targeted Therapeutic affecting signaling pathway tested | Afatinib | Afatinib | Afatinib | Afatinib |
| Is targeted therapeutic affecting ultra-sensitive signaling pathway different than therapy selected on basis of biomarker status? | Yes | Yes | Yes | Yes |

TABLE 23

| Tumor Type | NSCLC | | | |
|---|---|---|---|---|
| Cell Sample # | C23 | | | |
| Pathway | EGF | EGF | EGF | HER3 |
| Activating Agent | Betacellulin | HB-EGF | TGF alpha | NRG1 |
| Sensitivity Calculation Result* | 29.39 | 66.67 | 21.25 | 11.19 |
| Pathway Sensitivity Status (normal or ultra) | Ultra | Ultra | Ultra | Ultra |
| Status of Biomarkers (+/−) used to Select SOC Targeted Drug | EGFR− | EGFR− | EGFR− | EGFR− |
| Targeted Drug Patient is Eligible to Receive based on Biomarker Status (SOC) | Chemotherapy | Chemotherapy | Chemotherapy | Chemotherapy |
| Targeted Therapeutic affecting signaling pathway tested | Afatinib | Afatinib | Afatinib | Afatinib |
| Is targeted therapeutic affecting ultra-sensitive signaling pathway different than therapy selected on basis of biomarker status? | Yes | Yes | Yes | Yes |

Discussion:

For five of the six patient cells tested, the targeted therapeutic that would be administered on the basis of the ultra-sensitive status of the associated signaling pathway is different than the targeted therapy current standard-of-care treatment guidelines recommend. This example confirms the importance of determining whether a signaling pathway is ultra-sensitive, since in many cases, the current standard-of-care therapies prescribed on the basis of a genomic biomarker status do not treat the underlying disease mechanism, i.e. ultra-sensitive signaling pathway function.

Example 3: Testing of Multiple Pathways Simultaneously

Methods:

Biosensor and transducer: A 96-well impendence E-Plate (ACEA, San Diego, CA) was placed onto an xCELLigence RTCA MP Station impendence biosensor (ACEA, San Diego, CA). The biosensor measured simultaneously the impedance of every well. The change in impedance for a particular well is proportional to the number of cells and type of attachment the cells have with the impedance microplate. Changes in impedance indicate a response to perturbation of these small cell populations.

Coatings: The 96-E-Plate were wells were coated with fibronectin and or collagen. Collagen is purchased from Advanced BioMatrix (Carlsbad, CA) and fibronectin from Sigma-Aldrich (St. Louis, MO).

Tissue and cell samples: Six samples of human tumor cells from breast cancer were studied (C1815, C1596, C1838, C135, C42, C264). Any biomarkers that are used to guide selection of targeted therapy are listed in Table 22 for each patient if they were present.

Signaling Pathways activator agent and targeted therapeutic pairs: In each human tumor cell sample, gross signaling activity of the HER1, HER3 and c-Met pathways initiated by three activator agents (EGF, NRG1, HGF) in combination was quantified. In addition, the amount of signaling pathway activity initiated by an activator agent that was inhibited by five different drugs (neratinib, 2C4, HER1+HER3 mAb, tepotinib, taselisib) in a total of 11 different single drug or multiple drug combinations was quantified. Each of the signaling pathway activator agents is a well-characterized and specific agonist of its associated signaling pathway. Four of the targeted therapeutics tested—neratinib, 2C4, HER1+

HER3 mAb, and tepotinib—are well-characterized and specific antagonists of at least one of the signaling pathways activated by the growth factors. The fifth targeted therapeutic tested, taselisib, is an inhibitor that binds to PI3k, which downstream of the HER family and c-Met receptors.
Other Reagents: Standard media, antibiotics (e.g. penicillin, streptomycin), and other buffers were purchased and used as delivered from ATCC (Manassas, VA, USA) or Life Technologies (Grand Island, NY).

Procedure:

For each test of a patient cell sample with a signaling pathway activator(s) and targeted therapeutic agent(s), six or eight wells were seeded with approximately 15,000 cells in 120 uL culture media; six wells were seeded when only a single drug was evaluated and eight wells were seeded when two drugs were evaluated. When only a single drug was evaluated, 20 uL of the targeted therapeutic agent was added to two wells of each patient's cells and the final concentration of the therapeutic agent in the two wells with the single therapeutic agent was 500 nanomolar. When two therapeutic agents were evaluated, two wells of patient cells received 20 uL of the combined therapeutic agents at a concentration of 500 nanomolar each and an additional two wells of patient cells received 20 uL of the combined therapeutic agents at a concentration of 50 nanomolar each. Twenty microliters of standard media were added to the other four wells for each patient 18 hours in advance of addition of the signaling pathway activator agent(s). Signaling pathway stimulation was initiated with the addition of 20 ul of the signaling pathway activator agent(s) in the two or four wells that received a targeted therapeutic agent(s) and two additional wells for each patient's set of cells. The impedance recording of attachment and adhesion change was performed at 37° C., 5% CO2. Data was recorded on a continuous basis throughout the test, where the data presented if from the initial baseline level of cell attachment compared to the subsequent effects following the targeted therapeutic agent(s) and the signaling pathway activator agent(s) additions on the nine different patient samples.

Results:

Table 24 presents the results, expressed as an output value, for each of the 102 tests performed using the methods described above. For each of the six patient samples, three different signaling pathways (HER1, HER3, c-Met) were activated simultaneously. The output value represents the difference between the amount of cell adhesion change resulting from addition of the signaling pathway activator agent(s) and the amount of cell adhesion change resulting from addition of the targeted therapeutic agent(s). The targeted therapeutic agent(s) that inhibited the most signaling pathway activity of the cells stimulated alone or with multiple signaling pathway activator agents would be the one selected to treat the patient.

TABLE 24

Results for a Test of Signaling Pathway Activity using Different Signaling Pathway Activator(s) and Targeted Therapeutic Agents (3 Pathways tested simultaneously with 6 sets of patient tumor cells)

| Targeted Therapeutic Agents | C1815 | C1596 | C1838 | C135 | C42 | C264 |
|---|---|---|---|---|---|---|
| Neratinib | 630 | 691 | 689 | 622 | 500 | 464 |
| 2C4 | 370 | 426 | 499 | 546 | 269 | 322 |
| HER1 + 3 mAb's | 493 | 642 | 647 | 487 | 400 | 442 |
| Taselisib | 385 | 242 | 271 | 583 | 246 | 276 |
| Tepotinib | 473 | 330 | 12 | 73 | 223 | 172 |
| Neratinib + Taselisib (500 nM) | 876 | 964 | 1034 | 1264 | 804 | 728 |
| Neratinib + Taselisib (50 nM) | 710 | 791 | 773 | 936 | 539 | 529 |
| Neratinib + Tepotinib (500 nM) | 1072 | 1140 | 1163 | 1433 | 978 | 851 |
| Neratinib + Tepotinib (50 nM) | 902 | 964 | 1036 | 1189 | 820 | 677 |
| 2C4 + Taselisib (500 nM) | 688 | 796 | 806 | 1056 | 629 | 586 |
| 2C4 + Taselisib (50 nM) | 464 | 594 | 598 | 816 | 379 | 400 |
| 2C4 + Tepotinib (500 nM) | 670 | 832 | 790 | 811 | 720 | 658 |
| 2C4 + Tepotinib (50 nM) | 641 | 715 | 630 | 830 | 670 | 457 |
| HER1 + 3 + Taselisib (500 nM) | 760 | 844 | 785 | 1042 | 622 | 548 |
| HER1 + 3 + Taselisib (50 nM) | 559 | 682 | 587 | 857 | 445 | 386 |
| HER1 + 3 + Tepotinib (500 nM) | 944 | 1020 | 942 | 1207 | 872 | 700 |
| HER1 + 3 + Tepotinib (50 nM) | 792 | 854 | 688 | 958 | 763 | 530 |

Table 25 below lists for each patient the biomarkers present in their cells and the corresponding targeted therapy that would be used to treat the patient. In addition, Table 25 lists the potential targeted therapeutic that is recommended for administration to the patient based on the methods described by the present disclosure.

TABLE 25

Targeted Therapeutic Selection
Standard-of Care Method Using a Biomarker vs. CELx Method of Selecting Targeted Therapeutic that Treats Most Active Signaling Pathway

|  | C1815 | C1596 | C1838 | C135 | C42 | C264 |
|---|---|---|---|---|---|---|
| Status of Biomarkers (+/−) used to Select SOC Targeted Drugs | HER2− ER+ | HER2− ER+ | HER2− ER+ | HER2− ER+ | HER2− ER+ | HER2− ER+ |
|  | C1815 | C1596 | C1838 | C135 | C42 | C264 |
| Targeted Drug Eligible to Receive based on Biomarker Status | Letrozole Tamoxifen | Letrozole Tamoxifen | Letrozole Tamoxifen | Letrozole Tamoxifen | Letrozole Tamoxifen | Letrozole Tamoxifen |

TABLE 25-continued

Targeted Therapeutic Selection
Standard-of Care Method Using a Biomarker vs. CELx Method of Selecting Targeted
Therapeutic that Treats Most Active Signaling Pathway

|  | C1815 | C1596 | C1838 | C135 | C42 | C264 |
|---|---|---|---|---|---|---|
| Targeted Therapeutic selected with CELx method | Neratinib + Tepotinib | Neratinib + Tepotinib | Neratinib + Tepotinib | Neratinib + Tepotinib | Neratinib + Tepotinib | Neratinib + Tepotinib |
| Did CELx Method Result in Selection of New Drug(s) | Yes | Yes | Yes | Yes | Yes | Yes |

Discussion:

For each of the six patients tested, the targeted therapeutic that would be selected administered using the results of this method described herein is different than the targeted therapy current standard-of-care treatment guidelines recommend. For each patient, the output value recorded with two drugs tested at a 50 nanomolar concentration was nearly the same as the output value when the same two drugs were tested at a 500 nanomolar concentration. For four of the patients, the test of two drugs simultaneously generated a higher output value than the combined output value of the same two drugs when evaluated individually. These results demonstrate the synergy of using drugs in combination when they are treating co-activated pathways. This example confirms the importance of measuring the activity of a cancer's patients signaling pathways since the current standard-of-care therapies prescribed did not treat the underlying disease mechanism, i.e. a demonstrated specific signaling pathway dysfunction in that patient. This example also confirms the benefit of testing multiple activator and therapeutic agents simultaneously. Finally, the tests involving a PI3k inhibitor, taselisib, demonstrate the effect on signaling activity of a node inhibitor downstream of the binding site of the activator agents.

Example 4: Mouse Xenograft Study of Two Drugs Treating Two Pathways

Abnormal c-Met signaling, including cross-talk between c-Met and ErbB family receptors, is suspected of playing a role in a variety of cancer types. However, clinical trials evaluating investigational anti-Met therapies, alone and in combination with other targeted therapies in breast and lung cancer, have produced mostly negative results. These trials enrolled subjects with c-MET protein overexpression or gene amplification, indicating a low correlation between receptor status and targeted therapeutic response. To demonstrate the advantages of measuring the activity of multiple signaling pathways using live tumor cells with the present invention, a mouse xenograft study was performed whose results were compared to results obtained with a CELx test described by the present invention.

Methods:

A HER2+ tumor cell sample, C21, was tested using essentially the same methods described in Examples 1 and 3 above to evaluate the status of the c-Met, EGFR, HER2 and HER3 pathways. The cells were also tested with NRG1, EGF, and HGF activating agents added simultaneously and another portion of the same sample where these combined activating agents were tested with neratinib (pan-HER inhibitor), tepotinib, (c-Met inhibitor), and neratinib and tepotinib combined to measure the effect of these targeted therapies on these pathways when activated simultaneously. This cell sample was found to have normal HER2 signaling, abnormal EGFR signaling, and abnormal c-Met signaling. Thus, this cell sample was suitable to assess whether cells found to be responsive to c-Met and EGFR inhibitors ex vivo in the CELx test would respond to these same inhibitors when another portion of the same cell sample was implanted in a xenograft mouse model.

For the xenograft study, 40 female NSG mice were each injected with two million C21 cells. Mice were randomly assigned to one of four 10-mouse arms that were treated as follows: 1) a control group that received vehicle; 2) neratinib, a pan-HER inhibitor; 2) tepotinib, a c-Met inhibitor; or 3) neratinib and tepotinib. The mice were treated for 16 days.

Results:

The CELx ex vivo test demonstrated that when the C21 sample was agonized only by HGF (a c-Met ligand), the percentage of c-Met signaling activity inhibited by tepotinib, a highly specific c-Met inhibitor, was nearly 100%. This demonstrated the specificity of the c-Met activity measured. When the C21 cell sample was simultaneously agonized with NRG1, EGF, and HGF (i.e., simultaneous activation of HER family signaling pathways and the c-Met signaling pathway) and antagonized with tepotinib alone (a c-Met inhibitor), less than 10% of the total signaling was inhibited. However, when the C21 cell sample was simultaneously agonized with NRG1, EGF, and HGF and antagonized with tepotinib (a c-Met inhibitor) and neratinib (a pan-HER inhibitor that inhibits the EGFR signaling pathway) combined, the percentage of c-Met and EGFR signaling activity inhibited was nearly 100%. The increase in c-Met and EGFR signaling inhibition by tepotinib when combined with an EGFR inhibitor suggests the c-Met signaling activity is co-activated with the EGFR signaling activity. This finding is not related to the receptor or gene amplification status of either receptor, nor observable when signaling activity is measured in isolation. This highlights the advantages of evaluating multiple signaling pathways simultaneously in live cells.

In light of these ex vivo results, it would be expected that a mouse xenograft with C21 cells would exhibit the highest level of drug response when treated with a combination of an EGFR inhibitor like neratinib and a c-Met inhibitor like tepotinib. To test this, the four-arm mouse xenograft study described above was performed, the results of which are shown in FIG. 1. The difference in tumor volume between the control and tepotinib only-treated groups after 16 days of treatment was 10%. However, tumor volumes relative to the control were reduced by 52% in the neratinib only-treated group and by 73% in the tepotinib+neratinib-treated group. Thus, these results are consistent with the results of the CELx signaling analysis that revealed tepotinib as a single-agent was not as effective as it is when combined with an EGFR inhibitor like neratinib.

Discussion:

The superior tumor reduction of the tepotinib and neratinib drug combination relative to tepotinib alone in the xenograft study confirms the advantages of using a multi-pathway CELx analysis described by the present invention over a genomic biomarker analysis to select drug treatments. Without a CELx analysis of the c-Met and EGFR signaling activity alone and simultaneously in the C21 cells, there would have been no basis to suspect that a c-Met inhibitor would provide any benefit to a patient, much less that it would provide improved efficacy when combined with an EGFR inhibitor.

What is claimed is:

1. A method of treating a human subject diagnosed with cancer, the method comprising:
   administering to the subject at least one targeted therapeutic that targets a signaling pathway selected from the group consisting of Protein kinase B (AKT), Phosphoinositide 3-kinase (PI3K), MAPK/ERK kinase (MEK), Extracellular signal-regulated kinase (ERK) and Mammalian target of rapamycin (mTOR), wherein the at least one targeted therapeutic is therapeutically active in said signaling pathway in the subject's cancer cells by a method comprising:
   culturing a sample comprising viable cancer cells obtained from the subject;
   contacting the sample with at least one triplet set of agents, each triplet set comprised of a first agent targeted therapeutic and at least two second agent activators that are known to selectively affect the same signaling pathway the targeted therapeutic is intended to address, so as to upregulate or downregulate the signaling pathway as measured by an effect on cell adhesion or attachment, to produce a sample contacted with at least one triplet set of agents;
   continuously measuring cell adhesion or attachment of the viable cancer cells in the sample contacted with the at least one triplet set of agents, relative to a sample of viable cancer cells obtained from the subject that is contacted with the first agent targeted therapeutic or each of the second agent activators alone;
   determining an output value, expressed as a percentage, for the at least one triplet set of agents that characterizes whether a change in cell adhesion or attachment has occurred in the sample contacted with the triplet set of agents, as compared to the sample contacted with the first agent targeted therapeutic or the second agent activators alone; and
   administering to the subject the at least one targeted therapeutic that affects the same signaling pathway as the first agent targeted therapeutic from the triplet set of agents when the output value percentage is greater than 50% indicating the targeted therapeutic is therapeutically active in the cell signaling pathway of the subject's cancer cells.

2. A method of treating a human subject diagnosed with cancer, the method comprising:
   administering to the subject at least one targeted therapeutic that targets a signaling pathway selected from the group consisting of Protein kinase B (AKT), Phosphoinositide 3-kinase (PI3K), MAPK/ERK kinase (MEK), Extracellular signal-regulated kinase (ERK) and Mammalian target of rapamycin (mTOR), wherein the at least one targeted therapeutic is therapeutically active in said signaling pathway in the subject's cancer cells by a method comprising:
   culturing a sample comprising viable cancer cells obtained from the subject;
   contacting the sample simultaneously with at least one triplet set of agents, each triplet set comprised of a first agent targeted therapeutic, a second agent activator that is known to selectively affect the same signaling pathway the first agent is intended to address and a third agent targeted therapeutic that affects a different signaling pathway than the first agent or a different location within the signaling pathway that the first agent affects, so as to upregulate or downregulate the signaling pathway that the first agent affects as measured by an effect on cell adhesion or attachment, to produce a sample contacted with at least one triplet set of agents;
   continuously measuring cell adhesion or attachment of the viable cancer cells in the sample contacted with the at least one triplet set of agents, relative to a sample of viable cancer cells obtained from the subject that is contacted with the first agent targeted therapeutic alone, the second agent activator alone or the third agent targeted therapeutic alone;
   determining an output value, expressed as a percentage, for the at least one triplet set of agents that characterizes whether a change in cell adhesion or attachment has occurred in the sample contacted with the triplet set of agents, as compared to the sample contacted with the first agent targeted therapeutic alone, the second agent activator alone or the third agent targeted therapeutic alone; and
   administering to the subject the at least one targeted therapeutic that affects the same signaling pathway as the first agent targeted therapeutic from the triplet set of agents when the output value percentage is greater than 50% indicating the first agent targeted therapeutic agent is therapeutically active in the cell signaling pathway of the subject's cancer cells.

3. The method of claim 1, which comprises contacting the sample with a targeted therapeutic that inhibits a PI3K or mTOR signaling pathway and with an activator of the PI3K or mTOR signaling pathway.

4. The method of claim 1, wherein cell adhesion or attachment is measured using an impedance biosensor or an optical biosensor.

5. The method of claim 1, wherein the cancer is selected from the group consisting of breast cancer, lung cancer, colorectal cancer, bladder cancer, kidney cancer, ovarian cancer and leukemia.

6. The method of claim 1, wherein the targeted therapeutic that is administered to the subject is the first agent targeted therapeutic.

7. The method of claim 1, wherein the targeted therapeutic that is administered to the subject is different than the first agent but targets the same signaling pathway as the first agent.

8. The method of claim 2, wherein cell adhesion or attachment is measured using an impedance biosensor or an optical biosensor.

9. The method of claim 2, wherein the cancer is selected from the group consisting of breast cancer, lung cancer, colorectal cancer, bladder cancer, kidney cancer, ovarian cancer and leukemia.

10. The method of claim 2, wherein the targeted therapeutic that is administered to the subject is the first agent targeted therapeutic.

11. The method of claim 2, wherein the targeted therapeutic that is administered to the subject is different than the first agent but targets the same signaling pathway as the first agent.

* * * * *